(12) United States Patent
Gobbi et al.

(10) Patent No.: US 9,801,961 B2
(45) Date of Patent: Oct. 31, 2017

(54) 2-PHENYLIMIDAZO[1,2-A]PYRIMIDINES AS IMAGING AGENTS

(71) Applicant: Hoffmann-La Roche Inc., Little Falls, NJ (US)

(72) Inventors: Luca Gobbi, Buus (CH); Henner Knust, Rheinfelden (DE); Matthias Koerner, Grenzach-Wyhlen (DE); Dieter Muri, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 64 days.

(21) Appl. No.: 14/945,969

(22) Filed: Nov. 19, 2015

(65) Prior Publication Data

US 2017/0128598 A1    May 11, 2017

Related U.S. Application Data

(63) Continuation of application No. PCT/EP2014/060203, filed on May 19, 2014.

(30) Foreign Application Priority Data

May 23, 2013    (EP) .................................... 13168830

(51) Int. Cl.
*A61K 51/04* (2006.01)
*C07D 487/04* (2006.01)
*A61K 49/00* (2006.01)

(52) U.S. Cl.
CPC .......... *A61K 51/0459* (2013.01); *A61K 49/00* (2013.01); *C07D 487/04* (2013.01)

(58) Field of Classification Search
CPC ................................ A61K 49/00; A61K 51/04
See application file for complete search history.

(56) References Cited

U.S. PATENT DOCUMENTS 6,642,229 B2 * 11/2003 Blackaby ............. C07D 231/12
514/233.2
2008/0219922 A1    9/2008 Goodman et al.
2009/0252679 A1    10/2009 Tanifuji et al.

FOREIGN PATENT DOCUMENTS

WO         2007/002540    1/2007
WO    WO-2007/034282    *  3/2007

* cited by examiner

Primary Examiner — Michael G Hartley
Assistant Examiner — Jagadishwar Samala
(74) Attorney, Agent, or Firm — Tamara A. Kale

(57) ABSTRACT

The present invention relates to compounds of general formula

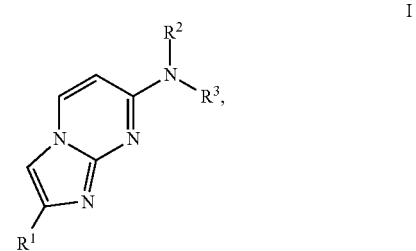

wherein
$R^1$ is (a) phenyl, optionally substituted by one or two substituents selected from $^3H$, halogen, lower alkyl, dimethyl-amino, NHC(O)-lower alkyl, C(O)O-lower alkyl, lower alkoxy, $OC(^3H)_3$, $O^{11}CH_3$, $OCH_2CH_2^{18}F$, lower alkoxy substituted by halogen, hydroxy, lower alkyl substituted by hydroxy, S-lower alkyl, (b) heterocyclyl group, (c) benzo[d][1,3]dioxol-5-yl, (d) 2,3-dihydrobenzo[b][1,4]dioxin-6-yl, (e) indolin-2-one, or (f) heteroaryl, selected from the group consisting of thiophenyl, benzofuranyl, benzothiophenyl, pyrazinyl, and benzothiazolyl;
$R^2$ is hydrogen, lower alkyl or lower alkyl substituted by halogen;
$R^3$ is lower alkyl, $C(^3H)_3$, $^{11}CH_3$, lower alkyl substituted by halogen, $-(CH_2)_2-$O-lower alkyl substituted by halogen or cycloalkyl; or
$R^2$ and $R^3$ form together with the N-atom to which they are attach a ring containing $-CH_2CH_2CHRCH_2CH_2-$, $-CH_2CH_2CHRCH_2-$, $-CH_2CHRCH_2-$, $-CH_2CH_2-NR-CH_2CH_2-$, $-CH_2CH_2-O-CH_2CH_2-$, or, R is hydrogen, halogen, lower alkyl substituted by halogen or lower alkoxy;
or to a pharmaceutically acceptable acid addition salt, to a racemic mixture or to its corresponding enantiomer and/or optical isomers thereof.
The compounds are suitable as imaging tool, which will improve diagnosis by identifying potential patients with excess of tau aggregates in the brain, which may be likely to develop Alzheimer's disease.

6 Claims, 1 Drawing Sheet

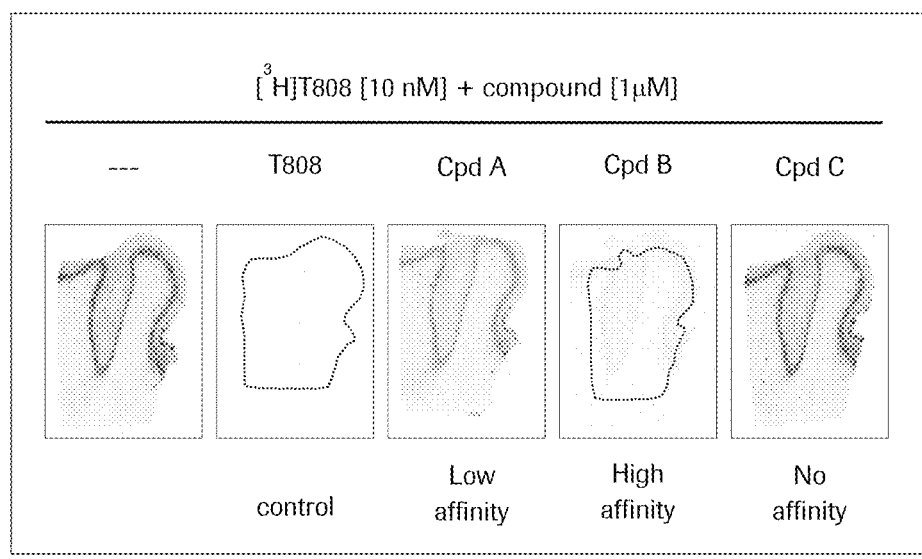

2-PHENYLIMIDAZO[1,2-A]PYRIMIDINES AS IMAGING AGENTS

CROSS REFERENCE TO RELATED APPLICATIONS

This application is a continuation of International Application No. PCT/EP2014/060203 having an international filing date of May 19, 2014, and which claims benefit under 35 U.S.C. §119 to European Patent Application No. 13168830.1 filed May 23, 2013. The entire contents of applications referenced above are incorporated herein by reference.

BACKGROUND

Alzheimer's disease (AD) is a progressive neurodegenerative disorder characterized by cognitive decline, irreversible memory loss, disorientation and language impairment (Arch. Neurol. 1985, 42(11), 1097-1105). Postmortem examination of AD brain sections reveals abundant senile plaques (SPs), composed of beta amyloid (Aβ) peptides, and numerous neurofibrillary tangles (NFTs) formed by filaments of hyperphosphorylated tau protein.

Tau belongs to the family of microtubule-associated proteins and is mainly expressed in neurons where it plays an important role in the assembly of tubulin monomers into microtubules to constitute the neuronal microtubule network as tracks for axonal transport (Brain Res. Rev. 2000, 33(1), 95-130). Tau is translated from a single gene located on chromosome 17 and the expression is developmentally regulated by an alternative splicing mechanism generating six different isoforms in the human adult brain that can be distinguished by their number of binding domains. The underlying mechanisms leading to tau hyperphosphorylation, misfolding and aggregation are not well understood, but the deposition of tau aggregates follows a stereotyped spatiotemporal pathway both at the intracellular levels as well as on the level of brain topography.

The recent discovery of tau gene mutations leading to frontotemporal dementia (FTD) with parkinsonism linked to chromosome 17 has reinforced the predominant role attributed to tau in the pathogenesis of neurodegenerative disorders and underlined the fact that distinct sets of tau isoforms expressed in different neuronal populations could lead to different pathologies (Biochim. Biophys. Acta 2005, 1739 (2) 240-250). Neurodegenerative diseases characterized by pathological tau accumulation are termed 'tauopathies' (Ann. Rev. Neurosci. 2001, 24, 1121-1159). Besides AD and FTD, other tauopathies include progressive supranuclear palsy (PSP), tangle-predominant dementia, Pick's disease, frontotemporal lobar degeneration (FTLD), Down's syndrome and others.

A direct correlation has been established between the progressive involvement of neocortical areas and the increasing severity of dementia, suggesting that pathological tau aggregates such as NFTs are a reliable marker of the neurodegenerative process. The degree of NFT involvement in AD is defined by Braak stages (Acta Neuropathol. 1991, 82, 239-259). Braak stages I and II are defined when NFT involvement is confined mainly to the transentorhinal region of the brain, stages III and IV are diagnosed when limbic regions such as the hippocampus are involved, and stages V and VI when extensive neocortical involvement is found.

Presently, detection of tau aggregates is only possible by histological analysis of biopsy or autopsy materials. In vivo imaging of tau pathology would provide novel insights into deposition of tau aggregates in the human brain and allow to non-invasively examine the degree of tau pathology, quantify changes in tau deposition over time, assess its correlation with cognition and analyze the efficacy of an anti-tau therapy. Potential ligands for detecting tau aggregates in the living brain must cross the blood-brain barrier and possess high affinity and specificity for tau aggregates. To this end, successful neuroimaging radiotracers must have appropriate lipophilicity (log D 1-3) and low molecular weight (<450), show rapid clearance from blood and low non-specific binding.

SUMMARY OF THE INVENTION

The present invention relates to compounds of general formula

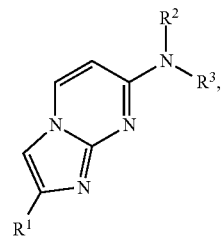

I $R^1$ is (a) phenyl, optionally substituted by one or two substituents selected from $^3H$, halogen, lower alkyl, dimethyl-amino, NHC(O)-lower alkyl, C(O)O-lower alkyl, lower alkoxy, $OC(^3H)_3$, $O^{11}CH_3$, $OCH_2CH_2^{18}F$, lower alkoxy substituted by halogen, hydroxy, lower alkyl substituted by hydroxy, S-lower alkyl, (b) heterocyclyl group, (c) benzo[d][1,3]dioxol-5-yl, (d) 2,3-dihydrobenzo[b][1,4]dioxin-6-yl, (e) indolin-2-one, or (f) heteroaryl, selected from the group consisting of thiophenyl, benzofuranyl, benzothiophenyl, pyrazinyl, and benzothiazolyl;

$R^2$ is hydrogen, lower alkyl or lower alkyl substituted by halogen;

$R^3$ is lower alkyl, $C(^3H)_3$, $^{11}CH_3$, lower alkyl substituted by halogen, —(CH$_2$)$_2$—O-lower alkyl substituted by halogen or cycloalkyl; or, $R^2$ and $R^3$ together with the N-atom to which they are attached form a ring comprising —CH$_2$CH$_2$CHRCH$_2$CH$_2$—, —CH$_2$CH$_2$CHRCH$_2$—, —CH$_2$CHRCH$_2$—, —CH$_2$CH$_2$—NR—CH$_2$CH$_2$—, —CH$_2$CH$_2$—O—CH$_2$CH$_2$—, or,

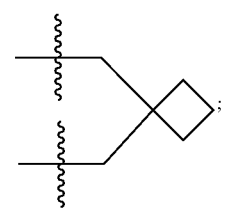

R is hydrogen, halogen, lower alkyl substituted by halogen or lower alkoxy;

or a pharmaceutically acceptable acid addition salt, a racemic mixture or its corresponding enantiomer and/or optical isomers thereof.

One object of the present application is to find an imaging tool which will improve diagnosis by identifying potential patients with excess of tau aggregates in the brain, who may be likely to develop Alzheimer's disease and to monitor the progression of the disease. When an anti-tau aggregate drug becomes available, imaging tau tangles in the brain may provide an essential tool for monitoring treatment.

Another object of the present invention is a method of imaging tau-aggregate deposits, comprising the steps of:
(a) introducing into a mammal a detectable quantity of a compound of formula I;
(b) allowing sufficient time for the compound to be associated with tau-aggregate deposits, and;
(c) detecting the compound associated with one or more tau-aggregate deposits.

BRIEF DESCRIPTION OF DRAWINGS

FIG. 1—shows the autoradiogram from a TAU radioligand in vitro displacement assay to assess the affinity of compounds for native tau aggregates. The compounds are co-incubated with the well-established tau specific radioligand [$^3$H]T808 and the compound's displacement potency of [$^3$H]T808 binding is determined by in vitro autoradiography using human Alzheimer's disease (AD) brain sections (see illustration below).

DETAILED DESCRIPTION OF THE INVENTION

It has been shown that the present compounds may be used for binding and imaging tau aggregates and related beta-sheet aggregates including besides others beta-amyloid aggregates or alpha-synuclein aggregates, especially for use in binding and imaging tau aggregates in Alzheimer patients.

Similar compounds are described for example in WO2011/117264 as modulators of phosphodiesterase 10A (PDE10A) for the treatment of central nervous system diseases and in WO2010/068453 and WO2010/068452 as modulators of fatty acid amide hydrolase. 2-Aryl-3-(heteroaryl)-imidazo(1,2-a)pyrimidines are described in WO0134605 for the treatment of conditions alleviated by the reduction of inflammatory cytokines.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, and isopropyl.

The term "cycloalkyl" denotes a non aromatic hydrocarbon ring, containing from 3 to 6 carbon atoms.

The term "alkoxy" denotes a group —O—R' wherein R' is lower alkyl as defined above.

The term "halogen" denotes chlorine, bromine, fluorine or iodine.

The term "lower alkyl substituted by halogen" denotes an alkyl group as defined above, wherein at least one hydrogen atom is replaced by a halogen atom.

The term "lower alkoxy substituted by halogen" denotes an alkoxy group as defined above, wherein at least one hydrogen atom is replaced by a halogen atom.

The term "heterocyclyl" denotes an unsaturated ring, containing 1-3 heteroatoms, selected from N, O or S, for example morpholinyl, piperazinyl, piperidinyl or pyrrolidinyl. $^3$H denotes a tritium atom.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

It has been found that the compounds of formula I may be used for binding and imaging tau aggregates and related beta-sheet aggregates including besides others beta-amyloid aggregates or alpha-synuclein aggregates.

One embodiment of the present invention are compounds of general formula (I)

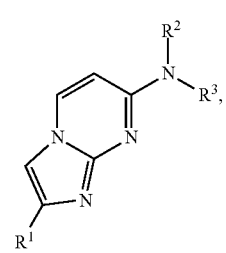

$R^1$ is (a) phenyl, optionally substituted by one or two substituents selected from $^3$H, halogen, lower alkyl, di-methyl-amino, NHC(O)-lower alkyl, C(O)O-lower alkyl, lower alkoxy, OC($^3$H)$_3$, O$^{11}$CH$_3$, OCH$_2$CH$_2{}^{18}$F, lower alkoxy substituted by halogen, hydroxy, lower alkyl substituted by hydroxy, S-lower alkyl, (b) heterocyclyl group, (c) benzo[d][1,3]dioxol-5-yl, (d) 2,3-dihydrobenzo[b][1,4]dioxin-6-yl, (e) indolin-2-one, or (f) heteroaryl, selected from the group consisting of thiophenyl, benzofuranyl, benzothiophenyl, pyrazinyl, and benzothiazolyl;

$R^2$ is hydrogen, lower alkyl or lower alkyl substituted by halogen;

$R^3$ is lower alkyl, C($^3$H)$_3$, $^{11}$CH$_3$, lower alkyl substituted by halogen, —(CH$_2$)$_2$—O-lower alkyl substituted by halogen or cycloalkyl; or, $R^2$ and $R^3$ together with the N-atom to which they are attached form a ring comprising —CH$_2$CH$_2$CHRCH$_2$CH$_2$—, —CH$_2$CH$_2$CHRCH$_2$—, —CH$_2$CHRCH$_2$—, —CH$_2$CH$_2$—NR—CH$_2$CH$_2$—, —CH$_2$CH$_2$—O—CH$_2$CH$_2$—, or,

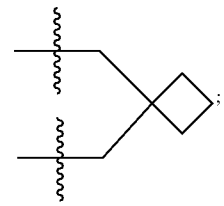 [SMILES: *CC1(C*)CCC1]

R is hydrogen, halogen, lower alkyl substituted by halogen or lower alkoxy;

or a pharmaceutically acceptable acid addition salt, a racemic mixture or a corresponding enantiomer and/or optical isomers thereof.

In a subembodiment $R^1$ is phenyl, optionally substituted by one or two substituents, selected from $^3$H, halogen, lower alkyl, di-methyl-amino, NHC(O)-lower alkyl, C(O)O-lower alkyl, lower alkoxy, OC($^3$H)$_3$, O$^{11}$CH$_3$, OCH$_2$CH$_2{}^{18}$F, lower alkoxy substituted by halogen, hydroxy, lower alkyl substituted by hydroxy, S-lower alkyl, or by a heterocyclyl group; or is benzo[d][1,3]dioxol-5-yl, 2,3-dihydrobenzo[b][1,4]dioxin-6-yl, indolin-2-one, or is heteroaryl, selected from the group consisting of thiophenyl, benzofuranyl, benzothiophenyl, pyrazinyl, or benzothiazolyl; R² is hydrogen, lower alkyl or lower alkyl substituted by halogen; R³ is lower alkyl, C(³H)₃, ¹¹CH₃, lower alkyl substituted by halogen, —(CH₂)₂—O-lower alkyl substituted by halogen or cycloalkyl; or R² and R³ form together with the N-atom to which they are attach a ring containing —CH₂CH₂CHRCH₂CH₂—, —CH₂CH₂CH₂CH₂—, —CH₂CH₂CH₂—, —CH₂CH₂—NR—CH₂CH₂—, —CH₂CH₂—O—CH₂CH₂—, —CH₂CH₂CHRCH₂—, —CH₂CHRCH₂— or,

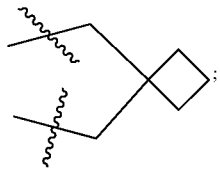 [SMILES: *CC1(C*)CCC1]

R is hydrogen, halogen, lower alkyl substituted by halogen or lower alkoxy; or a pharmaceutically acceptable acid addition salt, a racemic mixture or a corresponding enantiomer and/or optical isomers thereof.

Another object of the present invention are compounds of formula

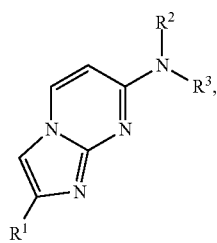

I-1 wherein

R¹ is phenyl, optionally substituted by one or two substituents, selected from ³H, halogen, lower alkyl, di-methylamino, NHC(O)-lower alkyl, C(O)O-lower alkyl, lower alkoxy, OC(³H)₃, O¹¹CH₃, OCH₂CH₂¹⁸F, lower alkoxy substituted by halogen, hydroxy, lower alkyl substituted by hydroxy, S-lower alkyl, or by a heterocyclyl group;

R² is hydrogen, lower alkyl or lower alkyl substituted by halogen;

R³ is lower alkyl, C(³H)₃, ¹¹CH₃, lower alkyl substituted by halogen, —(CH₂)₂—O-lower alkyl substituted by halogen or cycloalkyl; or R² and R³ form together with the N-atom to which they are attach a ring containing —CH₂CH₂CHRCH₂CH₂—, —CH₂CH₂CH₂CH₂—, —CH₂CH₂CH₂—, —CH₂CH₂—NR—CH₂CH₂—, —CH₂CH₂—O—CH₂CH₂—, —CH₂CH₂CHRCH₂—, —CH₂CHRCH₂— or,

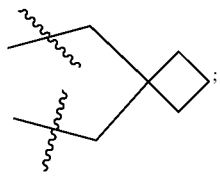 [SMILES: *CC1(C*)CCC1]

R is hydrogen, halogen, lower alkyl substituted by halogen or lower alkoxy;

or a pharmaceutically acceptable acid addition salt, a racemic mixture or its corresponding enantiomer and/or optical isomers thereof. For example the following compounds are embodiments of the present invention:

N-methyl-2-phenylimidazo[1,2-a]pyrimidin-7-amine
7-(4-fluoropiperidin-1-yl)-2-phenylimidazo[1,2-a]pyrimidine
7-(4-fluoropiperidin-1-yl)-2-(4-methoxyphenyl)imidazo[1,2-a]pyrimidine
2-(4-chlorophenyl)-7-(4-fluoropiperidin-1-yl)imidazo[1,2-a]pyrimidine
7-(4-fluoropiperidin-1-yl)-2-(3-methoxyphenyl)imidazo[1,2-a]pyrimidine
2-(4-fluorophenyl)-7-(4-fluoropiperidin-1-yl)imidazo[1,2-a]pyrimidine
4-[4-[7-(4-fluoropiperidin-1-yl)imidazo[1,2-a]pyrimidin-2-yl]phenyl]morpholine
7-(4-fluoropiperidin-1-yl)-2-(3-methylphenyl)imidazo[1,2-a]pyrimidine
7-(4-fluoropiperidin-1-yl)-2-(4-methylphenyl)imidazo[1,2-a]pyrimidine
2-(2-fluorophenyl)-7-(4-fluoropiperidin-1-yl)imidazo[1,2-a]pyrimidine
3-[7-(4-fluoropiperidin-1-yl)imidazo[1,2-a]pyrimidin-2-yl]phenol
7-(4-fluoropiperidin-1-yl)-2-(4-pyrrolidin-1-ylphenyl)imidazo[1,2-a]pyrimidine
7-(4-fluoropiperidin-1-yl)-2-[3-(trifluoromethoxy)phenyl]imidazo[1,2-a]pyrimidine
2-[3-(fluoromethoxy)phenyl]-7-pyrrolidin-1-ylimidazo[1,2-a]pyrimidine
2-[3-(2-fluoroethoxy)phenyl]-7-pyrrolidin-1-ylimidazo[1,2-a]pyrimidine
N,N-dimethyl-2-phenylimidazo[1,2-a]pyrimidin-7-amine
7-[4-(2-fluoroethyl)piperazin-1-yl]-2-(4-methoxyphenyl)imidazo[1,2-a]pyrimidine
7-[4-(2-fluoroethyl)piperazin-1-yl]-2-(3-methoxyphenyl)imidazo[1,2-a]pyrimidine
N-(2-fluoroethyl)-N-methyl-2-phenylimidazo[1,2-a]pyrimidin-7-amine
N-(2-fluoroethyl)-2-(3-methoxyphenyl)-N-methylimidazo[1,2-a]pyrimidin-7-amine
N-(2-fluoroethyl)-2-(4-methoxyphenyl)-N-methylimidazo[1,2-a]pyrimidin-7-amine
7-[4-(2-fluoroethyl)piperazin-1-yl]-2-phenylimidazo[1,2-a]pyrimidine
4-[2-(4-methoxyphenyl)imidazo[1,2-a]pyrimidin-7-yl]morpholine
4-[2-(3-methylphenyl)imidazo[1,2-a]pyrimidin-7-yl]morpholine
4-[2-(3,4-dimethoxyphenyl)imidazo[1,2-a]pyrimidin-7-yl]morpholine
4-(7-pyrrolidin-1-ylimidazo[1,2-a]pyrimidin-2-yl)phenol
2-[4-(2-fluoroethoxy)phenyl]-7-pyrrolidin-1-ylimidazo[1,2-a]pyrimidine
2-[4-(fluoromethoxy)phenyl]-7-pyrrolidin-1-ylimidazo[1,2-a]pyrimidine
7-[(3R)-3-methoxypyrrolidin-1-yl]-2-phenylimidazo[1,2-a]pyrimidine
7-[(3 S)-3-methoxypyrrolidin-1-yl]-2-phenylimidazo[1,2-a]pyrimidine
7-[(3R)-3-fluoropyrrolidin-1-yl]-2-(4-methoxyphenyl)imidazo[1,2-a]pyrimidine
7-[(3 S)-3-fluoropyrrolidin-1-yl]-2-(4-methoxyphenyl)imidazo[1,2-a]pyrimidine 2-(3-methoxyphenyl)-N,N-dimethylimidazo[1,2-a]pyrimidin-7-amine
2-(4-methoxyphenyl)-N,N-dimethylimidazo[1,2-a]pyrimidin-7-amine
N,N-dimethyl-2-(4-methylphenyl)imidazo[1,2-a]pyrimidin-7-amine
N,N-dimethyl-2-(3-methylphenyl)imidazo[1,2-a]pyrimidin-7-amine
4-[2-(3-methoxyphenyl)imidazo[1,2-a]pyrimidin-7-yl]morpholine
4-[2-(4-methylphenyl)imidazo[1,2-a]pyrimidin-7-yl]morpholine
2-(4-methoxyphenyl)-7-pyrrolidin-1-ylimidazo[1,2-a]pyrimidine
2-(4-methylphenyl)-7-pyrrolidin-1-ylimidazo[1,2-a]pyrimidine
N,N-dimethyl-2-(4-morpholin-4-ylphenyl)imidazo[1,2-a]pyrimidin-7-amine
2-[4-(dimethylamino)phenyl]-N,N-dimethylimidazo[1,2-a]pyrimidin-7-amine
2-(3-methoxyphenyl)-7-pyrrolidin-1-ylimidazo[1,2-a]pyrimidine
2-(3-methylphenyl)-7-pyrrolidin-1-ylimidazo[1,2-a]pyrimidine
2-(4-methoxyphenyl)-7-piperidin-1-ylimidazo[1,2-a]pyrimidine
2-(3-methoxyphenyl)-7-piperidin-1-ylimidazo[1,2-a]pyrimidine
2-(4-methylphenyl)-7-piperidin-1-ylimidazo[1,2-a]pyrimidine
2-(3-methylphenyl)-7-piperidin-1-ylimidazo[1,2-a]pyrimidine
2-(3,4-dimethoxyphenyl)-7-piperidin-1-ylimidazo[1,2-a]pyrimidine
7-[4-(2-fluoroethyl)piperidin-1-yl]-2-phenylimidazo[1,2-a]pyrimidine
7-[4-(2-fluoroethyl)piperidin-1-yl]-2-(3-methoxyphenyl)imidazo[1,2-a]pyrimidine
7-[4-(2-fluoroethyl)piperidin-1-yl]-2-(4-methoxyphenyl)imidazo[1,2-a]pyrimidine
7-[4-(2-fluoroethyl)piperidin-1-yl]-2-(3-methylphenyl)imidazo[1,2-a]pyrimidine
7-[4-(2-fluoroethyl)piperidin-1-yl]-2-(4-methylphenyl)imidazo[1,2-a]pyrimidine
4-[4-[7-[4-(2-fluoroethyl)piperidin-1-yl]imidazo[1,2-a]pyrimidin-2-yl]phenyl]morpholine
N-methyl-2-(3-methylphenyl)imidazo[1,2-a]pyrimidin-7-amine
N-[2-(2-fluoroethoxy)ethyl]-2-(4-methoxyphenyl)-N-methylimidazo[1,2-a]pyrimidin-7-amine
7-(2-azaspiro[3.3]heptan-2-yl)-2-(4-methoxyphenyl)imidazo[1,2-a]pyrimidine
N-ethyl-2-(4-methoxyphenyl)-N-methylimidazo[1,2-a]pyrimidin-7-amine
N,N-diethyl-2-(4-methoxyphenyl)imidazo[1,2-a]pyrimidin-7-amine
N-[2-(2-fluoroethoxy)ethyl]-N-methyl-2-(3-methylphenyl)imidazo[1,2-a]pyrimidin-7-amine
7-(azetidin-1-yl)-2-(4-methoxyphenyl)imidazo[1,2-a]pyrimidine
7-(3-fluoroazetidin-1-yl)-2-(4-methoxyphenyl)imidazo[1,2-a]pyrimidine
7-(3-fluoroazetidin-1-yl)-2-phenylimidazo[1,2-a]pyrimidine
7-(3-fluoroazetidin-1-yl)-2-(3-methylphenyl)imidazo[1,2-a]pyrimidine
N,N-dimethyl-4-(7-morpholin-4-ylimidazo[1,2-a]pyrimidin-2-yl)aniline
N-cyclopropyl-2-(4-methoxyphenyl)imidazo[1,2-a]pyrimidin-7-amine
N-isopropyl-2-(4-methoxy-phenyl)-imidazo[1,2-a]pyrimidin-7-amine
2-(4-methoxyphenyl)-N-(2,2,2-trifluoroethyl)imidazo[1,2-a]pyrimidin-7-amine
4-[7-(azetidin-1-yl)imidazo[1,2-a]pyrimidin-2-yl]phenol
7-(3-methoxyazetidin-1-yl)-2-(4-methoxyphenyl)imidazo[1,2-a]pyrimidine
N-methyl-2-(4-methylphenyl)imidazo[1,2-a]pyrimidin-7-amine
2-(4-methoxyphenyl)-N-methylimidazo[1,2-a]pyrimidin-7-amine
N-(2-fluoroethyl)-N-methyl-2-(4-methylphenyl)imidazo[1,2-a]pyrimidin-7-amine
N-(2-fluoroethyl)-N-methyl-2-(3-methylphenyl)imidazo[1,2-a]pyrimidin-7-amine
2-(4-methoxyphenyl)-7-(3-methylazetidin-1-yl)imidazo[1,2-a]pyrimidine
2-[4-(dimethylamino)phenyl]-N-methylimidazo[1,2-a]pyrimidin-7-amine
4-[7-(4-fluoropiperidin-1-yl)imidazo[1,2-a]pyrimidin-2-yl]-N,N-dimethylaniline
2-[4-(dimethylamino)phenyl]-N-(2-fluoroethyl)-N-methyl-imidazo[1,2-a]pyrimidin-7-amine
N-cyclopropyl-2-(4-methoxyphenyl)-N-methylimidazo[1,2-a]pyrimidin-7-amine
7-(azetidin-1-yl)-2-(4-methylphenyl)imidazo[1,2-a]pyrimidine
7-(azetidin-1-yl)-2-(3-methylphenyl)imidazo[1,2-a]pyrimidine
2-[4-(dimethylamino)phenyl]-N-(2-fluoroethyl)imidazo[1,2-a]pyrimidin-7-amine
7-(azetidin-1-yl)-2-[4-(fluoromethoxy)phenyl]imidazo[1,2-a]pyrimidine
2-methoxy-4-[7-(methylamino)imidazo[1,2-a]pyrimidin-2-yl]phenol
2-(3-bromophenyl)-N-methylimidazo[1,2-a]pyrimidin-7-amine
7-(4-fluoropiperidin-1-yl)-2-(4-methoxy-2,6-ditritiophenyl)imidazo[1,2-a]pyrimidine
7-(azetidin-1-yl)-2-[4-(tritritiomethoxy)phenyl]imidazo[1,2-a]pyrimidine
2-(3-methylphenyl)-N-(tritritiomethyl)imidazo[1,2-a]pyrimidine-7-amine
N—[$^{11}$C]methyl-2-(m-tolyl)imidazo[1,2-a]pyrimidin-7-amine
N-cyclopropyl-2-(4-[$^{11}$C]methoxyphenyl)imidazo[1,2-a]pyrimidin-7-amine
2-[4-(2-[$^{18}$F]fluoroethoxy)phenyl]-N-methyl-imidazo[1,2-a]pyrimidin-7-amine
[4-[7-(methylamino)imidazo[1,2-a]pyrimidin-2-yl]phenyl]methanol
2-(3-fluoro-4-methoxyphenyl)-N-methylimidazo[1,2-a]pyrimidin-7-amine
N-(4-(7-(methylamino)imidazo[1,2-a]pyrimidin-2-yl)phenyl)acetamide
7-(azetidin-1-yl)-2-(4-(2-fluoroethoxy)phenyl)imidazo[1,2-a]pyrimidine
7-(azetidin-1-yl)-2-(4-(3-fluoropropoxy)phenyl)imidazo[1,2-a]pyrimidine
7-(azetidin-1-yl)-2-(3-methoxyphenyl)imidazo[1,2-a]pyrimidine
[3-[7-(methylamino)imidazo[1,2-a]pyrimidin-2-yl]phenyl]methanol 7-(azetidin-1-yl)-2-(3-(2-fluoroethoxy)phenyl)imidazo[1,2-a]pyrimidine N-cyclopropyl-N-(2-fluoroethyl)-2-(4-methoxyphenyl)imidazo[1,2-a]pyrimidin-7-amine 2-(3-methoxyphenyl)-N-methylimidazo[1,2-a]pyrimidin-7-amine 7-(azetidin-1-yl)-2-(3-(fluoromethoxy)phenyl)imidazo[1,2-a]pyrimidine 7-(azetidin-1-yl)-2-(4-fluorophenyl)imidazo[1,2-a]pyrimidine 7-(azetidin-1-yl)-2-(3-fluorophenyl)imidazo[1,2-a]pyrimidine 7-(azetidin-1-yl)-2-(3,5-dimethoxyphenyl)imidazo[1,2-a]pyrimidine 4-(7-(methylamino)imidazo[1,2-a]pyrimidin-2-yl)phenol 2-(4-(2-fluoroethoxy)phenyl)-N-methylimidazo[1,2-a]pyrimidin-7-amine 2-(4-(3-fluoropropoxy)phenyl)-N-methylimidazo[1,2-a]pyrimidin-7-amine 3-(7-(methylamino)imidazo[1,2-a]pyrimidin-2-yl)phenol 7-(azetidin-1-yl)-2-(3-(methylthio)phenyl)imidazo[1,2-a]pyrimidine 7-(azetidin-1-yl)-2-(3-methyoxy-4-methylphenyl)imidazo[1,2-a]pyrimidine 7-(azetidin-1-yl)-2-(3,4-dimethoxyphenyl)imidazo[1,2-a]pyrimidine 2-(3-(2-fluoroethoxy)phenyl)-N-methylimidazo[1,2-a]pyrimidin-7-amine 2-(3-(3-fluoropropoxy)phenyl)-N-methylimidazo[1,2-a]pyrimidin-7-amine 2-(3-(fluoromethoxy)phenyl)-N-methylimidazo[1,2-a]pyrimidin-7-amine 2-(4-(fluoromethoxy)phenyl)-N-methylimidazo[1,2-a]pyrimidin-7-amine 3-(7-(cyclopropylamino)imidazo[1,2-a]pyrimidin-2-yl)phenol N-cyclopropyl-2-(3-(2-fluoroethoxy)phenyl)imidazo[1,2-a]pyrimidin-7-amine

[4-[7-(dimethylamino)imidazo[1,2-a]pyrimidin-2-yl]phenyl]methanol acetic acid adduct methyl 4-[7-(methylamino)imidazo[1,2-a]pyrimidin-2-yl]benzoate N-cyclopropyl-2-(3-(fluoromethoxy)phenyl)imidazo[1,2-a]pyrimidin-7-amine N-cyclopropyl-2-(4-(2-fluoroethoxy)phenyl)imidazo[1,2-a]pyrimidin-7-amine N-cyclopropyl-2-(4-(3-fluoropropoxy)phenyl)imidazo[1,2-a]pyrimidin-7-amine N-cyclopropyl-2-(4-(fluoromethoxy)phenyl)imidazo[1,2-a]pyrimidin-7-amine N-methyl-2-(4-(methylthio)phenyl)imidazo[1,2-a]pyrimidin-7-amine 2-(3,4-dimethoxyphenyl)-N-methylimidazo[1,2-a]pyrimidin-7-amine 2-(3-methoxy-4-methylphenyl)-N-methylimidazo[1,2-a]pyrimidin-7-amine or 2-(3,5-dimethoxyphenyl)-N-methylimidazo[1,2-a]pyrimidin-7-amine.

Another object of the present invention are further compounds of formula

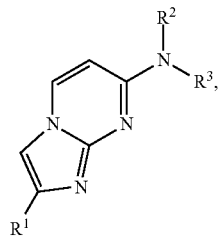

I-2 wherein

R¹ is benzo[d][1,3]dioxol-5-yl, 2,3-dihydrobenzo[b][1,4]dioxin-6-yl or indolin-2-one.

R² is hydrogen, lower alkyl or lower alkyl substituted by halogen;

R³ is lower alkyl, C(³H)₃, ¹¹CH₃, lower alkyl substituted by halogen, —(CH₂)₂—O-lower alkyl substituted by halogen or cycloalkyl; or R² and R³ form together with the N-atom to which they are attach a ring containing —CH₂CH₂CHRCH₂CH₂—, —CH₂CH₂CHRCH₂—, —CH₂CHRCH₂—, —CH₂CH₂—NR—CH₂CH₂—, —CH₂CH₂—O—CH₂CH₂—, or,

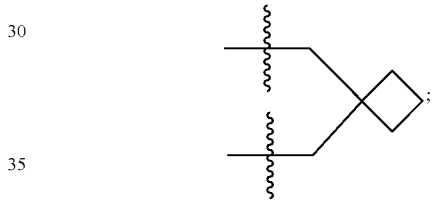

R is hydrogen, halogen, lower alkyl substituted by halogen or lower alkoxy;

or a pharmaceutically acceptable acid addition salt, a racemic mixture or its corresponding enantiomer and/or optical isomers thereof. For example the following compounds are embodiments of the present invention:

2-(1,3-benzodioxol-5-yl)-7-(4-fluoropiperidin-1-yl)imidazo[1,2-a]pyrimidine 2-(2,3-dihydro-1,4-benzodioxin-6-yl)-7-(4-fluoropiperidin-1-yl)imidazo[1,2-a]pyrimidine 2-(1,3-benzodioxol-5-yl)-N,N-dimethylimidazo[1,2-a]pyrimidin-7-amine 2-(2,3-dihydro-1,4-benzodioxin-6-yl)-N,N-dimethylimidazo[1,2-a]pyrimidin-7-amine 2-(1,3-benzodioxol-5-yl)-7-[4-(2-fluoroethyl)piperidin-1-yl]imidazo[1,2-a]pyrimidine 2-(2,3-dihydro-1,4-benzodioxin-6-yl)-7-[4-(2-fluoroethyl)piperidin-1-yl]imidazo[1,2-a]pyrimidine 2-(1,3-benzodioxol-5-yl)-N-methylimidazo[1,2-a]pyrimidin-7-amine 2-(1,3-benzodioxol-5-yl)-N-(2-fluoroethyl)-N-methylimidazo[1,2-a]pyrimidin-7-amine or 5-(7-(methylamino)imidazo[1,2-a]pyrimidin-2-yl)indolin-2-one.

One object of the present invention are further compounds of formula

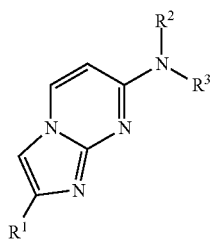
I-3 wherein
R¹ heteroaryl, selected from the group consisting of thiophenyl, benzofuranyl, benzothiophenyl, pyrazinyl or benzothiazolyl;
R² is hydrogen, lower alkyl or lower alkyl substituted by halogen;
R³ is lower alkyl, C($^3$H)$_3$, $^{11}$CH$_3$, lower alkyl substituted by halogen, —(CH$_2$)$_2$—O-lower alkyl substituted by halogen or cycloalkyl; or
R² and R³ form together with the N-atom to which they are attach a ring containing —CH$_2$CH$_2$CHRCH$_2$CH$_2$—, —CH$_2$CH$_2$CHRCH$_2$—, —CH$_2$CHRCH$_2$—, —CH$_2$CH$_2$—NR—CH$_2$CH$_2$—, —CH$_2$CH$_2$—O—CH$_2$CH$_2$—, or,

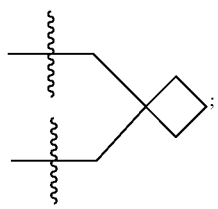 [SMILES: *CC1(C*)CCC1]

R is hydrogen, halogen, lower alkyl substituted by halogen or lower alkoxy;
or a pharmaceutically acceptable acid addition salt, a racemic mixture or its corresponding enantiomer and/or optical isomers thereof. For example the following compounds are embodiments of the present invention:
7-(4-fluoropiperidin-1-yl)-2-thiophen-3-ylimidazo[1,2-a]pyrimidine
2-(1-benzofuran-2-yl)-7-(4-fluoropiperidin-1-yl)imidazo[1,2-a]pyrimidine
2-(1-benzothiophen-2-yl)-7-(4-fluoropiperidin-1-yl)imidazo[1,2-a]pyrimidine
2-[7-(4-fluoropiperidin-1-yl)imidazo[1,2-a]pyrimidin-2-yl]-1,3-benzothiazole
N,N-dimethyl-2-thiophen-3-ylimidazo[1,2-a]pyrimidin-7-amine or
7-(4-fluoropiperidin-1-yl)-2-(pyrazin-2-yl)imidazo[1,2-a]pyrimidine.

The compounds of formula I may be used in binding and imaging tau aggregates, beta-amyloid aggregates, alpha-synuclein aggregates or huntingtin aggregates.
The preferred use of compounds of formula I is the use in binding and imaging tau aggregates in Alzheimer patients.
Furthermore, the compounds of formula I may be used in a tau-binding study.
The invention is also used for diagnostic imaging of tau-aggregate deposits in the brain of a mammal.

The present compounds of formula I

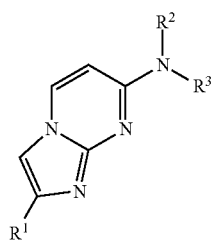
I and their pharmaceutically acceptable salts can be prepared by processes described below, which process comprises
a) coupling a compound of formula II (X=Cl, Br)

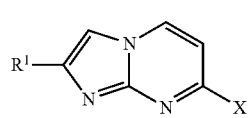
II with suitable amines HNR²R³ to afford compounds of formula I

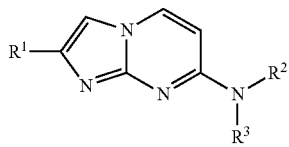
I wherein the substituents R¹, R² and R³ are defined as above, and, if desired, converting the obtained compounds into pharmaceutically acceptable acid addition salts or into a compound of formula I-2

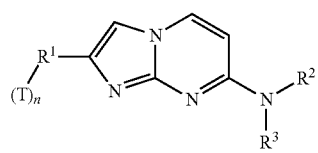
I-2 wherein T is tritium and n is 1 or 2,
or
b) coupling compounds of formula III

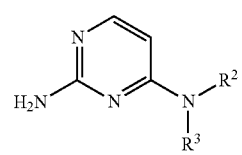
III with α-activated ketones of formula IV

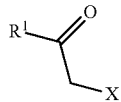

X = leaving group, e.g. Br to afford compounds of formula I

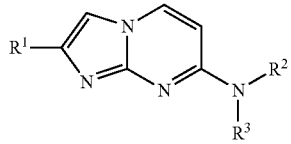

wherein the substituents $R^1$, $R^2$ and $R^3$ are defined as above and, if desired, converting the compounds obtained into pharmaceutically acceptable acid addition salts or into compounds of formula I-2

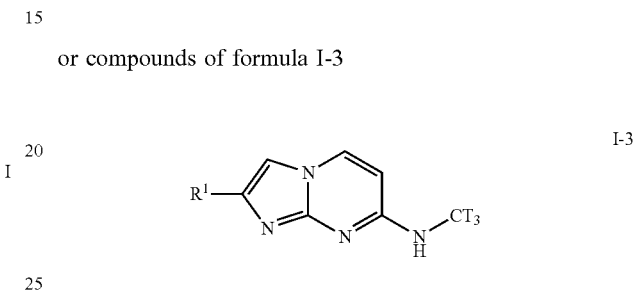

wherein T is tritium and n is 1 or 2,
or
c) reacting compounds of formula V

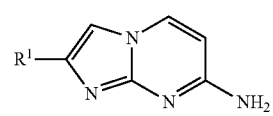

with suitable alkylation reagents to afford compounds of formula I

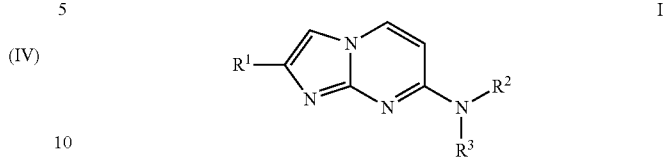

or compounds of formula I-3 wherein the substituents $R^1$, $R^2$ and $R^3$ are defined as above and wherein T is tritium, and, if desired, converting the compounds obtained into pharmaceutically acceptable acid addition salts or into compounds of formula I-2.

The following schemes 1-4 describe the processes for the preparation of compounds of formula I in more detail. The starting materials are known compounds or may be prepared according to methods known in the art.

The preparation of compounds of formula I of the present invention may be carried out in sequential or convergent synthetic routes. The skills required for carrying out the reactions and purifications of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 4, however, depending on the starting materials and their respective reactivity the sequence of reaction steps can be freely altered. Starting materials are either commercially available or can be prepared by methods analogous to the methods given below, by methods described in references cited in the description or in the examples, or by methods know in the art.

Scheme 1

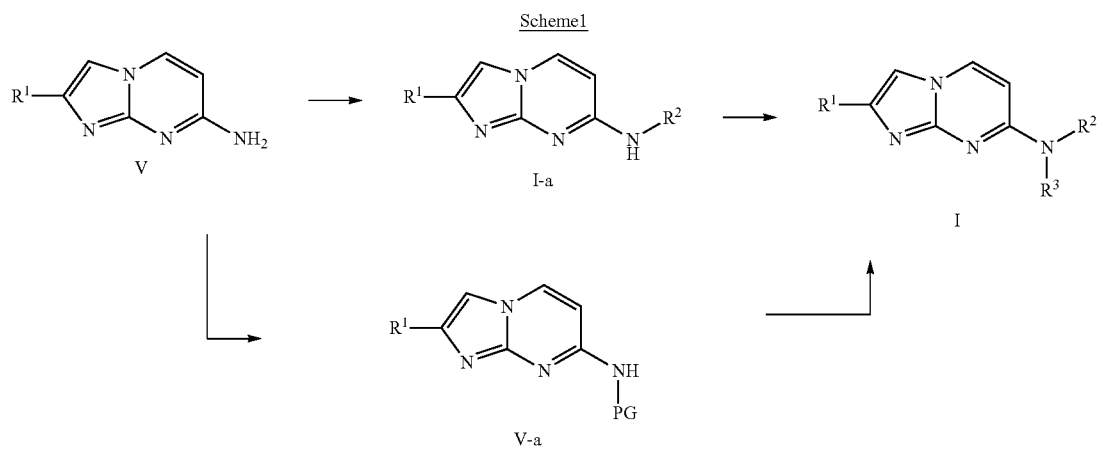

According to scheme 1, compounds of formula I wherein the substituents R¹, R² and R³ are as defined above can be prepared via consecutive alkylation reactions of amines V with suitable alkylation reagents, e.g. methyl iodide or an alkyl halide in presence of a base, e.g. sodium hydride in a suitable solvent, e.g. DMF at ambient or elevated temperature. Alternatively, amine V is first converted into a protected amine V-a via reaction with a suitable reagent, e.g. di-tert-butyldicarbonate, in a suitable solvent, followed by an alkylation reaction with a suitable alkylation reagent, e.g. methyliodine or an alkyl halogenide in presence of a base, e.g. sodium hydride in a suitable solvent, e.g. DMF at ambient or elevated temperature. Deprotection is then leading to compounds of formula I.

Scheme 3

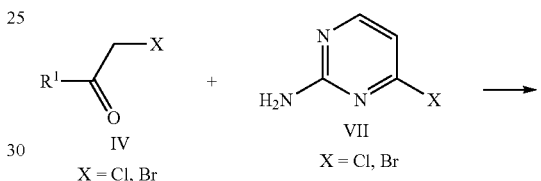

Scheme 2

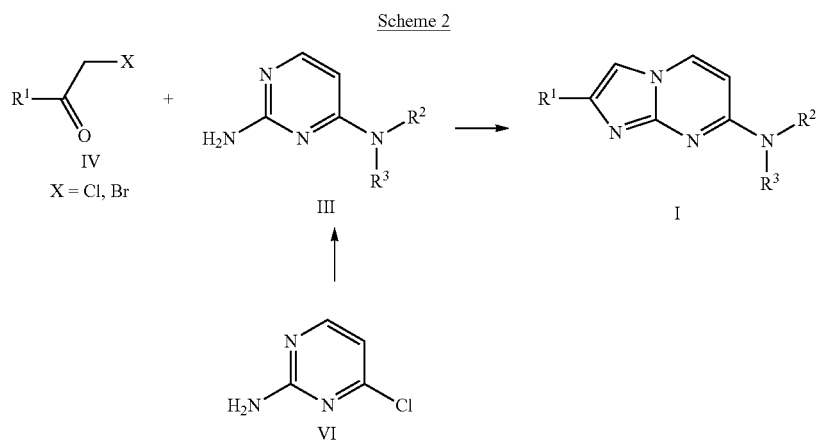

According to scheme 2, an activated ketone IV wherein R¹ is as defined above and X is a leaving group, e.g. Cl or Br is reacted with aminopyrimidines III wherein the substituents R² and R³ are as defined above in a suitable solvent, e.g. acetone or ethanol, at elevated temperature to afford compounds of formula I. Aminopyrimidines III can be synthesized starting from 2-amino-4-chloropyrimidine VI by heating with amines HNR²R³ and a suitable base, e.g. potassium carbonate or cesium carbonate, in a suitable solvent, e.g. sulfolane or NMP, at elevated temperature or by heating with amines HNR²R³ in water at elevated temperature.

-continued

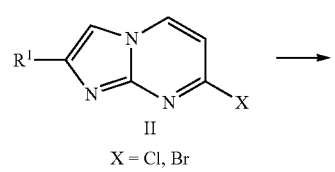

-continued

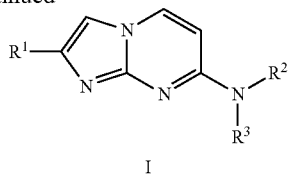

I

According to scheme 3, compounds of formula I wherein the substituents $R^1$, $R^2$ and $R^3$ are as defined above can also be prepared by coupling of an activated ketone IV wherein $R^1$ is as defined above and X is a leaving group, e.g. Cl or Br with aminopyrimidines VII wherein X is a leaving group, e.g. Cl or Br in a suitable solvent, e.g. acetone or ethanol, at elevated temperature to afford compounds of formula II. Transition-metal mediated coupling of II with an amine $HNR^1R^2$ in presence of a suitable metal source, e.g. $Pd_2(dba)_3$ a suitable ligand or additive, e.g. xantphos in a suitable solvent, e.g. dioxane and in presence of a suitable base, e.g. cesium carbonate at elevated temperature is affording compounds of formula I.

matography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The Scheme 4

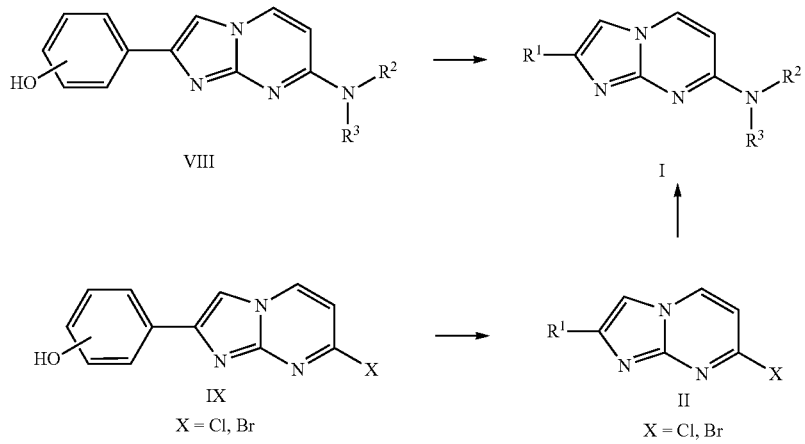

According to scheme 4, compounds of formula I wherein the substituents $R^1$, $R^2$ and $R^3$ are as defined above can also be prepared by alkylation of phenols VIII using a suitable alkylation reagent, e.g. alkyl halides like 1-fluoroethyl bromide or alkyl tosylates like fluoromethyl tosylate, in presence of a suitable base, e.g. cesium carbonate or sodium hydride, in a suitable solvent, e.g. DMF, at ambient or elevated temperature. In analogy, phenols IX can be alkylated to afford compounds of formula II which are then further transformed into compounds of formula I.

Compounds, wherein the substitution on $R^1$ is $^3H$, $OC(^3H)_3$, $O^{11}CH_3$ or $OCH_2CH_2^{18}F$ or $R^3$ is $C(^3H)_3$ or $^{11}CH_3$, may be prepared in conventional manner starting from compounds of formula I or compounds of formula V as described in the specific examples 100 to 106.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chrotemperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like. The compounds were investigated in accordance with the test given hereinafter.

TAU Radioligand-In-Vitro Displacement Assay

This in vitro binding assay assesses the affinity of compounds for native tau aggregates. The compounds are co-incubated with the well-established tau specific radioligand [$^3H$]T808 and the compound's displacement potency of [$^3H$]T808 binding is determined by in vitro autoradiography using human Alzheimer's disease (AD) brain sections (FIG. 1).

Materials

AD human brains are purchased from Banner Sun Health Research Institute (Sun City, Ariz., USA). Pathological diagnosis of AD is made according to standard NIA-Reagan Institute criteria based on neuropathological data. The radioligand [³H]T808 was synthesized in-house ([³H]-2-[4-(2-Fluoro-ethyl)-piperidin-1-yl]-benzo[4,5]imidazo[1,2-a]pyrimidine, radiochemical purity 99.0%). As a reference cold T808 is used (2-[4-(2-Fluoro-ethyl)-piperidin-1-yl]-benzo[4,5]imidazo[1,2-a]pyrimidine). For the autoradiography FujiFilm Imaging Plates (BAS-IP TR 2025) are exposed to the sections and read with a FujiFilm IP reader (BAS-5000).

Method

Ten μm thick human AD brain sections are generated with a cryostat (Leica CM3050) at −17° C. chamber temperature and −15° C. object temperature. Sections are transferred to Histobond+microscope slides (Marienfeld Laboratory Glasware). After drying for 3 hours at room temperature the sections are stored at −20° C. The sections are incubated with the radioligand (10 nM) and the respective cold compound (at various concentrations) in 50 mM Tris buffer, pH 7.4 at room temperature for 30 min. After washing 3×10 min at 4° C. in 50 mM Tris buffer, pH 7.4 and 3 quick dips in H₂O dist. at 4° C. the sections are dried at 4° C. for 3 h. The sections are placed in a FujiFilm Cassette (BAS 2025), exposed with an Imaging Plate for five days and afterwards scanned with a resolution of 25 μM per pixel.

Data Analysis

The signal intensity (Dens—PSL/mm2) in the region of interest (ROI) of the autoradiogram is quantified with the software MCID analysis (version 7.0, Imaging Research Inc.). The specific binding (SB) of [³H]T808 binding in absence or in presence of a compound is calculated by subtracting the non-specific binding signal in the white matter, thus yielding $SB_{[3H]T808\ only}$ and $SB_{compund}$. The % displacement by the various compounds is calculated as following:

$$\%\ displacement = 100 - (SB_{compund}/SB_{[3H]T808\ only}) * 100.$$

Validation Data

In each experiment cold T808 is used as a positive internal control. Co-incubation of equimolar amounts of hot and cold T808 is expected to reduce specific binding by approximately 50%.

References

A. K. Szardenings et al. 'Imaging agents for detecting neurological disorders'. US Patent Application US20110182812

W. Zhang et al., 'A highly selective and specific PET tracer for imaging of tau pathologies'. *Journal of Alzheimer's Disease* 31 (2012) 601-612.

Pharmaceutical Preparations

The compounds of formula I as well as their pharmaceutically acceptable salts can be administered in form of pharmaceutical preparations, normally parenterally, e.g. in the form of injection solutions.

Suitable excipients for injection solutions are e.g. water, alcohols, polyols, glycerol, vegetable oils etc.

TABLE I

| Structure | Name | % displacement of [³H]T808 (10 nM) at 1 uM | % displacement of [³H]T808 (10 nM) at 10 nM | Expl. |
|---|---|---|---|---|
| 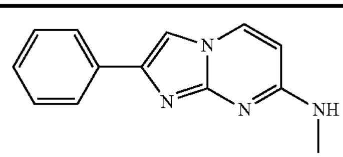 | N-Methyl-2-phenylimidazo[1,2-a]pyrimidin-7-amine | | 37 | 1 |
| 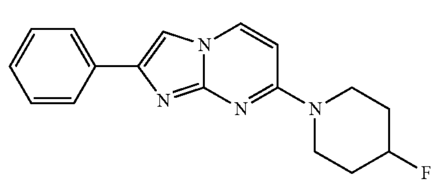 [SMILES: FC1CCN(c2ccn3cc(-c4ccccc4)nc3n2)CC1] | 7-(4-Fluoropiperidin-1-yl)-2-phenylimidazo[1,2-a]pyrimidine | 72 | 19 | 2 |
| 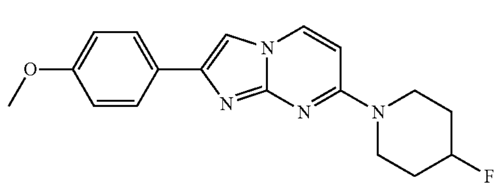 [SMILES: COc1ccc(-c2cn3ccc(N4CCC(F)CC4)nc3n2)cc1] | 7-(4-Fluoropiperidin-1-yl)-2-(4-methoxyphenyl)imidazo[1,2-a]pyrimidine | 87 | 31 | 3 |

TABLE-continued

I

| Structure | Name | % displacement of [³H]T808 (10 nM) at | | Expl. |
|---|---|---|---|---|
| | | 1 uM | 10 nM | |
| (4-chlorophenyl structure) | 2-(4-Chlorophenyl)-7-(4-fluoropiperidin-1-yl)imidazo[1,2-a]pyrimidine | 58 | | 4 |
| (3-methoxyphenyl structure) | 7-(4-Fluoropiperidin-1-yl)-2-(3-methoxyphenyl)imidazo[1,2-a]pyrimidine | 74 | 33 | 5 |
| (4-fluorophenyl structure) | 2-(4-Fluorophenyl)-7-(4-fluoropiperidin-1-yl)imidazo[1,2-a]pyrimidine | 65 | | 6 |
| (benzodioxol structure) | 2-(1,3-Benzodioxol-5-yl)-7-(4-fluoropiperidin-1-yl)imidazo[1,2-a]pyrimidine | 75 | 21 | 7 |
| (benzodioxin structure) | 2-(2,3-Dihydro-1,4-benzodioxin-6-yl)-7-(4-fluoropiperidin-1-yl)imidazo[1,2-a]pyrimidine | 72 | | 8 |
| (morpholinophenyl structure) | 4-[4-[7-(4-Fluoropiperidin-1-yl)imidazo[1,2-a]pyrimidin-2-yl]phenyl]morpholine | 75 | | 9 |
| (3-methylphenyl structure) | 7-(4-Fluoropiperidin-1-yl)-2-(3-methylphenyl)imidazo[1,2-a]pyrimidine | 79 | | 10 |

TABLE-continued

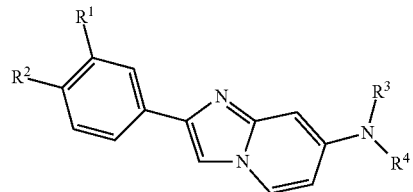

I

| Structure | Name | % displacement of [³H]T808 (10 nM) at | | Expl. |
|---|---|---|---|---|
| | | 1 uM | 10 nM | |
| 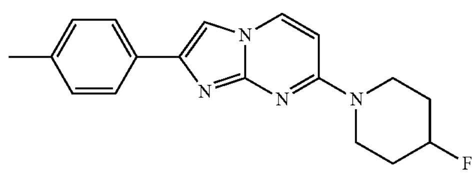 [SMILES: Cc1ccc(-c2cn3ccc(N4CCC(F)CC4)nc3n2)cc1] | 7-(4-Fluoropiperidin-1-yl)-2-(4-methylphenyl)imidazo[1,2-a]pyrimidine | 81 | 4 | 11 |
| 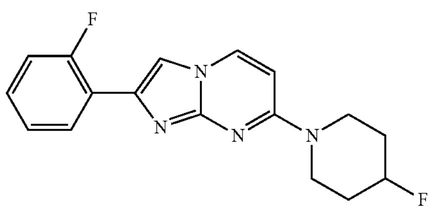 [SMILES: Fc1ccccc1-c1cn2ccc(N3CCC(F)CC3)nc2n1] | 2-(2-Fluorophenyl)-7-(4-fluoropiperidin-1-yl)imidazo[1,2-a]pyrimidine | 50 | | 12 |
| 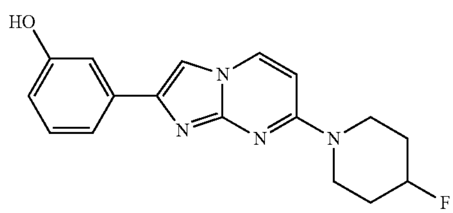 [SMILES: Oc1cccc(-c2cn3ccc(N4CCC(F)CC4)nc3n2)c1] | 3-[7-(4-Fluoropiperidin-1-yl)imidazo[1,2-a]pyrimidin-2-yl]phenol | 67 | | 13 |
| 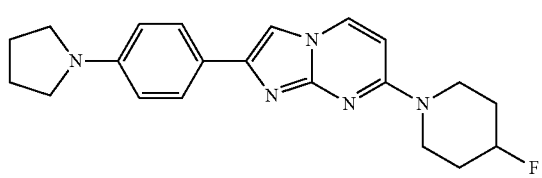 [SMILES: FC1CCN(c2ccn3cc(-c4ccc(N5CCCC5)cc4)nc3n2)CC1] | 7-(4-Fluoropiperidin-1-yl)-2-(4-pyrrolidin-1-ylphenyl)imidazo[1,2-a]pyrimidine | 75 | 18 | 14 |
| 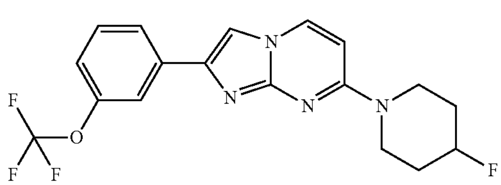 [SMILES: FC1CCN(c2ccn3cc(-c4cccc(OC(F)(F)F)c4)nc3n2)CC1] | 7-(4-Fluoropiperidin-1-yl)-2-[3-(trifluoromethoxy)phenyl]imidazo[1,2-a]pyrimidine | | 14 | 15 |
| 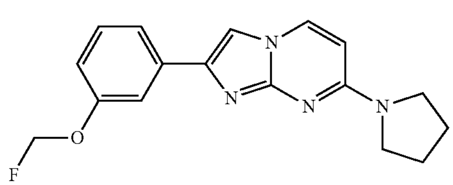 [SMILES: FCOc1cccc(-c2cn3ccc(N4CCCC4)nc3n2)c1] | 2-[3-(Fluoromethoxy)phenyl]-7-pyrrolidin-1-ylimidazo[1,2-a]pyrimidine | 88 | 27 | 16 |

TABLE-continued

I

| Structure | Name | % displacement of [³H]T808 (10 nM) at | | Expl. |
|---|---|---|---|---|
| | | 1 uM | 10 nM | |
| 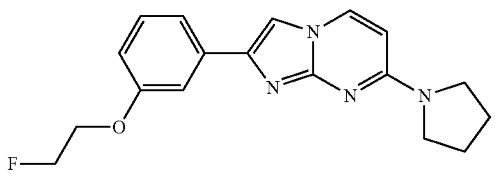 [SMILES: FCCOc1cccc(-c2cn3ccc(N4CCCC4)nc3n2)c1] | 2-[3-(2-Fluoroethoxy)phenyl]-7-pyrrolidin-1-ylimidazo[1,2-a]pyrimidine | 76 | | 17 |
| 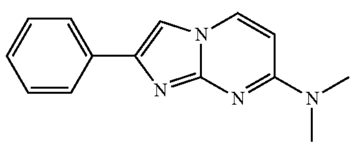 [SMILES: CN(C)c1ccn2cc(-c3ccccc3)nc2n1] | N,N-Dimethyl-2-phenylimidazo[1,2-a]pyrimidin-7-amine | 92 | 35 | 18 |
| ClH | 7-[4-(2-Fluoroethyl)piperazin-1-yl]-2-(4-methoxyphenyl)imidazo[1,2-a]pyrimidine | 74 | | 19 |
| ClH | 7-[4-(2-Fluoroethyl)piperazin-1-yl]-2-(3-methoxyphenyl)imidazo[1,2-a]pyrimidine | 51 | | 20 |
| 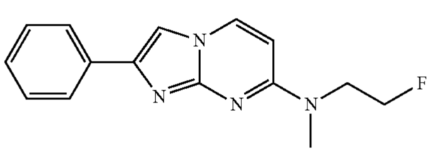 [SMILES: CN(CCF)c1ccn2cc(-c3ccccc3)nc2n1] | N-(2-Fluorethyl)-N-methyl-2-phenylimidazo[1,2-a]pyrimidin-7-amine | 84 | | 21 |
| 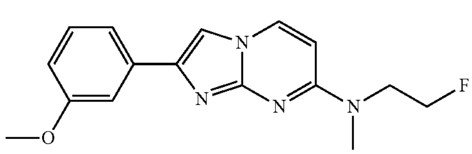 [SMILES: COc1cccc(-c2cn3ccc(N(C)CCF)nc3n2)c1] | N-(2-Fluoroethyl)-2-(3-methoxyphenyl)-N-methylimidazo[1,2-a]pyrimidin-7-amine | 82 | | 22 |
| 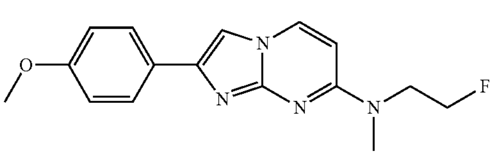 [SMILES: COc1ccc(-c2cn3ccc(N(C)CCF)nc3n2)cc1] | N-(2-Fluoroethyl)-2-(4-methoxyphenyl)-N-methylimidazo[1,2-a]pyrimidin-7-amine | 92 | 33 | 23 |

TABLE-continued

I

| Structure | Name | % displacement of [³H]T808 (10 nM) at | | Expl. |
|---|---|---|---|---|
| | | 1 uM | 10 nM | |
| (phenyl-imidazo[1,2-a]pyrimidine with piperazine-CH2CH2F, ClH) | 7-[4-(2-Fluoroethyl)piperazin-1-yl]-2-phenylimidazo[1,2-a]pyrimidine | 64 | | 24 |
| (4-methoxyphenyl-imidazo[1,2-a]pyrimidine with morpholine) | 4-[2-(4-Methoxyphenyl)imidazo[1,2-a]pyrimidin-7-yl]morpholine | | 16 | 25 |
| (3-methylphenyl-imidazo[1,2-a]pyrimidine with morpholine) | 4-[2-(3-Methylphenyl)imidazo[1,2-a]pyrimidin-7-yl]morpholine | | 13 | 26 |
| (3,4-dimethoxyphenyl-imidazo[1,2-a]pyrimidine with morpholine) | 4-[2-(3,4-Dimethoxyphenyl)imidazo[1,2-a]pyrimidin-7-yl]morpholine | | 17 | 27 |
| (4-hydroxyphenyl-imidazo[1,2-a]pyrimidine with pyrrolidine) | 4-(7-Pyrrolidin-1-ylimidazo[1,2-a]pyrimidin-2-yl)phenol | | 22 | 28 |
| (4-(2-fluoroethoxy)phenyl-imidazo[1,2-a]pyrimidine with pyrrolidine) | 2-[4-(2-Fluoroethoxy)phenyl]-7-pyrrolidin-1-ylimidazo[1,2-a]pyrimidine | | 15 | 29 |

TABLE-continued

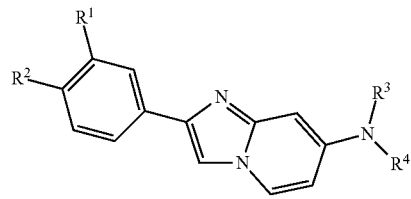

I

| Structure | Name | % displacement of [³H]T808 (10 nM) at 1 uM | 10 nM | Expl. |
|---|---|---|---|---|
| 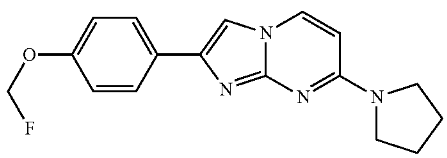 [SMILES: FCOc1ccc(-c2cn3ccc(N4CCCC4)nc3n2)cc1] | 2-[4-(Fluoromethoxy)phenyl]-7-pyrrolidin-1-ylimidazo[1,2-a]pyrimidine | 9 | | 30 |
| 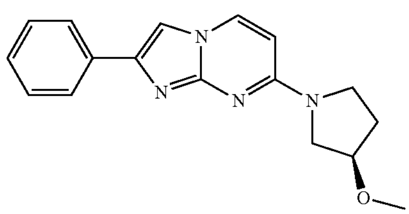 [SMILES: CO[C@@H]1CCN(c2ccn3cc(-c4ccccc4)nc3n2)C1] | 7-[(3R)-3-Methoxypyrrolidin-1-yl]-2-phenylimidazo[1,2-a]pyrimidine | 7 | | 31 |
| 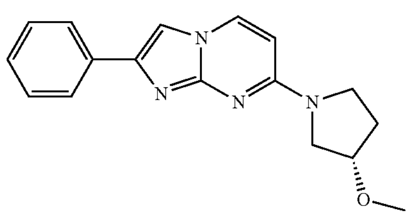 [SMILES: CO[C@H]1CCN(c2ccn3cc(-c4ccccc4)nc3n2)C1] | 7-[(3S)-3-Methoxypyrrolidin-1-yl]-2-phenylimidazo[1,2-a]pyrimidine | 13 | | 32 |
| 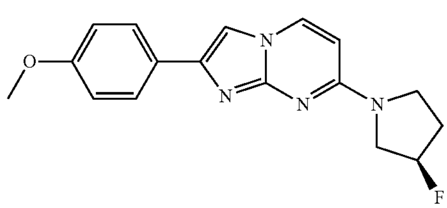 [SMILES: COc1ccc(-c2cn3ccc(N4CC[C@@H](F)C4)nc3n2)cc1] | 7-[(3R)-3-Fluoropyrrolidin-1-yl]-2-(4-methoxyphenyl)imidazo[1,2-a]pyrimidine | 25 | | 33 |
| 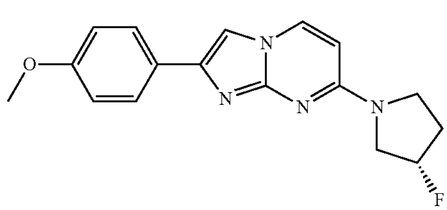 [SMILES: COc1ccc(-c2cn3ccc(N4CC[C@H](F)C4)nc3n2)cc1] | 7-[(3S)-3-Fluoropyrrolidin-1-yl]-2-(4-methoxyphenyl)imidazo[1,2-a]pyrimidine | 15 | | 34 |
| 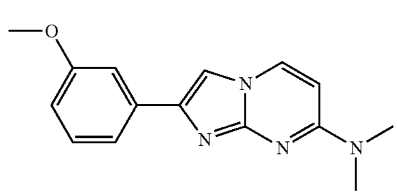 | 2-(3-Methoxyphenyl)-N,N-dimethylimidazo[1,2-a]pyrimidin-7-amine | 34 | | 35 |

TABLE-continued

I

| Structure | Name | % displacement of [³H]T808 (10 nM) at | | Expl. |
|---|---|---|---|---|
| | | 1 uM | 10 nM | |
| 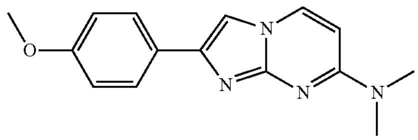 | 2-(4-Methoxyphenyl)-N,N-dimethylimidazo[1,2-a]pyrimidin-7-amine | 47 | | 36 |
| 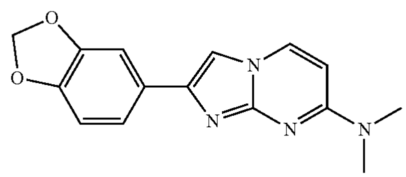 [SMILES: CN(C)c1ccn2cc(-c3ccc4c(c3)OCO4)nc2n1] | 2-(1,3-Benzodioxol-5-yl)-N,N-dimethylimidazo[1,2-a]pyrimidin-7-amine | 46 | | 37 |
| 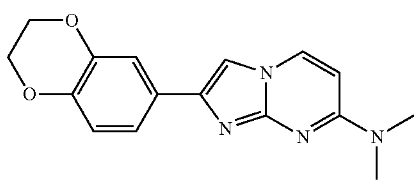 [SMILES: CN(C)c1ccn2cc(-c3ccc4c(c3)OCCO4)nc2n1] | 2-(2,3-Dihydro-1,4-benzodioxin-6-yl)-N,N-dimethylimidazo[1,2-a]pyrimidin-7-amine | 37 | | 38 |
| 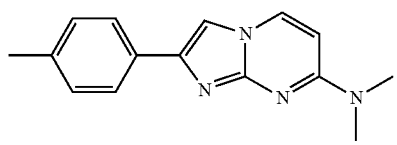 | N,N-Dimethyl-2-(4-methylphenyl)imidazo[1,2-a]pyrimidin-7-amine | 49 | | 39 |
| 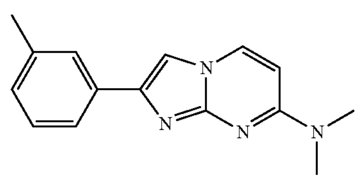 [SMILES: Cc1cccc(-c2cn3ccc(N(C)C)nc3n2)c1] | N,N-Dimethyl-2-(3-methylphenyl)imidazo[1,2-a]pyrimidin-7-amine | 51 | | 40 |
| 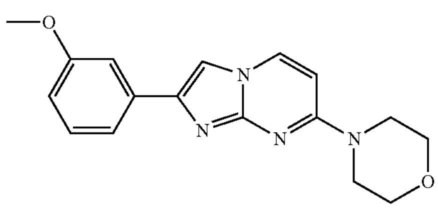 [SMILES: COc1cccc(-c2cn3ccc(N4CCOCC4)nc3n2)c1] | 4-[2-(3-Methoxyphenyl)imidazo[1,2-a]pyrimidin-7-yl]morpholine | 16 | | 41 |
| 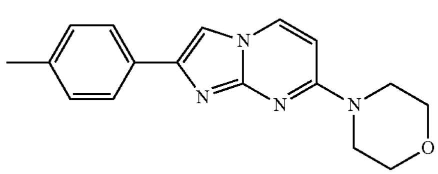 [SMILES: Cc1ccc(-c2cn3ccc(N4CCOCC4)nc3n2)cc1] | 4-[2-(4-Mehtyphenyl)imidazo[1,2-a]pyrimidin-7-yl]morpholine | 8 | | 42 |

TABLE-continued

I

| Structure | Name | % displacement of [³H]T808 (10 nM) at | | Expl. |
|---|---|---|---|---|
| | | 1 uM | 10 nM | |
| 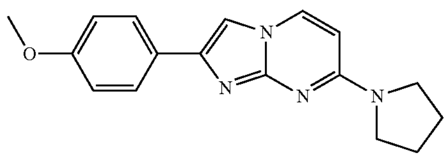 [SMILES: COc1ccc(-c2cn3ccc(N4CCCC4)nc3n2)cc1] | 2-(4-Methoxyphenyl)-7-pyrrolidin-1-ylimidazo[1,2-a]pyrimidine | | 29 | 43 |
| 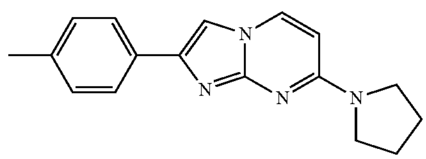 [SMILES: Cc1ccc(-c2cn3ccc(N4CCCC4)nc3n2)cc1] | 2-(4-Methylphenyl)-7-pyrrolidin-1-ylimidazo[1,2-a]pyrimidine | | 28 | 44 |
| 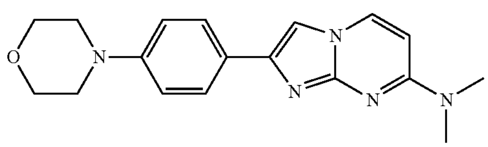 [SMILES: CN(C)c1ccn2cc(-c3ccc(N4CCOCC4)cc3)nc2n1] | N,N-Dimethyl-2-(4-morpholin-4-ylphenyl)imidazo[1,2-a]pyrimidin-7-amine | | 29 | 45 |
| 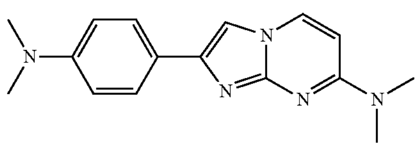 | 2-[4-(Dimethylamino)phenyl]-N,N-dimethylimidazo[1,2-a]pyrimidin-7-amine | | 43 | 46 |
| 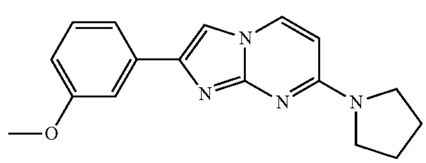 [SMILES: COc1cccc(-c2cn3ccc(N4CCCC4)nc3n2)c1] | 2-(3-Methoxyphenyl)-7-pyrrolidin-1-ylimidazo[1,2-a]pyrimidine | | 20 | 47 |
| 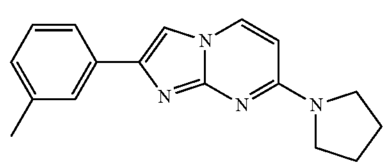 [SMILES: Cc1cccc(-c2cn3ccc(N4CCCC4)nc3n2)c1] | 2-(3-Methylphenyl)-7-pyrrolidin-1-ylimidazo[1,2-a]pyrimidine | | 23 | 48 |
| 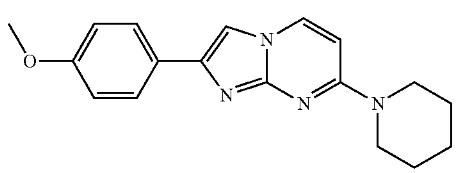 [SMILES: COc1ccc(-c2cn3ccc(N4CCCCC4)nc3n2)cc1] | 2-(4-Methoxyphenyl)-7-piperidin-1-ylimidazo[1,2-a]pyrimidine | | 17 | 49 |

TABLE-continued

I

| Structure | Name | % displacement of [³H]T808 (10 nM) at | | Expl. |
|---|---|---|---|---|
| | | 1 uM | 10 nM | |
| 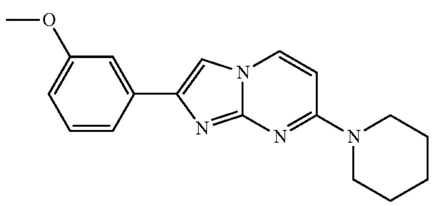 [SMILES: COc1cccc(-c2cn3ccc(N4CCCCC4)nc3n2)c1] | 2-(3-Methoxyphenyl)-7-piperidin-1-ylimidazo[1,2-a]pyrimidine | | 14 | 50 |
| 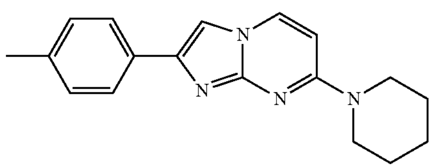 [SMILES: Cc1ccc(-c2cn3ccc(N4CCCCC4)nc3n2)cc1] | 2-(4-Methylphenyl)-7-piperidin-1-ylimidazo[1,2-a]pyrimidine | | 8 | 51 |
| 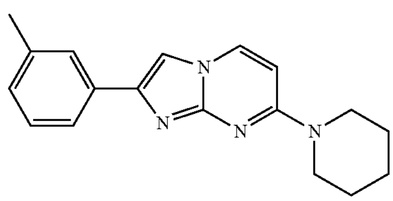 [SMILES: Cc1cccc(-c2cn3ccc(N4CCCCC4)nc3n2)c1] | 2-(3-Methylphenyl)-7-piperidin-1-ylimidazo[1,2-a]pyrimidine | | 14 | 52 |
| 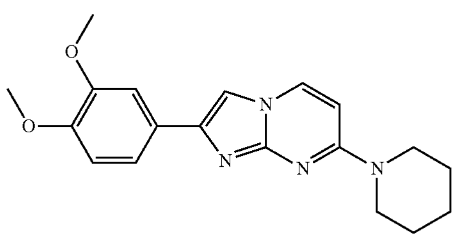 [SMILES: COc1ccc(-c2cn3ccc(N4CCCCC4)nc3n2)cc1OC] | 2-(3,4-Dimethoxyphenyl)-7-piperidin-1-ylimidazo[1,2-a]pyrimidine | | 6 | 53 |
| 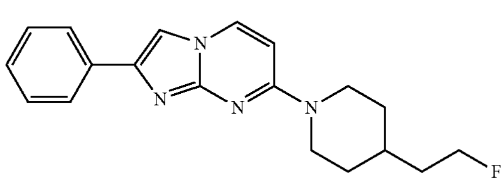 [SMILES: FCCC1CCN(c2ccn3cc(-c4ccccc4)nc3n2)CC1] | 7-[4-(2-Fluoroethyl)piperidin-1-yl]-2-phenylimidazo[1,2-a]pyrimidine | | 14 | 54 |
| 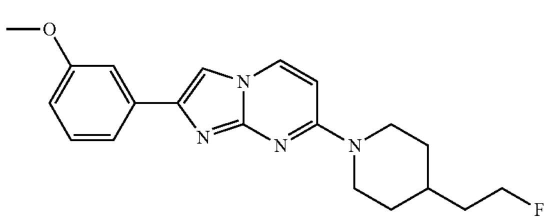 [SMILES: COc1cccc(-c2cn3ccc(N4CCC(CCF)CC4)nc3n2)c1] | 7-[4-(2-Fluoroethyl)piperidin-1-yl]-2-(3-methoxyphenyl)imidazo[1,2-a]pyrimidine | | 10 | 55 |

TABLE-continued

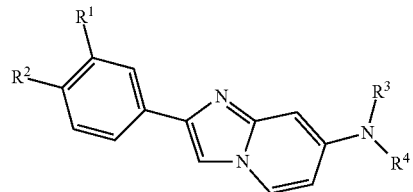

I

| Structure | Name | % displacement of [³H]T808 (10 nM) at | | Expl. |
|---|---|---|---|---|
| | | 1 uM | 10 nM | |
| 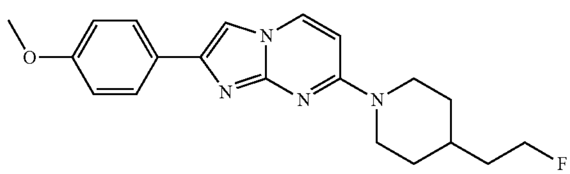 [SMILES: COc1ccc(-c2cn3ccc(N4CCC(CCF)CC4)nc3n2)cc1] | 7-[4-(2-Fluoroethyl)piperidin-1-yl]-2-(4-methoxyphenyl)imidazo[1,2-a]pyrimdiine | | 9 | 56 |
| 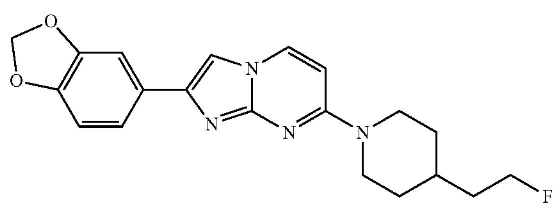 [SMILES: FCCC1CCN(c2ccn3cc(-c4ccc5c(c4)OCO5)nc3n2)CC1] | 2-(1,3-Benzodioxol-5-yl)-7-[4-(2-fluoroethyl)piperidin-1-yl]imidazo[1,2-a]pyrimidine | | 9 | 57 |
| 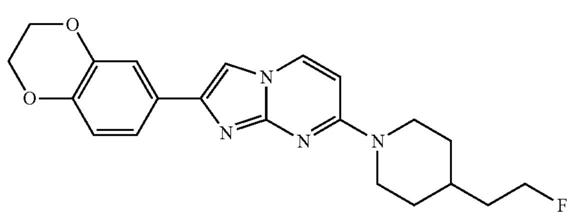 [SMILES: FCCC1CCN(c2ccn3cc(-c4ccc5c(c4)OCCO5)nc3n2)CC1] | 2-(2,3-Dihydro-1,4-benzodioxin-6-yl)-7-[4-(2-fluoroethyl)piperidin-1-yl]imidazo[1,2-a]pyrimidine | | 18 | 58 |
| 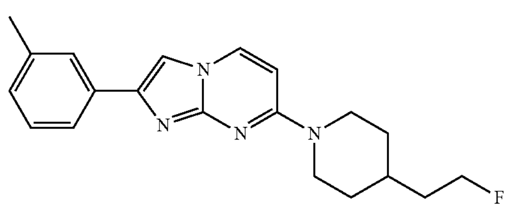 [SMILES: Cc1cccc(-c2cn3ccc(N4CCC(CCF)CC4)nc3n2)c1] | 7-[4-(2-Fluoroethyl)piperidin-1-yl]-2-(3-methylphenyl)imidazo[1,2-a]pyrimidine | | 10 | 59 |
| 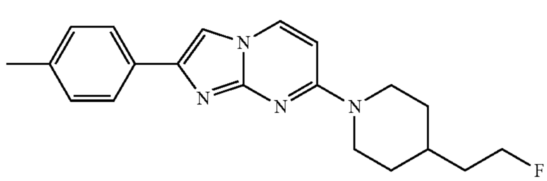 [SMILES: Cc1ccc(-c2cn3ccc(N4CCC(CCF)CC4)nc3n2)cc1] | 7-[4-(2-Fluoroethyl)piperidin-1-yl]-2-(4-methylphenyl)imidazo[1,2-a]pyrimidine | | 15 | 60 |
| 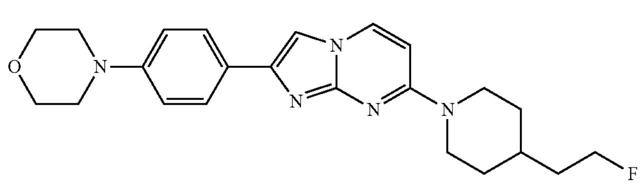 [SMILES: FCCC1CCN(c2ccn3cc(-c4ccc(N5CCOCC5)cc4)nc3n2)CC1] | 4-[4-[7-[4-(2-Fluoroethyl)piperidin-1-yl]imidazo[1,2-a]pyrimidin-2-yl]phenyl]morpholine | | 10 | 61 |

TABLE-continued

I

| Structure | Name | % displacement of [³H]T808 (10 nM) at | | Expl. |
|---|---|---|---|---|
| | | 1 uM | 10 nM | |
| 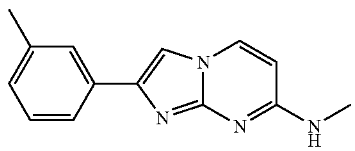 [SMILES: CNc1ccn2cc(-c3cccc(C)c3)nc2n1] | N-Methyl-2-(3-methylphenyl)imidazo[1,2-a]pyrimidin-7-amine | | 48 | 62 |
| 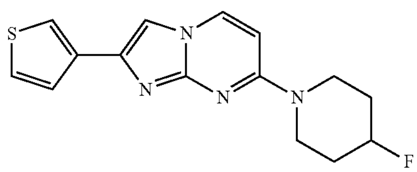 [SMILES: FC1CCN(c2ccn3cc(-c4ccsc4)nc3n2)CC1] | 7-(4-Fluoropiperidin-1-yl)-2-thiophen-3-ylimidazo[1,2-a]pyrimidine | 70 | | 63 |
| 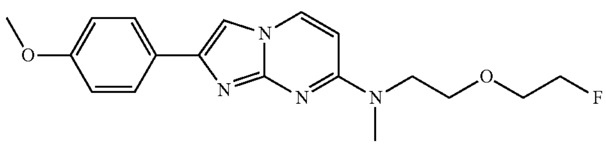 [SMILES: COc1ccc(-c2cn3ccc(N(C)CCOCCF)nc3n2)cc1] | N-[2-(2-Fluoroethoxy)ethyl]-2-(4-methoxyphenyl)-N-methylimidazo[1,2-a]pyrimidin-7-amine | | 15 | 64 |
| 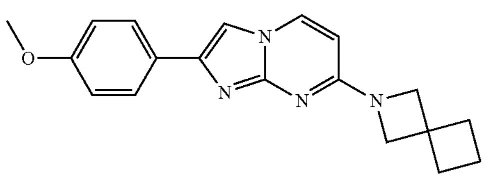 [SMILES: COc1ccc(-c2cn3ccc(N4CC5(CCC5)C4)nc3n2)cc1] | 7-(2-Azaspiro[3.3]heptan-2-yl)-2-(4-methoxyphenyl)imidazo[1,2-a]pyrimidine | | 11 | 65 |
| 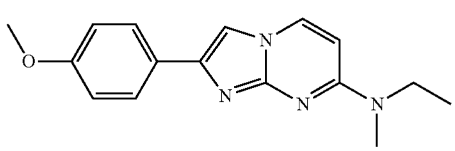 [SMILES: CCN(C)c1ccn2cc(-c3ccc(OC)cc3)nc2n1] | N-Ethyl-2-(4-methoxyphenyl)-N-methylimidazo[1,2-a]pyrimidin-7-amine | | 34 | 66 |
| 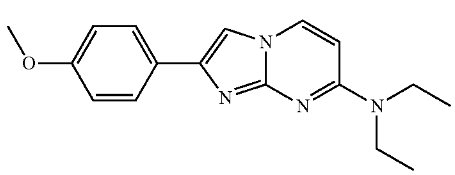 [SMILES: CCN(CC)c1ccn2cc(-c3ccc(OC)cc3)nc2n1] | N,N-Diethyl-2-(4-methoxyphenyl)imidazo[1,2-a]pyrimidin-7-amine | | 19 | 67 |
| 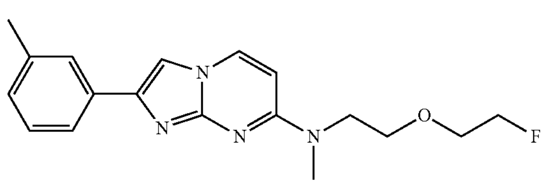 [SMILES: Cc1cccc(-c2cn3ccc(N(C)CCOCCF)nc3n2)c1] | N-[2-(2-Fluoroethoxy)ethyl]-N-methyl-2-(3-methylphenyl)imidazo[1,2-a]pyrimidin-7-amine | | 14 | 68 |

TABLE-continued

I

| Structure | Name | % displacement of [³H]T808 (10 nM) at | | Expl. |
|---|---|---|---|---|
| | | 1 uM | 10 nM | |
| 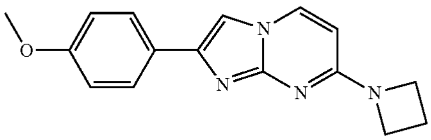 [SMILES: COc1ccc(-c2cn3ccc(N4CCC4)nc3n2)cc1] | 7-(Azetidin-1-yl)-2-(4-methoxyphenyl)imidazo[1,2-a]pyrimidine | | 40 | 69 |
| 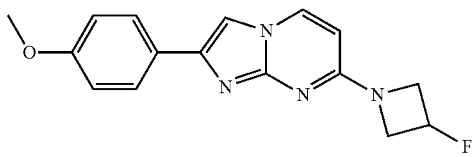 [SMILES: COc1ccc(-c2cn3ccc(N4CC(F)C4)nc3n2)cc1] | 7-(3-Fluoroazetidin-1-yl)-2-(4-methoxyphenyl)imidazo[1,2-a]pyrimidine | | 25 | 70 |
| 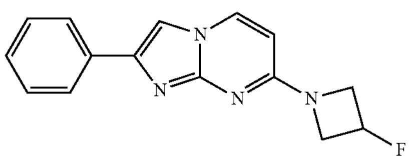 [SMILES: FC1CN(c2ccn3cc(-c4ccccc4)nc3n2)C1] | 7-(3-Fluoroazetidin-1-yl)-2-phenylimidazo[1,2-a]pyrimidine | | 18 | 71 |
| 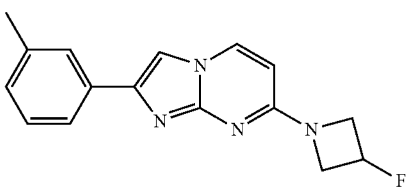 [SMILES: Cc1cccc(-c2cn3ccc(N4CC(F)C4)nc3n2)c1] | 7-(3-Fluoroazetidin-1-yl)-2-(3-methylphenyl)imidazo[1,2-a]pyrimidine | | 18 | 72 |
| 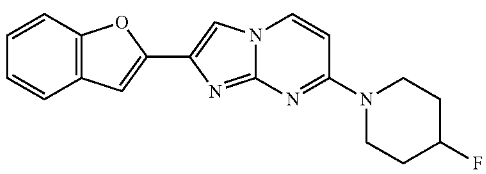 [SMILES: FC1CCN(c2ccn3cc(-c4cc5ccccc5o4)nc3n2)CC1] | 2-(1-Benzofuran-2-yl)-7-(4-fluoropiperidin-1-yl)imidazo[1,2-a]pyrimidine | | 19 | 73 |
| 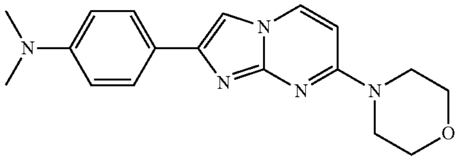 [SMILES: CN(C)c1ccc(-c2cn3ccc(N4CCOCC4)nc3n2)cc1] | N,N-Dimethyl-4-(7-morpholin-4-ylimidazo[1,2-a]pyrimidin-2-yl)aniline | | 16 | 74 |
| 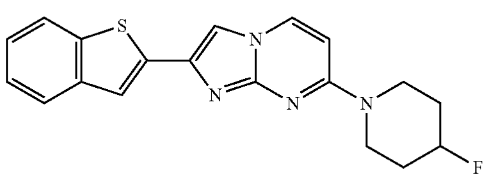 | 2-(1-Benzothiophen-2-yl)-7-(4-fluoropiperidin-1-yl)imidazo[1,2-a]pyrimidine | | 18 | 75 |

TABLE-continued

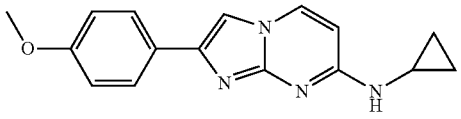 [SMILES: COc1ccc(-c2cn3ccc(NC4CC4)nc3n2)cc1]

I

| Structure | Name | % displacement of [³H]T808 (10 nM) at | | Expl. |
|---|---|---|---|---|
| | | 1 uM | 10 nM | |
| 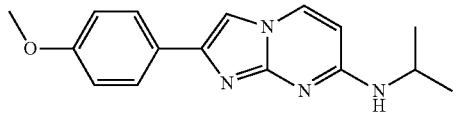 [SMILES: COc1ccc(-c2cn3ccc(NC(C)C)nc3n2)cc1] | N-Cyclopropyl-2-(4-methoxyphenyl)imidazo[1,2-a]pyrimidin-7-amine | | 43 | 76 |
| 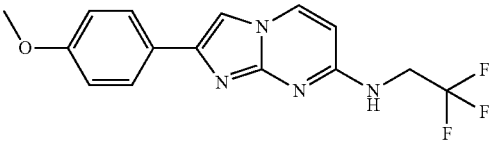 [SMILES: COc1ccc(-c2cn3ccc(NCC(F)(F)F)nc3n2)cc1] | N-Isopropyl-2-(4-methoxy-phenyl)-imidazo[1,2-a]pyrimidin-7-amine | | 15 | 77 |
| 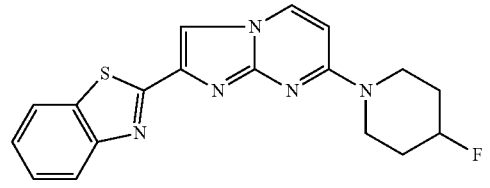 [SMILES: FC1CCN(c2ccn3cc(-c4nc5ccccc5s4)nc3n2)CC1] | 2-(4-Methoxyphenyl)-N-(2,2,2-triflurooethyl)imidazo[1,2-a]pyrimidin-7-amine | | 8 | 78 |
| 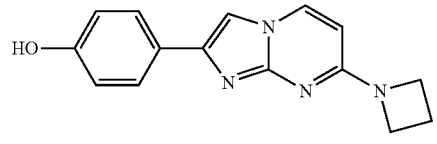 | 2-[7-(4-Fluoropiperidin-1-yl)imidazo[1,2-a]pyrimidin-2-yl]-1,3-benzothiazole | | 12 | 79 |
| 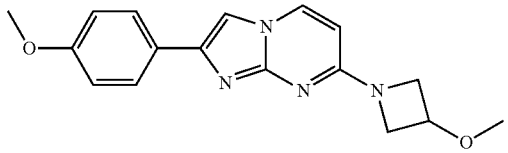 | 4-[7-(Azetidin-1-yl)imidazo[1,2-a]pyrimidin-2-yl]phenol | | 25 | 80 |
| 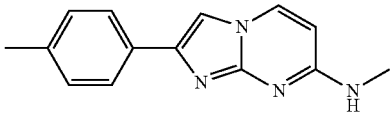 | 7-(3-Methoxyazetidin-1-yl)-1-(4-methoxyphenyl)imidazo[1,2-a]pyrimidine | | 16 | 81 |
| 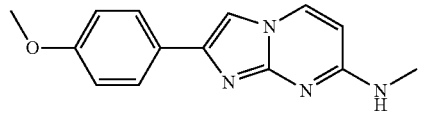 | N-Methyl-2-(4-methylphenyl)imidazo[1,2-a]pyrimidin-7-amine | | 38 | 82 |
| 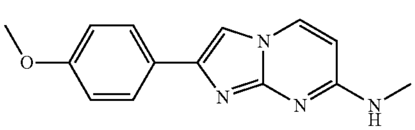 | 2-(4-Methoxyphenyl)-N-methylimidazo[1,2-a]pyrimidin-7-amine | | 41 | 83 |

TABLE-continued

I

| Structure | Name | % displacement of [³H]T808 (10 nM) at 1 uM | % displacement of [³H]T808 (10 nM) at 10 nM | Expl. |
|---|---|---|---|---|
| 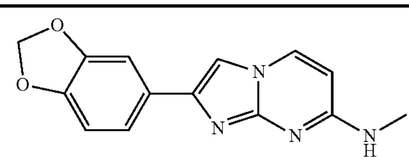 | 2-(1,3-Benzodioxol-5-yl)-N-methylimidazo[1,2-a]pyrimidin-7-amine | 28 | | 84 |
| 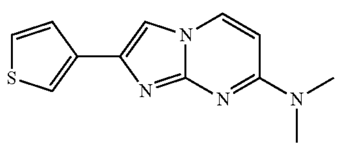 [SMILES: CN(C)c1ccn2cc(-c3ccsc3)nc2n1] | N,N-Dimethyl-2-thiophen-3-ylimidazo[1,2-a]pyrimidin-7-amine | 35 | | 85 |
| 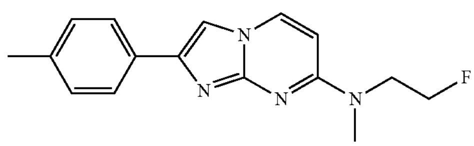 [SMILES: Cc1ccc(-c2cn3ccc(N(C)CCF)nc3n2)cc1] | N-(2-Fluoroethyl)-N-methyl-2-(4-methylphenyl)imidazo[1,2-a]pyrimidin-7-amine | 16 | | 86 |
| 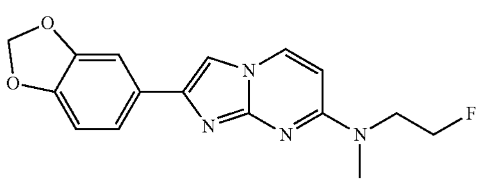 [SMILES: CN(CCF)c1ccn2cc(-c3ccc4c(c3)OCO4)nc2n1] | 2-(1,3-Benzodioxol-5-yl)-N-(2-fluoroethyl)-N-methylimidazo[1,2-a]pyrimidin-7-amine | 15 | | 87 |
| 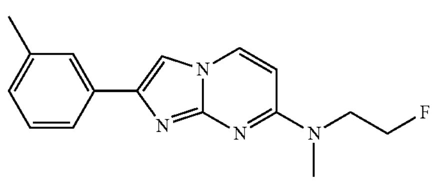 [SMILES: Cc1cccc(-c2cn3ccc(N(C)CCF)nc3n2)c1] | N-(2-Fluoroethyl)-N-methyl-2-(3-methylphenyl)imidazo[1,2-a]pyrimidin-7-amine | 22 | | 88 |
| 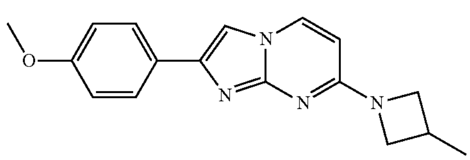 | 2-(4-Methoxyphenyl)-7-(3-methylazetidin-1-yl)imidazo[1,2-a]pyrimidine | 20 | | 89 |
| 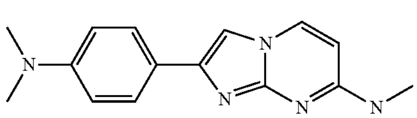 | 2-[4-(Dimethylamino)phenyl]-N-methylimidazo[1,2-a]pyrimidin-7-amine | 38 | | 90 |
| 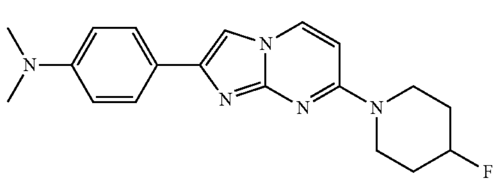 [SMILES: CN(C)c1ccc(-c2cn3ccc(N4CCC(F)CC4)nc3n2)cc1] | 4-[7-(4-Fluoropiperidin-1-yl)imidazo[1,2-a]pyrimidin-2-yl]-N,N-dimethylaniline | 15 | | 91 |

TABLE-continued

Structure I with R1, R2 on phenyl and R3, R4 on amine of imidazo[1,2-a]pyridine core.

| Structure | Name | % displacement of [³H]T808 (10 nM) at 1 uM | % displacement of [³H]T808 (10 nM) at 10 nM | Expl. |
|---|---|---|---|---|
| 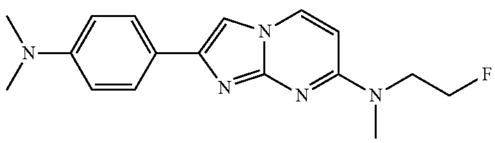 [SMILES: CN(C)c1ccc(-c2cn3ccc(N(C)CCF)nc3n2)cc1] | 2-[4-(Dimethylamino)phenyl]-N-(2-fluoroethyl)-N-methylimidazo[1,2-a]pyrimidin-7-amine | | 27 | 92 |
| 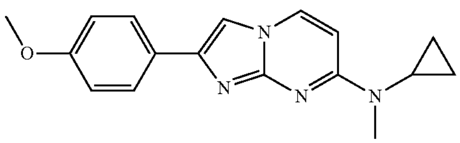 [SMILES: COc1ccc(-c2cn3ccc(N(C)C4CC4)nc3n2)cc1] | N-Cyclopropyl-2-(4-methoxyphenyl)-N-methylimidazo[1,2-a]pyrimidin-7-amine | | 42 | 93 |
| 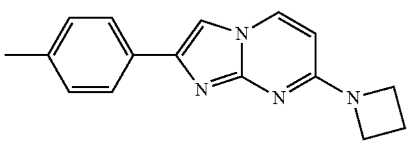 [SMILES: Cc1ccc(-c2cn3ccc(N4CCC4)nc3n2)cc1] | 7-(Azetidin-1-yl)-2-(4-methylphenyl)imidazo[1,2-a]pyrimidine | | 15 | 94 |
| 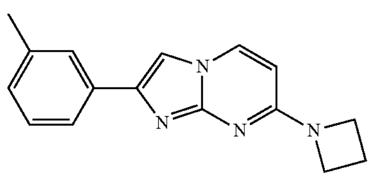 [SMILES: Cc1cccc(-c2cn3ccc(N4CCC4)nc3n2)c1] | 7-(Azetidin-1-yl)-2-(3-methylphenyl)imidazo[1,2-a]pyrimidine | | 38 | 95 |
| 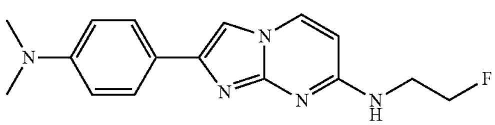 [SMILES: CN(C)c1ccc(-c2cn3ccc(NCCF)nc3n2)cc1] | 2-[4-(Dimethylamino)phenyl]-N-(2-fluoroethyl)imidazo[1,2-a]pyrimidin-7-amine | | 34 | 96 |
| 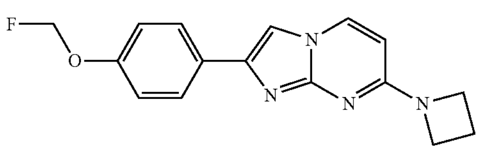 [SMILES: FCOc1ccc(-c2cn3ccc(N4CCC4)nc3n2)cc1] | 7-(Azetidin-1-yl)-2-[4-fluoromethoxy)phenyl]imidazo[1,2-a]pyrimidine | | 30 | 97 |
| 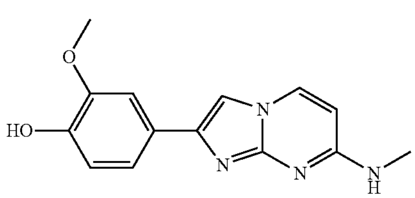 [SMILES: CNc1ccn2cc(-c3ccc(O)c(OC)c3)nc2n1] | 2-Methoxy-4-[7-(methylamino)imidazo[1,2-a]pyrimidin-2-yl]phenol | | 18 | 98 |
| 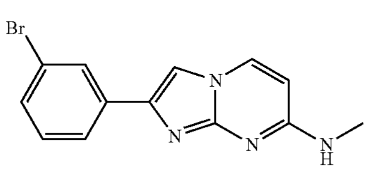 [SMILES: CNc1ccn2cc(-c3cccc(Br)c3)nc2n1] | 2-(3-Bromophenyl)-N-methylimidazo[1,2-a]pyrimidin-7-amine | | 27 | 99 |

TABLE-continued

I

| Structure | Name | % displacement of [³H]T808 (10 nM) at | | Expl. |
|---|---|---|---|---|
| | | 1 uM | 10 nM | |
| 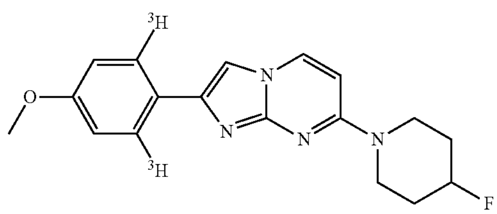 [SMILES: [3H]c1cc(OC)cc([3H])c1-c1cn2ccc(N3CCC(F)CC3)nc2n1] | 7-(4-fluoropiperidin-1-yl)-2-(4-methoxy-2,6-ditritiophenyl)imidazo[1,2-a]pyrimidine | | | 100 |
| 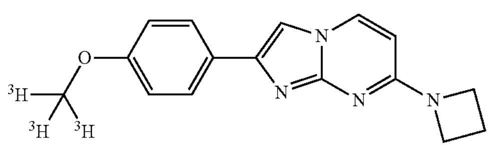 [SMILES: [3H]C([3H])([3H])Oc1ccc(-c2cn3ccc(N4CCC4)nc3n2)cc1] | 7-(Azetidin-1-yl)-2-[4-(tritritiomethoxy)phenyl]imidazo[1,2-a]pyrimidine | | | 101 |
| 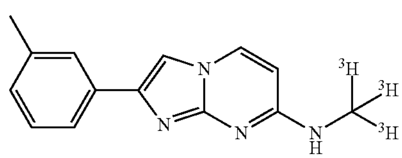 [SMILES: [3H]C([3H])([3H])Nc1ccn2cc(-c3cccc(C)c3)nc2n1] | 2-(3-Methylphenyl)-N-(tritritiomethyl)imidazo[1,2-a]pyrimidine-7-amine | | | 102 |
| | N-[¹¹C]Methyl-2-(m-tolyl)imidazo[1,2-a]pyrimidin-7-amine | | | 103 |
| | N-Cyclopropyl-2-(4-[¹¹C]methoxyphenyl)imidazo[1,2-a]pyrimidin-7-amine | | | 104 |
| | 2-[4-(2-[¹⁸F]Fluoroethoxy)phenyl]-N-methyl-imidazo[1,2-a]pyrimidin-7-amine | | | 105 |
| 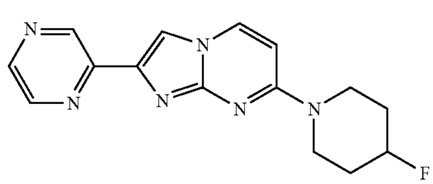 [SMILES: FC1CCN(c2ccn3cc(-c4cnccn4)nc3n2)CC1] | 7-(4-Fluoropiperidin-1-yl)-2-(pyrazin-2-yl)imidazo[1,2-a]pyrimidine | | 20 | 106 |

TABLE-continued

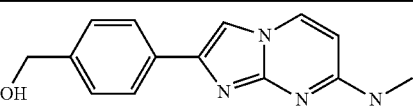

|  |  | % displacement of [³H]T808 (10 nM) at | | |
|---|---|---|---|---|
| Structure | Name | 1 uM | 10 nM | Expl. |
| 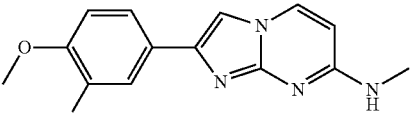 | [4-[7-(Methylamino)imidazo[1,2-a]pyrimidin-2-yl]phenyl]methanol |  | 23 | 107 |
| 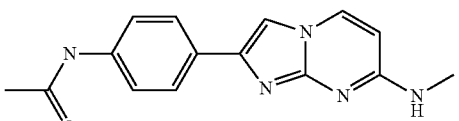 | 2-(3-Fluoro-4-methoxyphenyl)-N-methylimidazo[1,2-a]pyrimidin-7-amine |  | 36 | 108 |
| 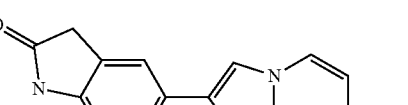 | N-(4-(7-(Methylamino)imidazo[1,2-a]pyrimidin-2-yl)phenyl)acetamide |  | 30 | 109 |
| 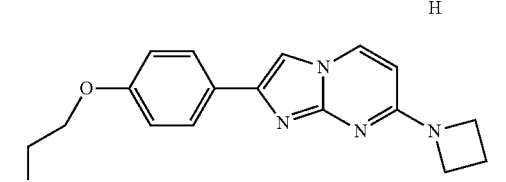 | 5-(7-(methylamino)imidazo[1,2-a]pyrimidin-2-yl)indolin-2-one |  | 18 | 110 |
| 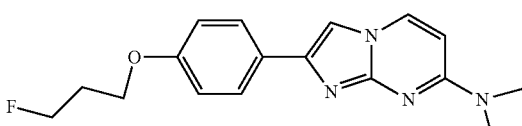 | 7-(Azetidin-1-yl)-2-(4-(2-fluoroethoxy)phenyl)imidazo[1,2-a]pyrimidine |  | 25 | 111 |
| 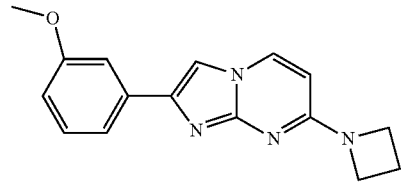 [SMILES: COc1cccc(-c2cn3ccc(N4CCC4)nc3n2)c1] | 7-(Azetidin-1-yl)-2-(4-(3-fluoropropoxy)phenyl)imidazo[1,2-a]pyrimidine |  | 15 | 112 |
| 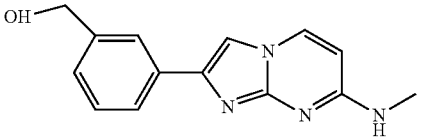 [SMILES: CNc1ccn2cc(-c3cccc(CO)c3)nc2n1] | 7-(azetidin-1-yl)-2-(3-methoxyphenyl)imidazo[1,2-a]pyrimdine |  | 36 | 113 |
|  | [3-[7-(Methylamino)imidazo[1,2-a]pyrimidin-2-yl]phenyl]methanol |  | 11 | 114 |

TABLE-continued

I

| Structure | Name | % displacement of [³H]T808 (10 nM) at | | Expl. |
|---|---|---|---|---|
| | | 1 uM | 10 nM | |
| 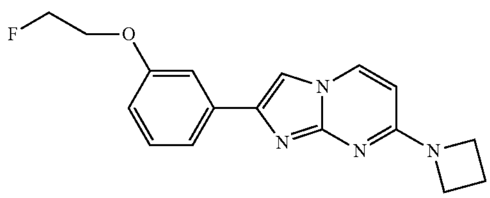 [SMILES: FCCOc1cccc(-c2cn3ccc(N4CCC4)nc3n2)c1] | 7-(Azetidin-1-yl)-2-(3-(2-fluoroethoxy)phenyl)imidazo[1,-2-a]pyrimidine | | 5 | 115 |
| 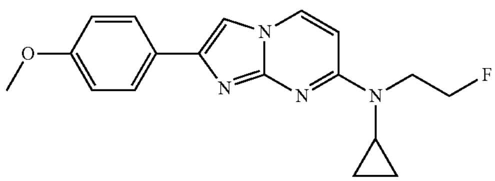 [SMILES: COc1ccc(-c2cn3ccc(N(CCF)C4CC4)nc3n2)cc1] | N-Cyclopropyl-N-(2-fluoroethyl)-2-(4-methoxyphenyl)imidazo[1,2-a]pyrimidin-7-amine | | 9 | 116 |
| 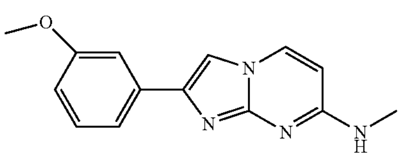 | 2-(3-Methoxyphenyl)-N-methylimidazo[1,2-a]pyrimidin-7-amine | | 40 | 117 |
| 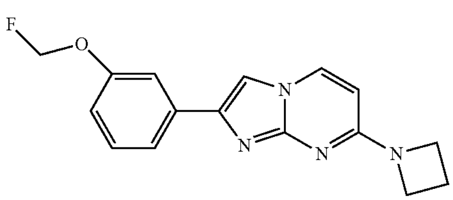 [SMILES: FCOc1cccc(-c2cn3ccc(N4CCC4)nc3n2)c1] | 7-(Azetidin-1-yl)-2-(3-(fluoromethoxy)phenyl)imidazo[1,2-a]pyrimidine | | 23 | 118 |
| 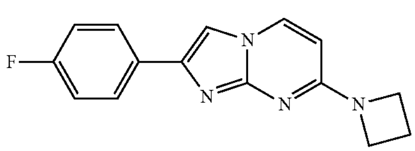 [SMILES: Fc1ccc(-c2cn3ccc(N4CCC4)nc3n2)cc1] | 7-(Azetidin-1-yl)-2-(4-fluoropehnyl)imidazo[1,2-a]pyrimidine | | 22 | 119 |
| 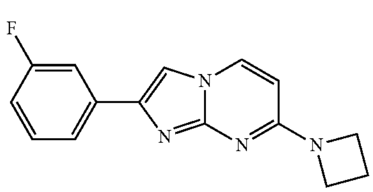 [SMILES: Fc1cccc(-c2cn3ccc(N4CCC4)nc3n2)c1] | 7-(Azetidin-1-yl)-2-(3-fluorophenyl)imidazo[1,2-a]pyrimidine | | 22 | 120 |

TABLE-continued

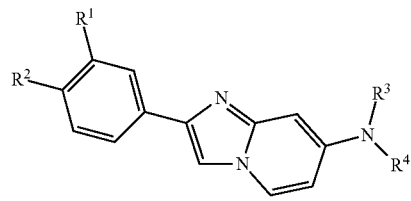

I

| Structure | Name | % displacement of [³H]T808 (10 nM) at | | Expl. |
|---|---|---|---|---|
| | | 1 uM | 10 nM | |
| 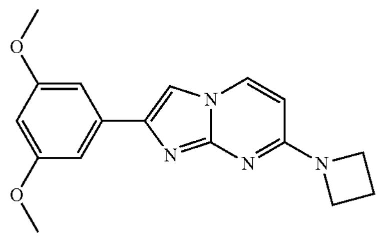 [SMILES: COc1cc(OC)cc(-c2cn3ccc(N4CCC4)nc3n2)c1] | 7-(Azetidin-1-yl)-2-(3,5-diemthoxyphenyl)imidazo[1,2-a]pyrimidine | | 5 | 121 |
| 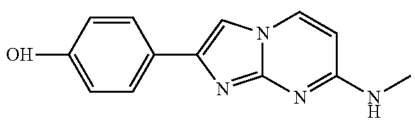 [SMILES: CNc1ccn2cc(-c3ccc(O)cc3)nc2n1] | 4-(7-(Methylamino)imidazo[1,2-a]pyrimidin-2-yl)phenol | | 32 | 122 |
| 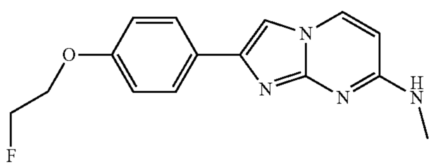 [SMILES: CNc1ccn2cc(-c3ccc(OCCF)cc3)nc2n1] | 2-(4-(2-Fluoroethoxy)phenyl)-N-methylimidazo[1,2-a]pyrimidin-7-amine | | 43 | 123 |
| 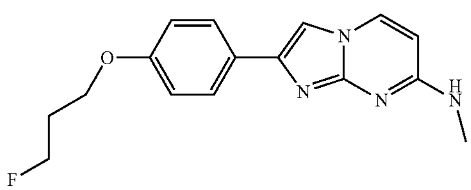 [SMILES: CNc1ccn2cc(-c3ccc(OCCCF)cc3)nc2n1] | 2-(4-(3-Fluoropropoxy)phenyl)-N-methylimidazo[1,2-a]pyrimidin-7-amine | | 40 | 124 |
| 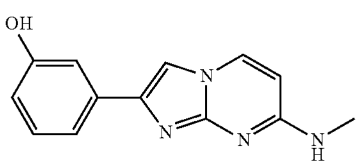 [SMILES: CNc1ccn2cc(-c3cccc(O)c3)nc2n1] | 3-(7-(Methylamino)imidazo[1,2-a]pyrimidin-2-yl)phenol | | 16 | 125 |
| 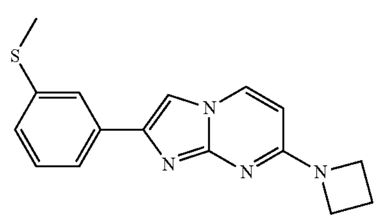 [SMILES: CSc1cccc(-c2cn3ccc(N4CCC4)nc3n2)c1] | 7-(Azetidin-1-yl)-2-(3-(methylthio)phenyl)imidazo[1,2-a]pyrimidine | | 15 | 126 |

TABLE-continued

I

| Structure | Name | % displacement of [³H]T808 (10 nM) at | | Expl. |
|---|---|---|---|---|
| | | 1 uM | 10 nM | |
| 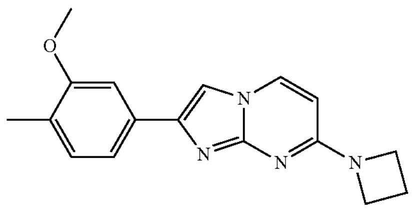 [SMILES: COc1cc(-c2cn3ccc(N4CCC4)nc3n2)ccc1C] | 7-(Azetidin-1-yl)-2-(3-methoxy-4-methylphenyl)imidazo[1,2-a]pyrimidine | | 11 | 127 |
| 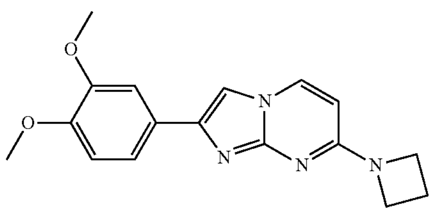 [SMILES: COc1ccc(-c2cn3ccc(N4CCC4)nc3n2)cc1OC] | 7-(Azetidin-1-yl)-2-(3,4-dimethoxyphenyl)imidazo[1,2-a]pyrimidine | | 15 | 128 |
| 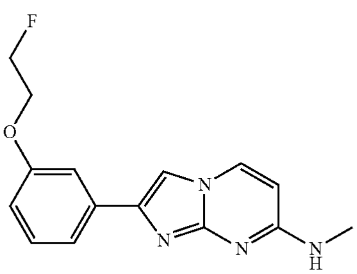 [SMILES: CNc1ccn2cc(-c3cccc(OCCF)c3)nc2n1] | 2-(3-(2-Fluoroethoxy)phenyl)-N-methylimidazo[1,2-a]pyrimidin-7-amine | | 16 | 129 |
| 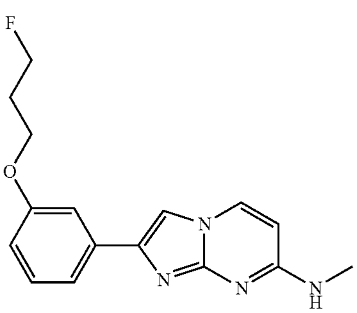 [SMILES: CNc1ccn2cc(-c3cccc(OCCCF)c3)nc2n1] | 2-(3-(3-Fluoropropoxy)phenyl)-N-methylimidazo[1,2-a]pyrimidin-7-amine | | 12 | 130 |
| 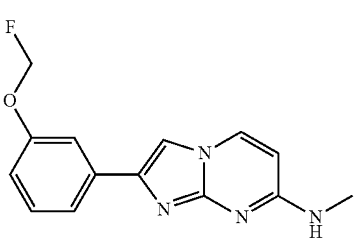 [SMILES: CNc1ccn2cc(-c3cccc(OCF)c3)nc2n1] | 2-(3-(Fluoromethxoy)phenyl)-N-methylimidazo[1,2-a]pyrimidin-7-amine | | 33 | 131 |

TABLE-continued

I

| Structure | Name | % displacement of [³H]T808 (10 nM) at | | Expl. |
|---|---|---|---|---|
| | | 1 uM | 10 nM | |
| 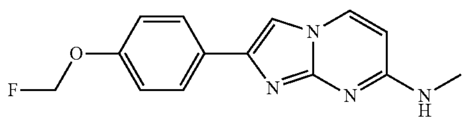 | 2-(4-(Fluoromethoxy)phenyl)-N-methylimidazo[1,2-a]pyrimidin-7-amine | 36 | | 132 |
| 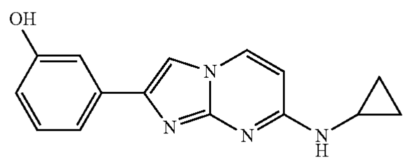 [SMILES: Oc1cccc(-c2cn3ccc(NC4CC4)nc3n2)c1] | 3-(7-(Cyclopropylamino)imidazo[1,2-a]pyrimidin-2-yl)phenol | 14 | | 133 |
| 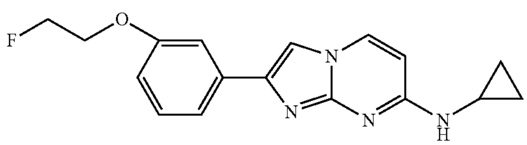 [SMILES: FCCOc1cccc(-c2cn3ccc(NC4CC4)nc3n2)c1] | N-Cyclopropyl-2-(3-(2-fluoroethoxy)phenyl)imidazo[1,2-a]pyrimidin-7-amine | 6 | | 134 |
| 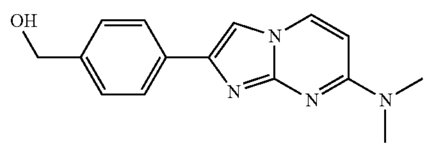 [SMILES: CN(C)c1ccn2cc(-c3ccc(CO)cc3)nc2n1] | [4-[7-(Dimethylamino)imidazo[1,2-a]pyrimidin-2-yl]phenyl]methanol | 18 | | 135 |
| 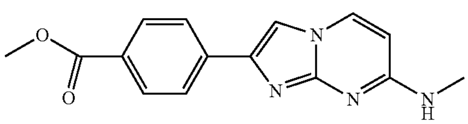 | Methyl 4-[7-(methylamino)imidazo[1,2-a]pyrimidin-2-yl]benzoate | 27 | | 136 |
| 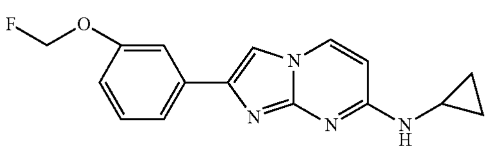 [SMILES: FCOc1cccc(-c2cn3ccc(NC4CC4)nc3n2)c1] | N-Cyclopropyl-2-(3-(fluoromethoxy)phenyl)imidazo[1,2-a]pyrimidin-7-amine | 18 | | 137 |
| 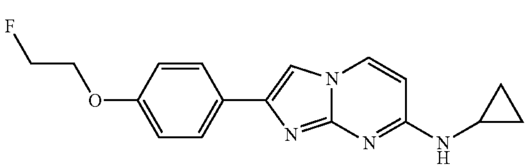 [SMILES: FCCOc1ccc(-c2cn3ccc(NC4CC4)nc3n2)cc1] | N-Cyclopropyl-2-(4-(2-fluoroethoxy)phenyl)imidazo[1,2-a]pyrimidin-7-amine | 20 | | 138 |
| 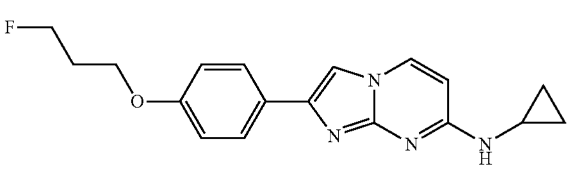 [SMILES: FCCCOc1ccc(-c2cn3ccc(NC4CC4)nc3n2)cc1] | N-Cyclopropyl-2-(4-(3-fluoropropoxy)phenyl)imidazo[1,2-a]pyrimidin-7-amine | 22 | | 139 |

TABLE-continued
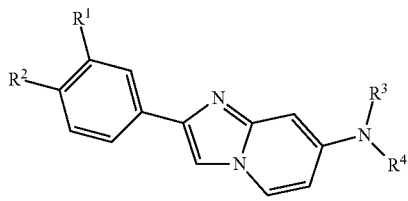
I
| Structure | Name | % displacement of [³H]T808 (10 nM) at | | Expl. |
|---|---|---|---|---|
| | | 1 uM | 10 nM | |
| 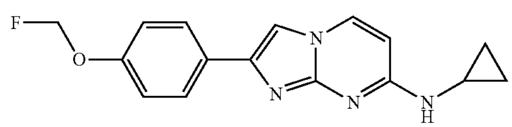 [SMILES: FCOc1ccc(-c2cn3ccc(NC4CC4)nc3n2)cc1] | N-Cyclopropyl-2-(4-(fluoromethoxy)phenyl)imidazo[1,2-a]pyrimidin-7-amine | | 11 | 140 |
| 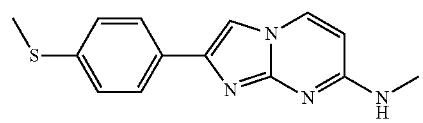 | N-methyl-2-(4-(methylthio)phenyl)imidazo[1,2-a]pyrimidin-7-amine | | 34 | 141 |
| 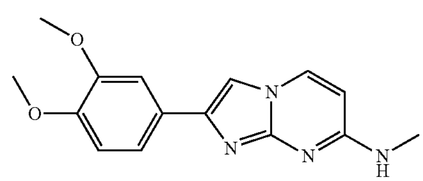 | 2-(3,4-dimethoxyphenyl)-N-methylimidazo[1,2-a]pyrimidin-7-amine | | 21 | 142 |
| 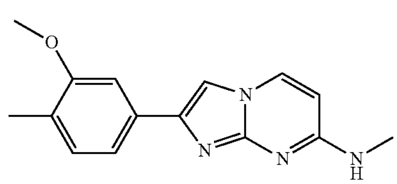 | 2-(3-Methoxy-4-methylphenyl)-N-methylimidazo[1,2-a]pyrimidin-7-amine | | 21 | 143 |
| 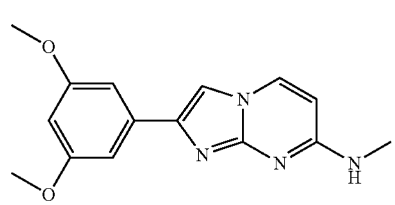 | 2-(3,5-dimethoxyphenyl)-N-methylimidazo[1,2-a]pyrimidin-7-amine | | 14 | 144 |

EXAMPLES

Abbreviations Used:
h—hour(s)
min—minute(s)

Example 1

N-Methyl-2-phenylimidazo[1,2-a]pyrimidin-7-amine

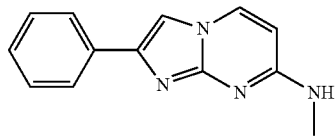 [SMILES: CNc1ccn2cc(-c3ccccc3)nc2n1]

Step 1: N4-Methylpyrimidine-2,4-diamine

To a yellow solution of 4-chloropyrimidin-2-amine (2.00 g, 15.4 mmol) in N-methyl-2-pyrrolidinone (12 mL) were added under an atmosphere of nitrogen methanamine hydrochloride (1.04 g, 15.4 mmol) and potassium carbonate (4.27 g, 30.9 mmol). The reaction mixture was stirred at 120° C. for 2 h. The reaction mixture was concentrated in vacuum and the crude yellow oil was purified by flash chromatography (using silica gel amine phase and a dichloromethane/methanol/ammonia gradient). The obtained yellow oil was triturated with tert. butyl methylether (40 mL) for 15 min to yield the title compound after high vacuum drying for 4 h as light yellow solid (0.76 g, 40%).
MS: m/z 125.2 (M+H)$^+$

Step 2: N-Methyl-2-phenylimidazo[1,2-a]pyrimidin-7-amine

A yellow suspension of N4-methylpyrimidine-2,4-diamine (50 mg, 403 µmol) and 2-bromo-1-phenylethanone (120 mg, 604 µmol) in acetone (2.75 mL) was stirred at 65° C. overnight. The off-white suspension was filtered and washed with water (~1 mL) and acetone (~1 mL). The solid precipitate was suspended into water (1 mL) and ammoniumhydroxide (25%, 0.9 mL). The suspension was stirred for 10 min at room temperature, filtered again and washed with water to yield after high vacuum drying for 4 h the title compound as light red solid (41 mg, 45%).
MS: m/z 225.5 (M+H)$^+$

Example 2

7-(4-Fluoropiperidin-1-yl)-2-phenylimidazo[1,2-a]pyrimidine

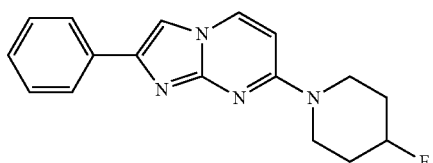

Step 1: 4-(4-Fluoropiperidin-1-yl)pyrimidin-2-amine

A mixture of 4-fluoropiperidine hydrochloride (4.9 g, 35.1 mmol), 4-chloropyrimidin-2-amine (5.00 g, 38.6 mmol) and potassium carbonate (14.6 g, 105 mmol) in N-methyl-2-pyrrolidinone (15.0 mL) was stirred under argon for 2 h at 120° C. The reaction mixture was cooled to room temperature, was poured into NaOH (1 M) and ice and was extracted twice with ethyl acetate. The organic layers were washed with brine, combined, dried over Na$_2$SO$_4$, filtered and the volatiles were evaporated to yield 8.33 g of a light yellow waxy solid. The solid was triturated with tert. butyl methylether (~10 mL) and stirred for 30 min. Then the suspension was filtrated and dried under high vacuum to yield 6.38 g (83%, contains residual N-methyl-2-pyrrolidinone) of a light yellow solid. MS: m/z=197.5 (M+H)$^+$

Step 2: 7-(4-Fluoropiperidin-1-yl)-2-phenyl-2,3-dihydroimidazo[1,2-a]pyrimidin-2-ol A colorless solution of 4-(4-fluoropiperidin-1-yl)pyrimidin-2-amine (89 mg, 454 µmol) and 2-bromo-1-phenylethanone (135 mg, 680 µmol) in acetone was heated under argon to 65° C. and stirred for 6 h. The light yellow suspension was filtered over a glass fiber paper and was washed with acetone (1 mL). Ammoniumhydroxide (25%, 2.5 mL) and water (3.1 mL) were added and the white suspension was filtered over a glass fiber paper and washed with H$_2$O. The product was obtained after drying on high vacuum for 3 h as white solid (78 mg, 58%).
MS: m/z=315.6 (M+H)$^+$

Step 3: 7-(4-Fluoropiperidin-1-yl)-2-phenylimidazo[1,2-a]pyrimidine

To an off-white suspension of 7-(4-fluoropiperidin-1-yl)-2-phenyl-2,3-dihydroimidazo[1,2-a]pyrimidin-2-ol (78 mg, 248 µmol) in toluene (2.6 mL) was added p-toluenesulfonic acid (4.27 mg, 3.99 µl, 24.8 µmol) and the resulting mixture was stirred under argon and heated to 125° C. for 1 h. The light yellow suspension was diluted with little water and ammoniumhydroxide (25%) was added. The resulting suspension was filtered over a glass fiber paper and the product was obtained after drying on high vacuum for 3 h as off-white solid (56 mg, 76%).
MS: m/z=297.5 (M+H)$^+$

Example 3

7-(4-Fluoropiperidin-1-yl)-2-(4-methoxyphenyl)imidazo[1,2-a]pyrimidine

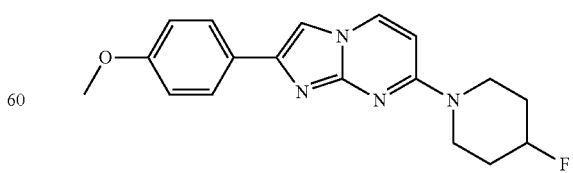

The product was obtained starting from 4-(4-fluoropiperidin-1-yl)pyrimidin-2-amine (85 mg, 433 µmol, example 2, step 1) and 2-bromo-1-(4-methoxyphenyl)ethanone (149 mg, 650 µmol) according to the method described in example 1, step 2 as off-white solid (80 mg, 57%).
MS: m/z=327.5 (M+H)⁺

Example 4

2-(4-Chlorophenyl)-7-(4-fluoropiperidin-1-yl)imidazo[1,2-a]pyrimidine

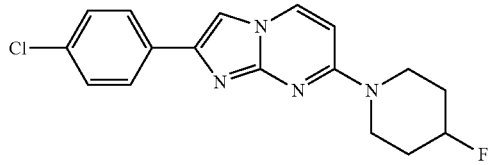 [SMILES: FC1CCN(c2ccn3cc(-c4ccc(Cl)cc4)nc3n2)CC1]

The product was obtained starting from 4-(4-fluoropiperidin-1-yl)pyrimidin-2-amine (85 mg, 433 µmol, example 2, step 1) and 2-bromo-1-(4-chlorophenyl)ethanone (152 mg, 650 µmol) according to the method described in example 1, step 2 as light red solid (80 mg, 56%).
MS: m/z=331.5 (M+H)⁺

Example 5

7-(4-Fluoropiperidin-1-yl)-2-(3-methoxyphenyl)imidazo[1,2-a]pyrimidine

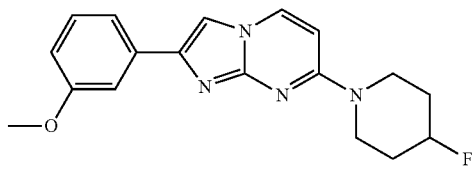 [SMILES: COc1cccc(-c2cn3ccc(N4CCC(F)CC4)nc3n2)c1]

The product was obtained starting from 4-(4-fluoropiperidin-1-yl)pyrimidin-2-amine (85 mg, 433 µmol, example 2, step 1) and 2-bromo-1-(3-methoxyphenyl)ethanone (149 mg, 650 µmol) according to the method described in example 1, step 2 and final purification by flash chromatography (using silica gel amine phase and an heptane/ethyl acetate gradient) as orange foam (76 mg, 51%). MS: m/z=327.5 (M+H)⁺

Example 6

2-(4-Fluorophenyl)-7-(4-fluoropiperidin-1-yl)imidazo[1,2-a]pyrimidine

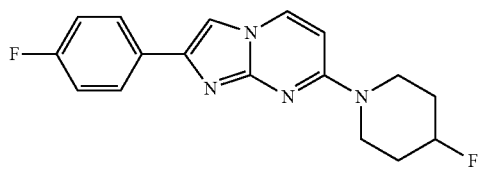 [SMILES: Fc1ccc(-c2cn3ccc(N4CCC(F)CC4)nc3n2)cc1]

Using a microwave tube, a solution of 4-(4-fluoropiperidin-1-yl)pyrimidin-2-amine (90 mg, 459 µmol, example 2, step 1) and 2-bromo-1-(4-fluorophenyl)ethanone (149 mg, 688 µmol) in acetone (2.5 mL) was sealed and heated at 70° C. for 20 h. The reaction mixture was filtered and washed with acetone (~2 mL). To the remaining off white solid was added ammonium hydroxide (25%, 2 mL) and water (3 mL) and the white-grey suspension was filtrated and washed with water (~2 mL). After drying under high vacuum the title compound was obtained as light yellow solid (51 mg, 35%).
MS: m/z=315.5 (M+H)⁺

Example 7

2-(1,3-Benzodioxol-5-yl)-7-(4-fluoropiperidin-1-yl)imidazo[1,2-a]pyrimidine

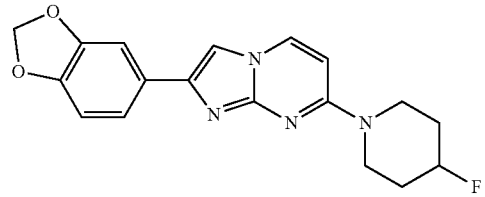 [SMILES: FC1CCN(c2ccn3cc(-c4ccc5c(c4)OCO5)nc3n2)CC1]

The product was obtained starting from 4-(4-fluoropiperidin-1-yl)pyrimidin-2-amine (92 mg, 472 µmol, example 2, step 1) and 1-(benzo[d][1,3]dioxol-5-yl)-2-bromoethanone (172 mg, 709 µmol) according to the method described in example 6 as light yellow solid (129 mg, 79%).
MS: m/z=341.6 (M+H)⁺

Example 8

2-(2,3-Dihydro-1,4-benzodioxin-6-yl)-7-(4-fluoropiperidin-1-yl)imidazo[1,2-a]pyrimidine

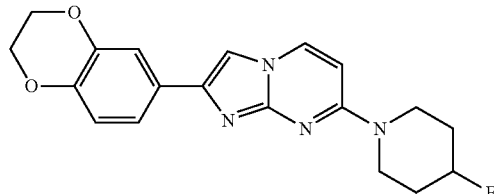

The product was obtained starting from 4-(4-fluoropiperidin-1-yl)pyrimidin-2-amine (93 mg, 477 µmol, example 2, step 1) and 2-bromo-1-(2,3-dihydrobenzo[b][1,4]dioxin-6-yl)ethanone (184 mg, 716 µmol) according to the method described in example 6 as light yellow solid (132 mg, 76%).
MS: m/z=355.5 (M+H)⁺

Example 9

4-[4-[7-(4-Fluoropiperidin-1-yl)imidazo[1,2-a]pyrimidin-2-yl]phenyl]morpholine

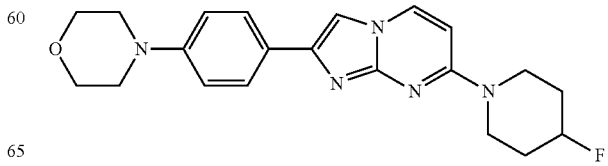

The product was obtained starting from 4-(4-fluoropiperidin-1-yl)pyrimidin-2-amine (91 mg, 463 µmol, example 2, step 1) and 2-bromo-1-(4-morpholinophenyl)ethanone (197 mg, 695 µmol) according to the method described in example 6 as light yellow solid (58 mg, 32%).
MS: m/z=382.5 (M+H)+

Example 10

7-(4-Fluoropiperidin-1-yl)-2-(3-methylphenyl)imidazo[1,2-a]pyrimidine

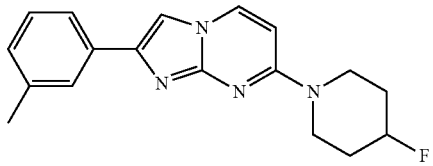

The product was obtained starting from 4-(4-fluoropiperidin-1-yl)pyrimidin-2-amine (90 mg, 459 µmol, example 2, step 1) and 2-bromo-1-m-tolylethanone (147 mg, 688 µmol) according to the method described in example 1, step 2 as light yellow solid (100 mg, 70%).
MS: m/z=311.5 (M+H)+

Example 11

7-(4-Fluoropiperidin-1-yl)-2-(4-methylphenyl)imidazo[1,2-a]pyrimidine

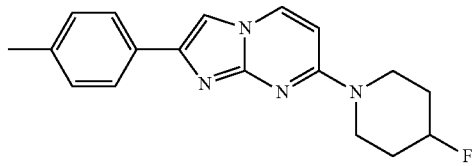 [SMILES: Cc1ccc(-c2cn3ccc(N4CCC(F)CC4)nc3n2)cc1]

The product was obtained starting from 4-(4-fluoropiperidin-1-yl)pyrimidin-2-amine (90 mg, 459 µmol, example 2, step 1) and 2-bromo-1-p-tolylethanone (147 mg, 688 µmol) according to the method described in example 1, step 2 as light yellow solid (107 mg, 75%).
MS: m/z=311.5 (M+H)+

Example 12

2-(2-Fluorophenyl)-7-(4-fluoropiperidin-1-yl)imidazo[1,2-a]pyrimidine

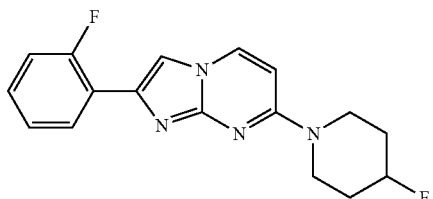

The product was obtained starting from 4-(4-fluoropiperidin-1-yl)pyrimidin-2-amine (102 mg, 514 µmol, example 2, step 1) and 2-bromo-1-(2-fluorophenyl)ethanone (167 mg, 771 µmol) according to the method described in example 6 as light yellow solid (36 mg, 22%).
MS: m/z=315.5 (M+H)+

Example 13

3-[7-(4-Fluoropiperidin-1-yl)imidazo[1,2-a]pyrimidin-2-yl]phenol

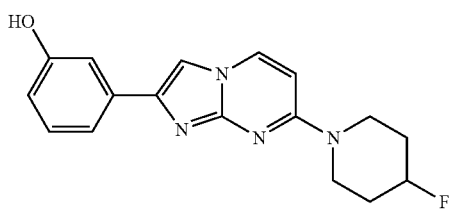 [SMILES: Oc1cccc(-c2cn3ccc(N4CCC(F)CC4)nc3n2)c1]

According to the method described in example 6 and starting from 4-(4-fluoropiperidin-1-yl)pyrimidin-2-amine (96 mg, 491 µmol, example 2, step 1) and 2-bromo-1-(3-hydroxyphenyl)ethanone (158 mg, 736 µmol) an off-white solid was obtained. To the off-white solid (188 mg) was added toluene (2.5 mL) and p-toluenesulfonic acid (12.7 mg, 11.8 µL, 73.6 µmol). The vessel was sealed and heated at 100° C. for 2 h. The reaction mixture was filtered and washed with acetone and water/ammonium hydroxide (9:1 mixture) to yield the product as off-white solid (67 mg, 43%). MS: m/z=313.5 (M+H)+

Example 14

7-(4-Fluoropiperidin-1-yl)-2-(4-pyrrolidin-1-ylphenyl)imidazo[1,2-a]pyrimidine

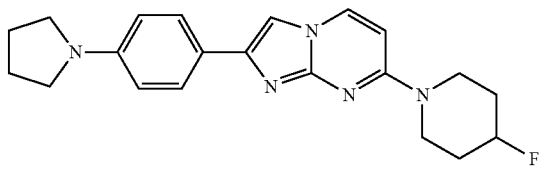 [SMILES: FC1CCN(c2ccn3cc(-c4ccc(N5CCCC5)cc4)nc3n2)CC1]

According to the method described in example 6 and starting from 4-(4-fluoropiperidin-1-yl)pyrimidin-2-amine (90 mg, 459 µmol, example 2, step 1), 2-bromo-1-(4-(pyrrolidin-1-yl)phenyl)ethanone (184 mg, 688 µmol) and p-toluenesulfonic acid (7.9 mg, 7.38 µL, 45.9 µmol) a light yellow solid was obtained. To the light yellow solid (176 mg) was added toluene (2.5 mL) and p-toluenesulfonic acid (7.9 mg, 7.38 µL, 45.9 µmol). The vessel was sealed and heated at 100° C. for 2 h. The reaction mixture was filtered and washed with acetone and water/ammonium hydroxide (9:1 mixture) to yield the crude product. The product was obtained after purification by flash chromatography (using silica gel and a dichloromethane/methanol gradient) as light yellow solid (64 mg, 36%). MS: m/z=366.5 (M+H)+

Example 15

7-(4-Fluoropiperidin-1-yl)-2-[3-(trifluoromethoxy)phenyl]imidazo[1,2-a]pyrimidine

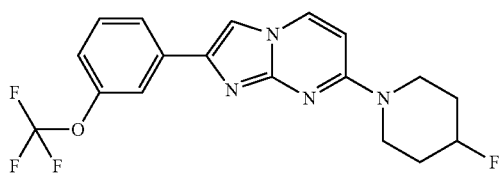 [SMILES: FC1CCN(c2ccn3cc(-c4cccc(OC(F)(F)F)c4)nc3n2)CC1]

The product was obtained starting from 4-(4-fluoropiperidin-1-yl)pyrimidin-2-amine (97 mg, 495 µmol, example 2, step 1) and 2-bromo-1-(3-(trifluoromethoxy)phenyl)ethanone (140 mg, 495 µmol) according to the method described in example 6 and final purification by flash chromatography (using silica gel and a dichloromethane/methanol gradient) as light brown solid (81 mg, 42%). MS: m/z=381.6 (M+H)$^+$

Example 16

2-[3-(Fluoromethoxy)phenyl]-7-pyrrolidin-1-ylimidazo[1,2-a]pyrimidine

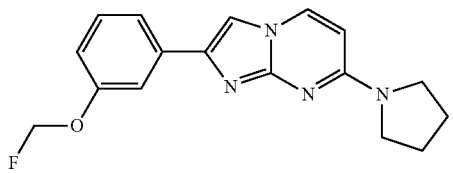 [SMILES: FCOc1cccc(-c2cn3ccc(N4CCCC4)nc3n2)c1]

Step 1: 4-(Pyrrolidin-1-yl)pyrimidin-2-amine

A light yellow suspension of 4-chloropyrimidin-2-amine (5.01 g, 38.7 mmol), pyrrolidine (2.50 g, 2.91 ml, 35.2 mmol) and potassium carbonate (9.72 g, 70.3 mmol) in N-methyl-2-pyrrolidinone (15.0 mL) was stirred under argon at 120° C. for 2 h and at room temperature overnight. The reaction mixture was cooled to room temperature and was poured into NaOH (1 M, 200 mL) and ice. The aqueous layer was extracted with ethyl acetate (200 mL) whereof part of the product precipitated in the water phase. The precipitate was filtered, washed water, triturated with dichloromethane and dried to obtain 3.1 g product as white solid. The separated ethyl acetate phase was dried over MgSO$_4$, filtered and concentrated in vacuum. The resulting light yellow solid was triturated with dichloromethane and dried to obtain 1.1 g product as white solid. The aqueous phase was extracted with dichloromethane (3×100 mL), dried over MgSO$_4$, filtered and concentrated in vacuum. The resulting light yellow solid was triturated with dichloromethane to obtain another 0.52 g product as white solid. The dichloromethane layers were combined, concentrated in vacuum and the product was purified by flash chromatography (using silica gel and a dichloromethane/methanol/ammonia gradient) to yield another 0.46 g product as light yellow. In total 5.18 g (89.7%) of a light yellow solid were obtained.
MS: m/z=165.3 (M+H)$^+$

Step 2: 3-(7-(Pyrrolidin-1-yl)imidazo[1,2-a]pyrimidin-2-yl)phenol

The product was obtained starting from 4-(pyrrolidin-1-yl)pyrimidin-2-amine (300 mg, 1.83 mmol) and 2-bromo-1-(3-hydroxyphenyl)ethanone (589 mg, 2.74 mmol) according to the method described in example 1, step 2 as light yellow solid (460 mg, 90%).
MS: m/z=281.1 (M+H)$^+$

Step 3: 2-[3-(Fluoromethoxy)phenyl]-7-pyrrolidin-1-ylimidazo[1,2-a]pyrimidine To a light yellow solution of 3-(7-(pyrrolidin-1-yl)imidazo[1,2-a]pyrimidin-2-yl)phenol (100 mg, 357 µmol) and fluoromethyl 4-methylbenzenesulfonate (72.9 mg, 357 µmol) in DMF (1.00 mL) was added under argon cesium carbonate (151 mg, 464 µmol). The reaction mixture was heated to 70° C. and stirred for 16 h. The yellow suspension was diluted with water (5 mL) and extracted with ethyl acetate (3×5 mL). The organic layers were combined, washed with brine, dried over MgSO$_4$, filtered and evaporated. The product was obtained after purification by flash chromatography (using silica gel and a dichloromethane/methanol/ammonia gradient) as light yellow solid (52 mg, 46%).
MS: m/z=313.5 (M+H)$^+$

Example 17

2-[3-(2-Fluoroethoxy)phenyl]-7-pyrrolidin-1-ylimidazo[1,2-a]pyrimidine

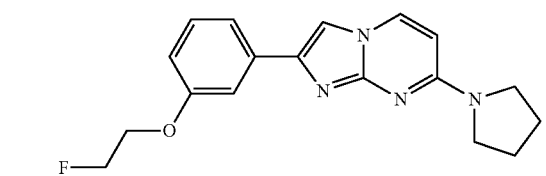 [SMILES: FCCOc1cccc(-c2cn3ccc(N4CCCC4)nc3n2)c1]

The product was obtained starting from 3-(7-(pyrrolidin-1-yl)imidazo[1,2-a]pyrimidin-2-yl)phenol (100 mg, 357 µmol, example 16, step 2) and 1-bromo-2-fluoroethane (45.3 mg, 357 µmol) according to the method described in example 16, step 3 as light yellow solid (57 mg, 49%). MS: m/z=327.6 (M+H)$^+$

Example 18

N,N-Dimethyl-2-phenylimidazo[1,2-a]pyrimidin-7-amine

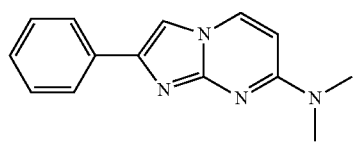 [SMILES: CN(C)c1ccn2cc(-c3ccccc3)nc2n1]

Step 1: N4,N4-Dimethylpyrimidine-2,4-diamine

The product was obtained starting 4-chloropyrimidin-2-amine (3.24 g, 25.0 mmol) and dimethylamine hydrochloride (2.24 g, 27.5 mmol) and potassium carbonate (10.4 g, 75.0 mmol) according to the method described in example 2, step 1 as white solid (1.48 g, 43%).

Step 2: N,N-Dimethyl-2-phenylimidazo[1,2-a]pyrimidin-7-amine

The product was obtained starting from N4,N4-dimethylpyrimidine-2,4-diamine (100 mg, 724 µmol) and 2-bromo-1-phenylethanone (216 mg, 1.09 mmol) according to the method described in example 1, step 2 as light brown solid (97 mg, 56%). MS: m/z=239.1 (M+H)$^+$

Example 19

7-[4-(2-Fluoroethyl)piperazin-1-yl]-2-(4-methoxyphenyl)imidazo[1,2-a]pyrimidine hydrochloride

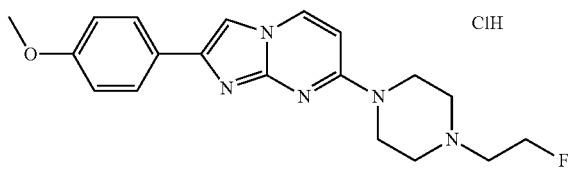 [SMILES: COc1ccc(-c2cn3ccc(N4CCN(CCF)CC4)nc3n2)cc1 ; Cl]

Step 1: 4-(4-(2-Fluoroethyl)piperazin-1-yl)pyrimidin-2-amine

The product was obtained starting from 1-(2-fluoroethyl)piperazine hydrochloride (705 mg, 3.55 mmol), 4-chloropyrimidin-2-amine (506 mg, 3.91 mmol) and potassium carbonate (1.47 g, 10.7 mmol) in N-methyl-2-pyrrolidinone (1.5 mL) according to the method described in example 2, step 1 after overnight heating as light brown solid (642 mg, 79%). MS: m/z=226.6 (M+H)$^+$

Step 2: 7-[4-(2-Fluoroethyl)piperazin-1-yl]-2-(4-methoxyphenyl)imidazo[1,2-a]pyrimidine hydrochloride The crude product was obtained starting from 4-(4-(2-fluoroethyl)piperazin-1-yl)pyrimidin-2-amine (156 mg, 693 µmol) and 2-bromo-1-(4-methoxyphenyl)ethanone (238 mg, 1.04 mmol) according to method described in example 6. The resulting light yellow solid was triturated with heptane. The resulting suspension was filtrated, washed and dried in vacuum to yield 243 mg of a light yellow solid. To this material was added THF (1.00 mL) and HCl (4 M solution in dioxane, 1.73 mL, 6.93 mmol). Stirring was continued at room temperature for 2 h and the suspension was filtrated, washed with THF and dried in high vacuum. To the resulting light yellow solid was added heptane/ethyl acetate (2:1 mixture) and stirring was continued at room temperature for 15 min. The suspension was filtrated and washed with tert. butyl methylether to obtain the product as light yellow solid (141 mg, 42%). MS: m/z=356.2 (M−HCl+H)$^+$

Example 20

7-[4-(2-Fluoroethyl)piperazin-1-yl]-2-(3-methoxyphenyl)imidazo[1,2-a]pyrimidine hydrochloride

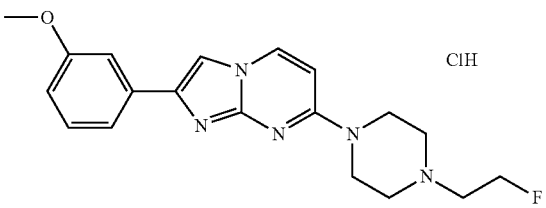 [SMILES: COc1cccc(-c2cn3ccc(N4CCN(CCF)CC4)nc3n2)c1 ; Cl]

The product was obtained starting from 4-(4-(2-fluoroethyl)piperazin-1-yl)pyrimidin-2-amine (151 mg, 670 µmol, example 19, step 1) and 2-bromo-1-(3-methoxyphenyl)ethanone (230 mg, 1.01 mmol) according to method described in example 19, step 2 as light yellow solid (114 mg, 35%).

MS: m/z=356.2 (M−HCl+H)$^+$

Example 21

N-(2-Fluoroethyl)-N-methyl-2-phenylimidazo[1,2-a]pyrimidin-7-amine

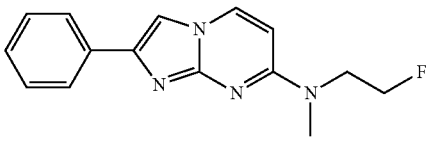 [SMILES: CN(CCF)c1ccn2cc(-c3ccccc3)nc2n1]

Step 1: N4-(2-Fluoroethyl)-N4-methylpyrimidine-2,4-diamine

The product was obtained starting from 4-chloropyrimidin-2-amine (500 mg, 3.86 mmol), 2-fluoro-N-methylethanamine hydrochloride (482 mg, 4.25 mmol) and potassium carbonate (1.6 g, 11.6 mmol) in N-methyl-2-pyrrolidinone (2.5 mL) according to the method described in example 2, step 1 and final purification by flash chromatography (using silica gel and a dichloromethane/methanol gradient) as yellow solid (263 mg, 40%). MS: m/z=171.3 (M+H)$^+$

Step 2: N-(2-Fluoroethyl)-N-methyl-2-phenylimidazo[1,2-a]pyrimidin-7-amine

The product was obtained starting from N4-(2-fluoroethyl)-N4-methylpyrimidine-2,4-diamine (60 mg, 353 µmol) and 2-bromo-1-phenylethanone (105 mg, 529 µmol) according to the method described in example 1, step 2 as light yellow solid (41 mg, 41%). MS: m/z=271.5 (M+H)$^+$

Example 22

N-(2-Fluoroethyl)-2-(3-methoxyphenyl)-N-methyl-imidazo[1,2-a]pyrimidin-7-amine

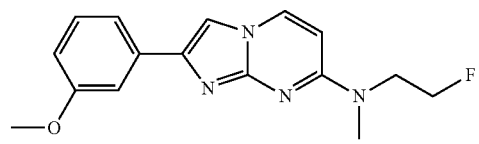 [SMILES: COc1cccc(-c2cn3ccc(N(C)CCF)nc3n2)c1]

The product was obtained starting from N4-(2-fluoroethyl)-N4-methylpyrimidine-2,4-diamine (60 mg, 353 µmol, example 21, step 1) and 2-bromo-1-(3-methoxyphenyl)ethanone (121 mg, 529 µmol) according to the method described in example 1, step 2 as yellow solid (28 mg, 24%). MS: m/z=301.5 (M+H)$^+$

Example 23

N-(2-Fluoroethyl)-2-(4-methoxyphenyl)-N-methyl-imidazo[1,2-a]pyrimidin-7-amine

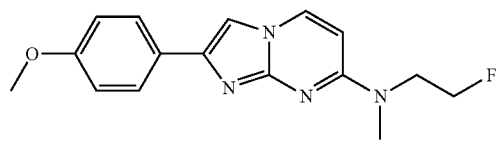 [SMILES: COc1ccc(-c2cn3ccc(N(C)CCF)nc3n2)cc1]

The product was obtained starting from N4-(2-fluoroethyl)-N4-methylpyrimidine-2,4-diamine (85 mg, 499 µmol, example 21, step 1) and 2-bromo-1-(4-methoxyphenyl)ethanone (172 mg, 749 µmol) according to the method described in example 1, step 2 as yellow solid (44 mg, 29%). MS: m/z=301.5 (M+H)$^+$

Example 24

7-[4-(2-Fluoroethyl)piperazin-1-yl]-2-phenylimidazo[1,2-a]pyrimidine hydrochloride

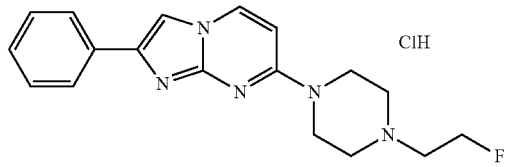

The product was obtained starting from 4-(4-(2-fluoroethyl)piperazin-1-yl)pyrimidin-2-amine (155 mg, 688 µmol, example 19, step 1) and 2-bromo-1-phenylethanone (205 mg, 1.03 mmol) according to method described in example 19, step 2 as off-white solid (57 mg, 18%).

MS: m/z=326.2 (M−HCl+H)$^+$

Example 25

4-[2-(4-Methoxyphenyl)imidazo[1,2-a]pyrimidin-7-yl]morpholine

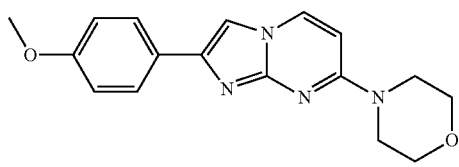

Step 1: 4-Morpholin-4-yl-pyrimidin-2-ylamine

The product was obtained starting from 4-chloro-pyrimidin-2-ylamine (3 g, 23.25 mmol) and morpholine (2.25 mL, 25.6 mmol) according to the method describe in example 49, step 1 as white solid (2.7 g, 64%). MS: m/z=181.0 (M+H)$^+$ Step 2: 4-[2-(4-Methoxyphenyl)imidazo[1,2-a]pyrimidin-7-yl]morpholine The product was obtained starting from 4-morpholin-4-yl-pyrimidin-2-ylamine (350 mg, 1.94 mmol) and 2-bromo-1-(4-methoxy-phenyl)-ethanone (667 mg, 2.91 mmol) according to the method describe in example 49, step 2 as grey solid (240 mg, 40%). MS: m/z=311.2 (M+H)$^+$

Example 26

4-[2-(3-Methylphenyl)imidazo[1,2-a]pyrimidin-7-yl]morpholine

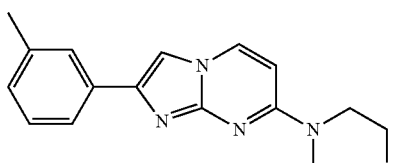

The product was obtained starting from 4-morpholin-4-yl-pyrimidin-2-ylamine (400 mg, 2.22 mmol, example 25, step 1) and 2-bromo-1-m-tolyl-ethanone (709 mg, 3.33 mmol) according to the method describe in example 49, step 2 as off-white solid (65 mg, 10%).

MS: m/z=295.0 (M+H)$^+$

Example 27

4-[2-(3,4-Dimethoxyphenyl)imidazo[1,2-a]pyrimidin-7-yl]morpholine

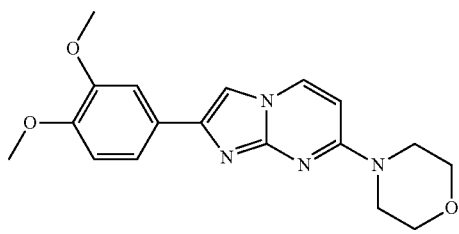 [SMILES: COc1ccc(-c2cn3ccc(N4CCOCC4)nc3n2)cc1OC]

The product was obtained starting from 4-morpholin-4-yl-pyrimidin-2-ylamine (400 mg, 2.22 mmol, example 25, step 1) and 2-bromo-1-(3,4-dimethoxy-phenyl)-ethanone (862 mg, 3.32 mmol) according to the method describe in example 49, step 2 as off-white solid (230 mg, 30%). MS: m/z=341.0 (M+H)+

Example 28

4-(7-Pyrrolidin-1-ylimidazo[1,2-a]pyrimidin-2-yl)phenol

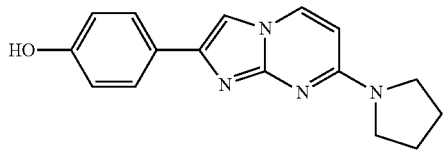 [SMILES: Oc1ccc(-c2cn3ccc(N4CCCC4)nc3n2)cc1]

The product was obtained starting from 4-(pyrrolidin-1-yl)pyrimidin-2-amine (500 mg, 3.04 mmol, example 16, step 1) and 2-bromo-1-(4-hydroxyphenyl)ethanone (982 mg, 4.57 mmol) according to the method described in example 1, step 2 as yellow solid (786 mg, 90%).
MS: m/z=281.5 (M+H)+

Example 29

2-[4-(2-Fluoroethoxy)phenyl]-7-pyrrolidin-1-ylimidazo[1,2-a]pyrimidine

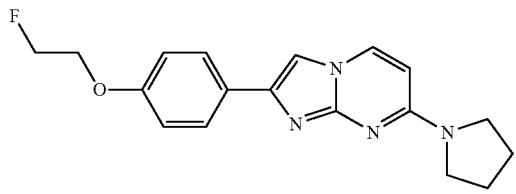 [SMILES: FCCOc1ccc(-c2cn3ccc(N4CCCC4)nc3n2)cc1]

To a light yellow solution of 4-(7-(pyrrolidin-1-yl)imidazo[1,2-a]pyrimidin-2-yl)phenol (100 mg, 357 μmol, example 28) and 1-bromo-2-fluoroethane (45.3 mg, 357 μmol) in DMF (1.00 mL) was added under argon cesium carbonate (151 mg, 464 μmol). The reaction mixture was stirred at 70° C. for 22 h. The brown suspension was diluted with water (5 mL) and extracted with dichloromethane (2×5 mL). The organic layers were combined washed with brine (5 mL), dried over MgSO4, filtered and evaporated. The product was obtained after purification by flash chromatography (using silica gel and a dichloromethane/methanol/ammonia gradient)
as yellow solid (86 mg, 74%). MS: m/z=327.5 (M+H)+

Example 30

2-[4-(Fluoromethoxy)phenyl]-7-pyrrolidin-1-ylimidazo[1,2-a]pyrimidine

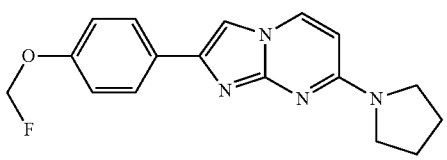 [SMILES: FCOc1ccc(-c2cn3ccc(N4CCCC4)nc3n2)cc1]

The product was obtained starting from 4-(7-(pyrrolidin-1-yl)imidazo[1,2-a]pyrimidin-2-yl)phenol (100 mg, 357 μmol, example 28) and fluoromethyl 4-methylbenzenesulfonate (72.9 mg, 357 μmol) according to the method described in example 29 as yellow solid (52 mg, 47%).
MS: m/z=313.5 (M+H)+

Example 31

7-[(3R)-3-Methoxypyrrolidin-1-yl]-2-phenylimidazo[1,2-a]pyrimidine

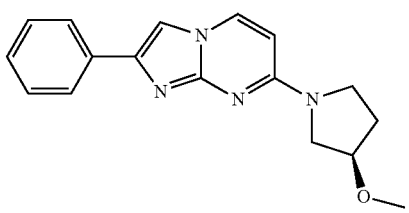

Step 1: (R)-4-(3-Methoxypyrrolidin-1-yl)pyrimidin-2-amine

The product was obtained starting from 4-chloropyrimidin-2-amine (255 mg, 1.97 mmol), (R)-3-methoxypyrrolidine hydrochloride (298 mg, 2.17 mmol) and potassium carbonate (816 mg, 5.91 mmol) according to the method described in example 2, step 1 and final purification by flash chromatography (using silica gel and a dichloromethane/methanol/ammonia gradient) as light yellow solid (321 mg, 84%). MS: m/z=195.2 (M+H)+

Step 2: 7-[(3R)-3-Methoxypyrrolidin-1-yl]-2-phenylimidazo[1,2-a]pyrimidine

The product was obtained starting from R)-4-(3-methoxypyrrolidin-1-yl)pyrimidin-2-amine (80 mg, 412 μmol, Eq: 1.00) and 2-bromo-1-phenylethanone (123 mg, 618 μmol, Eq: 1.5) according to the method described in example 1, step 2 as yellow solid (63 mg, 52%).
MS: m/z=295.8 (M+H)+

Example 32

7-[(3S)-3-Methoxypyrrolidin-1-yl]-2-phenylimidazo[1,2-a]pyrimidine

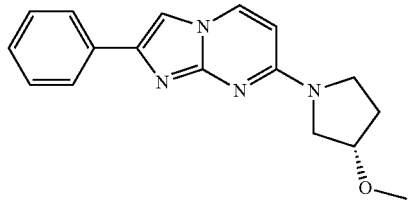 [SMILES: CO[C@H]1CCN(c2ccn3cc(-c4ccccc4)nc3n2)C1]

Step 1: (S)-4-(3-Methoxypyrrolidin-1-yl)pyrimidin-2-amine

The product was obtained starting from 4-chloropyrimidin-2-amine (360 mg, 2.78 mmol), (S)-3-methoxypyrrolidine (309 mg, 3.06 mmol) and potassium carbonate (768 mg, 5.56 mmol) according to the method described in example 2, step 1 and final purification by flash chromatography (using silica gel and a dichloromethane/methanol/ammonia gradient) as yellow solid (288 mg, 52%). MS: m/z=195.2 (M+H)+

Step 2: 7-[(3S)-3-Methoxypyrrolidin-1-yl]-2-phenylimidazo[1,2-a]pyrimidine

The product was obtained starting from (S)-4-(3-methoxypyrrolidin-1-yl)pyrimidin-2-amine (70 mg, 360 μmol) and 2-bromo-1-phenylethanone (108 mg, 541 μmol) according to the method described in example 1, step 2 as yellow solid (11 mg, 9%). MS: m/z=295.5 (M+H)+

Example 33

7-[(3R)-3-Fluoropyrrolidin-1-yl]-2-(4-methoxyphenyl)imidazo[1,2-a]pyrimidine

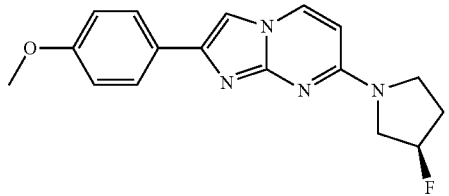 [SMILES: COc1ccc(-c2cn3ccc(N4CC[C@@H](F)C4)nc3n2)cc1]

Step 1: (R)-4-(3-Fluoropyrrolidin-1-yl)pyrimidin-2-amine

The product was obtained starting from 4-chloropyrimidin-2-amine (250 mg, 1.93 mmol), (R)-3-fluoropyrrolidine hydrochloride (242 mg, 1.93 mmol) and potassium carbonate (533 mg, 3.86 mmol) according to the method described in example 2, step 1 and final trituration with dichloromethane as light yellow solid (192 mg, 54%). MS: m/z=183.2 (M+H)+

Step 2: 7-[(3R)-3-Fluoropyrrolidin-1-yl]-2-(4-methoxyphenyl)imidazo[1,2-a]pyrimidine The product was obtained starting from (R)-4-(3-fluoropyrrolidin-1-yl)pyrimidin-2-amine (80.0 mg, 439 μmol) and 2-bromo-1-(4-methoxyphenyl)ethanone (151 mg, 659 μmol) according to the method described in example 1, step 2 as light yellow solid (89 mg, 65%).
MS: m/z=313.6 (M+H)+

Example 34

7-[(3 S)-3-Fluoropyrrolidin-1-yl]-2-(4-methoxyphenyl)imidazo[1,2-a]pyrimidine

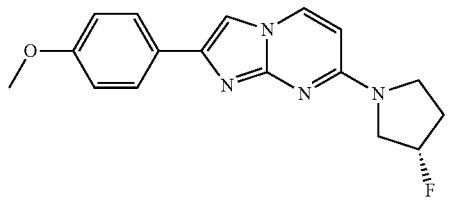 [SMILES: COc1ccc(-c2cn3ccc(N4CC[C@H](F)C4)nc3n2)cc1]

Step 1: (S)-4-(3-Fluoropyrrolidin-1-yl)pyrimidin-2-amine

The product was obtained starting from 4-chloropyrimidin-2-amine (360 mg, 2.78 mmol), (S)-3-fluoropyrrolidine hydrochloride (349 mg, 2.78 mmol) and potassium carbonate (768 mg, 5.56 mmol) according to the method described in example 2, step 1 and final trituration with dichloromethane as off-white solid (319 mg, 63%). MS: m/z=183.2 (M+H)+

Step 2: 7-[(3S)-3-Fluoropyrrolidin-1-yl]-2-(4-methoxyphenyl)imidazo[1,2-a]pyrimidine The product was obtained starting from (S)-4-(3-fluoropyrrolidin-1-yl)pyrimidin-2-amine (70 mg, 384 μmol) and 2-bromo-1-(4-methoxyphenyl)ethanone (132 mg, 576 μmol) according to the method described in example 1, step 2 as light yellow solid (77 mg, 64%).
MS: m/z=313.5 (M+H)+

Example 35

2-(3-Methoxyphenyl)-N,N-dimethylimidazo[1,2-a]pyrimidin-7-amine

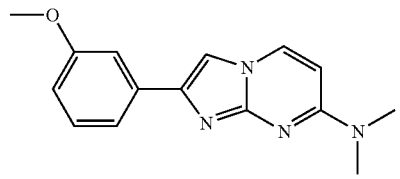

The product was obtained starting from N4,N4-dimethylpyrimidine-2,4-diamine (100 mg, 724 μmol, example 18, step 1) and 2-bromo-1-(3-methoxyphenyl)ethanone (249 mg, 1.09 mmol) according to the method described in example 1, step 2 as red solid (118 mg, 61%).
MS: m/z=269.1 (M+H)+

Example 36

2-(4-Methoxyphenyl)-N,N-dimethylimidazo[1,2-a]pyrimidin-7-amine

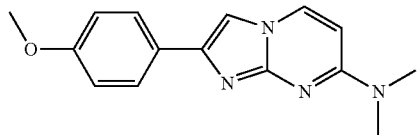

The product was obtained starting from N4,N4-dimethylpyrimidine-2,4-diamine (100 mg, 724 μmol, example 18, step 1) and 2-bromo-1-(4-methoxyphenyl)ethanone (249 mg, 1.09 mmol) according to the method described in example 1, step 2 as yellow solid (102 mg, 53%).
MS: m/z=269.1 (M+H)+

Example 37

2-(1,3-Benzodioxol-5-yl)-N,N-dimethylimidazo[1,2-a]pyrimidin-7-amine

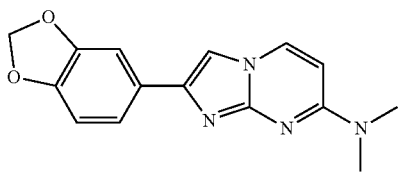 [SMILES: CN(C)c1ccn2cc(-c3ccc4c(c3)OCO4)nc2n1]

The product was obtained starting from N4,N4-dimethylpyrimidine-2,4-diamine (100 mg, 724 μmol, example 18, step 1) and 1-(benzo[d][1,3]dioxol-5-yl)-2-bromoethanone (264 mg, 1.09 mmol) according to the method described in example 1, step 2 as off-white solid (127 mg, 62%). MS: m/z=283.1 (M+H)+

Example 38

2-(2,3-Dihydro-1,4-benzodioxin-6-yl)-N,N-dimethylimidazo[1,2-a]pyrimidin-7-amine

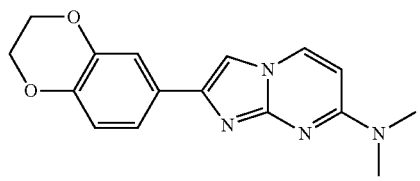 [SMILES: CN(C)c1ccn2cc(-c3ccc4c(c3)OCCO4)nc2n1]

The product was obtained starting from N4,N4-dimethylpyrimidine-2,4-diamine (100 mg, 724 μmol, step 1) and 2-bromo-1-(2,3-dihydrobenzo[b][1,4]dioxin-6-yl)ethanone (279 mg, 1.09 mmol) according to the method described in example 1, step 2 as yellow solid (140 mg, 65%).
MS: m/z=297.3 (M+H)+

Example 39

N,N-Dimethyl-2-(4-methylphenyl)imidazo[1,2-a]pyrimidin-7-amine

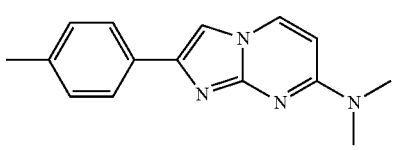

The product was obtained starting from N4,N4-dimethylpyrimidine-2,4-diamine (100 mg, 724 μmol, example 18, step 1) and 2-bromo-1-p-tolylethanone (231 mg, 1.09 mmol) according to the method described in example 1, step 2 as yellow solid (86 mg, 47%). MS: m/z=253.1 (M+H)+

Example 40

N,N-Dimethyl-2-(3-methylphenyl)imidazo[1,2-a]pyrimidin-7-amine

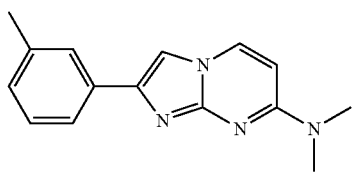 [SMILES: Cc1cccc(-c2cn3ccc(N(C)C)nc3n2)c1]

The product was obtained starting from N4,N4-dimethylpyrimidine-2,4-diamine (100 mg, 724 μmol, example 18, step 1) and 2-bromo-1-m-tolylethanone (462 mg, 2.18 mmol) according to the method described in example 1, step 2 as white solid (117 mg, 64%).
MS: m/z=253.1 (M+H)+

Example 41

4-[2-(3-Methoxyphenyl)imidazo[1,2-a]pyrimidin-7-yl]morpholine

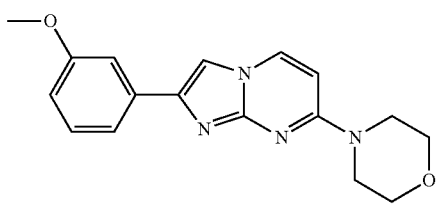 [SMILES: COc1cccc(-c2cn3ccc(N4CCOCC4)nc3n2)c1]

The product was obtained starting from 4-morpholin-4-yl-pyrimidin-2-ylamine (400 mg, 2.22 mmol, example 25, step 1) and 2-bromo-1-(3-methoxy-phenyl)-ethanone (763 mg, 3.33 mmol) according to the method described in example 49, step 2 as off-white solid (70 mg, 10%).

MS: m/z=311.0 (M+H)+

Example 42

4-[2-(4-Methylphenyl)imidazo[1,2-a]pyrimidin-7-yl]morpholine

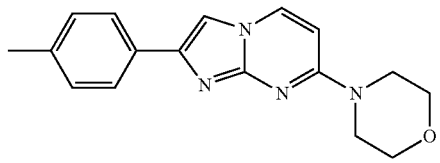 [SMILES: Cc1ccc(-c2cn3ccc(N4CCOCC4)nc3n2)cc1]

The product was obtained starting from 4-morpholin-4-yl-pyrimidin-2-ylamine (400 mg, 2.22 mmol, example 25, step 1) and 2-bromo-1-p-tolyl-ethanone (709 mg, 3.33 mmol) according to the method described in example 49, step 2 as white solid (230 mg, 35%).

MS: m/z=294.8 (M+H)+

Example 43

2-(4-Methoxyphenyl)-7-pyrrolidin-1-ylimidazo[1,2-a]pyrimidine

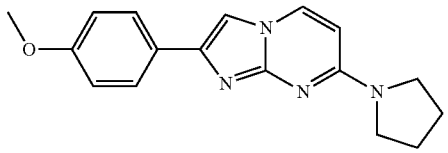 [SMILES: COc1ccc(-c2cn3ccc(N4CCCC4)nc3n2)cc1]

The product was obtained starting from 4-pyrrolidin-1-yl-pyrimidin-2-amine (400 mg, 2.22 mmol, example 16, step 1) and 2-bromo-1-(4-methoxy-phenyl)-ethanone (762 mg, 3.33 mmol) according to the method described in example 49, step 2 as light brown solid (65 mg, 10%).

MS: m/z=295.0 (M+H)+

Example 44

2-(4-Methylphenyl)-7-pyrrolidin-1-ylimidazo[1,2-a]pyrimidine

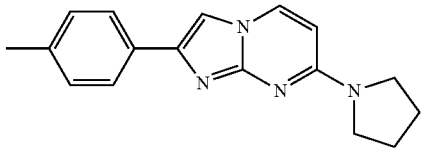 [SMILES: Cc1ccc(-c2cn3ccc(N4CCCC4)nc3n2)cc1]

The product was obtained starting from 4-pyrrolidin-1-yl-pyrimidin-2-amine (450 mg, 2.49 mmol, example 16, step 1) and 2-bromo-1-p-tolyl-ethanone (797 mg, 3.74 mmol) according to the method described in example 49, step 2 as off-white solid (130 mg, 19%).

MS: m/z=279.0 (M+H)+

Example 45

N,N-Dimethyl-2-(4-morpholin-4-ylphenyl)imidazo[1,2-a]pyrimidin-7-amine

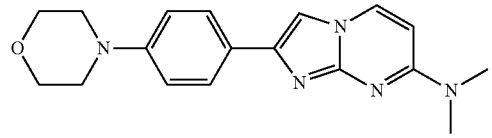 [SMILES: CN(C)c1ccn2cc(-c3ccc(N4CCOCC4)cc3)nc2n1]

The product was obtained starting from N4,N4-dimethylpyrimidine-2,4-diamine (100 mg, 724 μmol, example 18, step 1) and 2-bromo-1-(4-morpholinophenyl)ethanone (308 mg, 1.09 mmol) according to the method described in example 1, step 2 as yellow solid (116 mg, 50%).

MS: m/z=324.2 (M+H)+

Example 46

2-[4-(Dimethylamino)phenyl]-N,N-dimethylimidazo[1,2-a]pyrimidin-7-amine

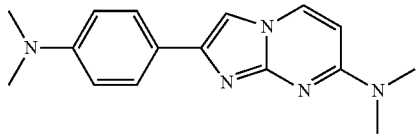

The product was obtained starting from N4,N4-dimethylpyrimidine-2,4-diamine (100 mg, 724 μmol, example 18, step 1) and 2-bromo-1-(4-(dimethylamino)phenyl)ethanone (263 mg, 1.09 mmol) according to the method described in example 1, step 2 as yellow solid (138 mg, 68%).

MS: m/z=282.8 (M+H)+

Example 47

2-(3-Methoxyphenyl)-7-pyrrolidin-1-ylimidazo[1,2-a]pyrimidine

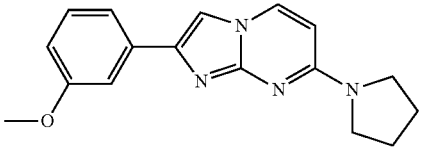 [SMILES: COc1cccc(-c2cn3ccc(N4CCCC4)nc3n2)c1]

The product was obtained starting from 4-pyrrolidin-1-yl-pyrimidin-2-amine (300 mg, 1.66 mmol, example 16, step 1) and 2-bromo-1-(3-methoxy-phenyl)-ethanone (572 mg, 2.49 mmol) according to the method described in example 49, step 2 as off-white solid (30 mg, 6%).
MS: m/z=295.0 (M+H)$^+$ Example 48

2-(3-Methylphenyl)-7-pyrrolidin-1-ylimidazo[1,2-a]pyrimidine

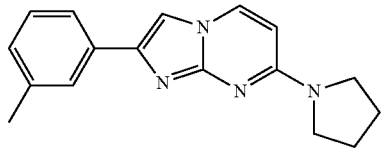 [SMILES: Cc1cccc(-c2cn3ccc(N4CCCC4)nc3n2)c1]

The product was obtained starting from 4-pyrrolidin-1-yl-pyrimidin-2-amine (300 mg, 1.66 mmol, example 16, step 1) and 2-bromo-1-m-tolyl-ethanone (532 mg, 2.49 mmol) according to the method described in example 49, step 2 as off-white solid (30 mg, 6%).
MS: m/z=278.8 (M+H)$^+$ Example 49

2-(4-Methoxyphenyl)-7-piperidin-1-ylimidazo[1,2-a]pyrimidine

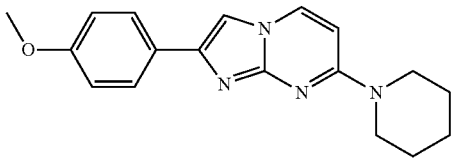 [SMILES: COc1ccc(-c2cn3ccc(N4CCCCC4)nc3n2)cc1]

Step 1: 4-Piperidin-1-yl-pyrimidin-2-amine

A mixture of 4-chloro-pyrimidin-2-ylamine (4 g, 31 mmol), piperidine (2.9 mL, 34.1 mmol), potassium carbonate (6.42 g, 46.5 mmol) and N-methyl-2-pyrrolidinone (8 mL) was heated in a sealed tube at 120° C. for 12 h. After cooling down to room temperature, the reaction mixture was poured into NaOH (1M aqueous solution, 120 mL) and extracted with dichloromethane (3×150 mL). The combined organic layers were dried over anhydrous Na$_2$SO$_4$, filtered, and concentrated in vacuum. The product was obtained after purification by flash chromatography (using silica gel and a dichloromethane/methanol gradient) as off-white solid (3 g, 54%).
MS: m/z=179.0 (M+H)$^+$ Step 2: 2-(4-Methoxyphenyl)-7-piperidin-1-ylimidazo[1,2-a]pyrimidine To a solution of 4-piperidin-1-yl-pyrimidin-2-ylamine (400 mg, 2.24 mol) in acetone (10 mL) was added under nitrogen 2-bromo-1-(4-methoxy-phenyl)-ethanone (763 mg, 3.33 mmol) and p-toluenesulfonic acid (catalytic amount) at 25° C. The reaction mixture was stirred at 65° C. for 12 h. All volatiles were removed under reduced pressure. The residue was partitioned between water and dichloromethane, and the aqueous phase was extracted with dichloromethane (3×150 mL). The combined organic layers were dried over anhydrous Na$_2$SO$_4$, filtered, and concentrated under reduced pressure. The product was obtained after purification by flash chromatography (using silica gel and a dichloromethane/methanol gradient) as off-white solid (20 mg, 3%).
MS: m/z=308.8 (M+H)$^+$ Example 50

2-(3-Methoxyphenyl)-7-piperidin-1-ylimidazo[1,2-a]pyrimidine

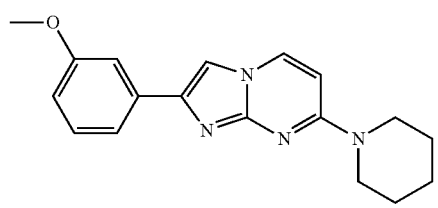 [SMILES: COc1cccc(-c2cn3ccc(N4CCCCC4)nc3n2)c1]

The product was obtained starting from 4-piperidin-1-yl-pyrimidin-2-ylamine (350 mg, 1.96 mmol, example 49, step 1) and 2-bromo-1-(3-methoxy-phenyl)-ethanone (676 mg, 2.94 mmol) according to the method described in example 49, step 2 as off-white solid (45 mg, 7%).
MS: m/z=309.3 (M+H)$^+$ Example 51

2-(4-Methylphenyl)-7-piperidin-1-ylimidazo[1,2-a]pyrimidine

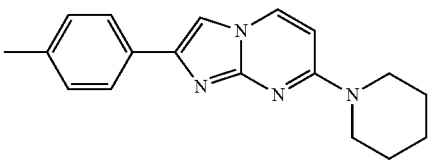 [SMILES: Cc1ccc(-c2cn3ccc(N4CCCCC4)nc3n2)cc1]

The product was obtained starting from 4-piperidin-1-yl-pyrimidin-2-ylamine (400 mg, 2.24 mmol, example 49, step 1) and 2-bromo-1-p-tolyl-ethanone (718 mg, 3.37 mmol) according to the method described in example 49, step 2 as off-white solid (200 mg, 30%).
MS: m/z=293.0 (M+H)$^+$ Example 52

2-(3-Methylphenyl)-7-piperidin-1-ylimidazo[1,2-a]pyrimidine

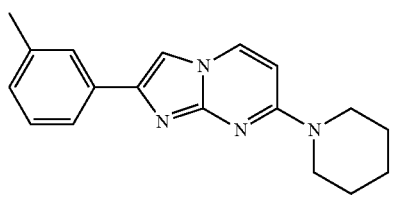 [SMILES: Cc1cccc(-c2cn3ccc(N4CCCCC4)nc3n2)c1]

The product was obtained starting from 4-piperidin-1-yl-pyrimidin-2-ylamine (350 mg, 1.96 mmol, example 49, step 1) and 2-bromo-1-m-tolyl-ethanone (628 mg, 2.95 mmol) according to the method described in example 49, step 2 as off-white solid (25 mg, 4%).

MS: m/z=293.3 (M+H)+

Example 53

2-(3,4-Dimethoxyphenyl)-7-piperidin-1-ylimidazo[1,2-a]pyrimidine

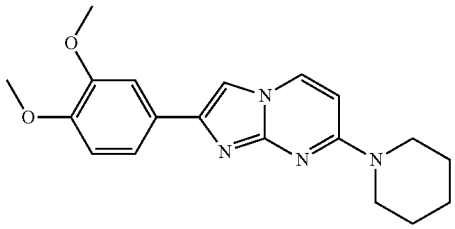 [SMILES: COc1ccc(-c2cn3ccc(N4CCCCC4)nc3n2)cc1OC]

The product was obtained starting from 4-piperidin-1-yl-pyrimidin-2-ylamine (250 mg, 1.40 mmol, example 49, step 1) and 2-bromo-1-(3,4-dimethoxy-phenyl)-ethanone (545 mg, 2.10 mmol) according to the method described in example 49, step 2 as off-white solid (49 mg, 10%).

Example 54

7-[4-(2-Fluoroethyl)piperidin-1-yl]-2-phenylimidazo[1,2-a]pyrimidine

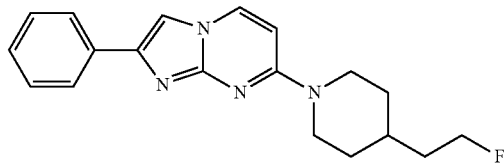 [SMILES: FCCC1CCN(c2ccn3cc(-c4ccccc4)nc3n2)CC1]

Step 1: tert-Butyl 4-(2-hydroxyethyl)piperidine-1-carboxylate

To a solution of 2-(piperidin-4-yl)ethanol (2.42 g, 18.7 mmol) in dichloromethane (24 mL) was added under nitrogen at 0° C. di-tert-butyl dicarbonate (4.09 g, 4.35 mL, 18.7 mmol). There was a strong gas evolution! The solution was stirred at 0° C. for 15 min and at room temperature for 4 h.

The reaction mixture was washed with water (50 mL), potassium hydrogen sulfate (10% aqueous solution, 50 mL) and brine (50 mL). The aqueous layers were back-extracted with dichloromethane (50 mL). The combined organic layers were dried over sodium sulfate to yield colorless oil (4.1 g, 95%). MS: m/z=230.5 (M+H)+

Step 2: tert-Butyl 4-(2-fluoroethyl)piperidine-1-carboxylate

To a solution of tert-butyl 4-(2-hydroxyethyl)piperidine-1-carboxylate (2.22 g, 9.7 mmol) in dichloromethane (20 mL) was added dropwise between 0-8° C. diethylaminosulfur trifluoride (1.72 g, 1.41 mL, 10.7 mmol) under nitrogen. The solution was stirred at 0° C. for 1 h and at room temperature for another 2 h. The reaction mixture was diluted with ethyl acetate (50 mL) and was washed with sodium carbonate (1 M aqueous solution, 50 mL), water (50 mL) and brine (50 mL). The aqueous layers were back-extracted with ethyl acetate (50 mL). The combined organic layers were dried over sodium sulfate, filtrated and evaporated. The product was obtained after purification by flash chromatography (using silica gel and a heptane/ethyl acetate gradient) as colorless liquid (1.26 g, 56%). MS: m/z=231 (M)+

Step 3: 4-(2-Fluoro-ethyl)-piperidine hydrochloride

A suspension of tert-butyl 4-(2-fluoroethyl)piperidine-1-carboxylate (1.21 g, 5.23 mmol) in hydrochloric acid (4 M in dioxane, 5.23 mL, 20.9 mmol) was stirred at room temperature for 2 h. The solution was concentrated in vacuum and dried on high vacuum to yield the product as white solid (906 mg, 100%). MS: m/z=132.2 (M−HCl+H)+

Step 4: 4-[4-(2-Fluoro-ethyl)-piperidin-1-yl]-pyrimidin-2-ylamine

The product was obtained starting from 4-chloro-pyrimidin-2-ylamine (4 g, 31 mmol), 4-(2-fluoro-ethyl)-piperidine, hydrochloride (5.7 g, 34.1 mmol) and potassium carbonate (6.4 g, 46.5 mmol) according to the method described in example 49, step 1 as light yellow sticky solid (5.4 g, 78%).

MS: m/z=225.0 (M+H)+

Step 5: 7-[4-(2-Fluoroethyl)piperidin-1-yl]-2-phenylimidazo[1,2-a]pyrimidine

The product was obtained starting from 4-[4-(2-fluoro-ethyl)-piperidin-1-yl]-pyrimidin-2-ylamine (250 mg, 1.11 mmol) and 2-bromo-1-phenyl-ethanone (332 mg, 1.67 mmol) according to the method described in example 49, step 2 and final purification by preparative HPLC (using Reprosil Gold, 250×20 mm, 5µ/C18, methanol/10 mM ammonium acetate in water) as off-white solid (90 mg, 25%). MS: m/z=325.3 (M+H)+

Example 55

7-[4-(2-Fluoroethyl)piperidin-1-yl]-2-(3-methoxyphenyl)imidazo[1,2-a]pyrimidine

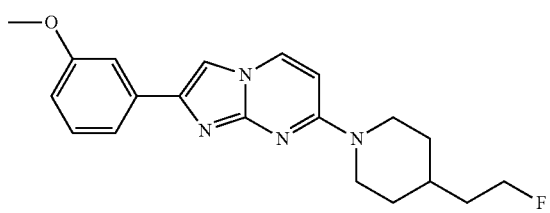 [SMILES: COc1cccc(-c2cn3ccc(N4CCC(CCF)CC4)nc3n2)c1]

The product was obtained starting from 4-[4-(2-fluoro-ethyl)-piperidin-1-yl]-pyrimidin-2-ylamine (250 mg, 1.11 mmol, example 54, step 4) and 2-bromo-1-(3-methoxy-phenyl)-ethanone (383 mg, 1.67 mmol) according to the method described in example 54, step 5 as off-white solid (30 mg, 8%). MS: m/z=355.1 (M+H)+

Example 56

7-[4-(2-Fluoroethyl)piperidin-1-yl]-2-(4-methoxyphenyl)imidazo[1,2-a]pyrimidine

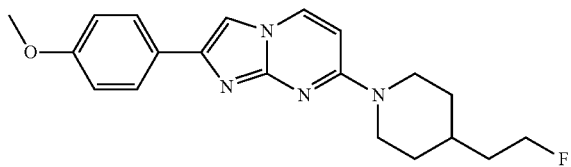 [SMILES: COc1ccc(-c2cn3ccc(N4CCC(CCF)CC4)nc3n2)cc1]

The product was obtained starting from 4-[4-(2-fluoroethyl)-piperidin-1-yl]-pyrimidin-2-ylamine (300 mg, 1.34 mmol, example 54, step 4) and 2-bromo-1-(4-methoxyphenyl)-ethanone (460 mg, 2.0 mmol) according to the method described in example 49, step 2 and final purification by preparative HPLC (using Xterra RP 18, 250×19 mm, 10μ/C18, acetonitrile/0.1% ammonia in water) as off-white solid (60 mg, 13%). MS: m/z=355.2 (M+H)$^+$

Example 57

2-(1,3-Benzodioxol-5-yl)-7-[4-(2-fluoroethyl)piperidin-1-yl]imidazo[1,2-a]pyrimidine

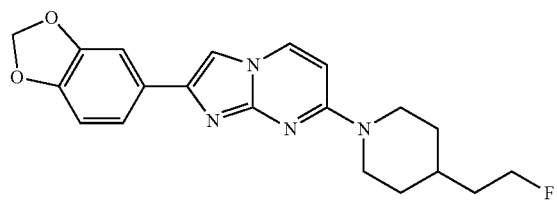 [SMILES: FCCC1CCN(c2ccn3cc(-c4ccc5c(c4)OCO5)nc3n2)CC1]

The product was obtained starting from 4-[4-(2-fluoroethyl)-piperidin-1-yl]-pyrimidin-2-ylamine (250 mg, 1.11 mmol, example 54, step 4) and 1-benzo[1,3]dioxol-5-yl-2-bromo-ethanone (406 mg, 1.67 mmol) according to the method described in example 54, step 5 as off-white solid (20 mg, 5%). MS: m/z=369.1 (M+H)$^+$

Example 58

2-(2,3-Dihydro-1,4-benzodioxin-6-yl)-7-[4-(2-fluoroethyl)piperidin-1-yl]imidazo[1,2-a]pyrimidine

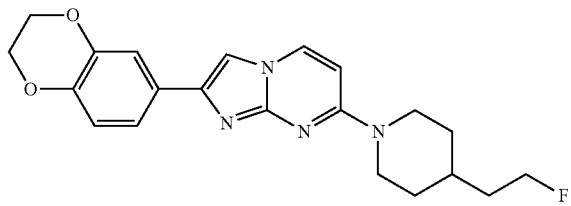 [SMILES: FCCC1CCN(c2ccn3cc(-c4ccc5c(c4)OCCO5)nc3n2)CC1]

The product was obtained starting from 4-[4-(2-fluoroethyl)-piperidin-1-yl]-pyrimidin-2-ylamine (250 mg, 1.11 mmol, example 54, step 4) and 2-bromo-1-(2,3-dihydrobenzo[1,4]dioxin-6-yl)-ethanone (430 mg, 1.67 mmol) according to the method described in example 54, step 5 as off-white solid (110 mg, 26%). MS: m/z=383.2 (M+H)$^+$

Example 59

7-[4-(2-Fluoroethyl)piperidin-1-yl]-2-(3-methylphenyl)imidazo[1,2-a]pyrimidine

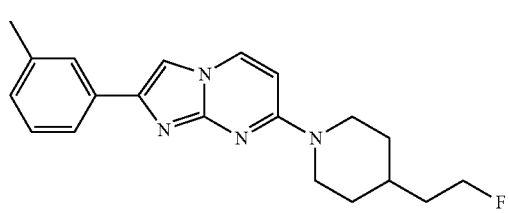 [SMILES: Cc1cccc(-c2cn3ccc(N4CCC(CCF)CC4)nc3n2)c1]

The product was obtained starting from 4-[4-(2-fluoroethyl)-piperidin-1-yl]-pyrimidin-2-ylamine (250 mg, 1.11 mmol, example 54, step 4) and 2-bromo-1-m-tolyl-ethanone (356 mg, 1.67 mmol) according to the method described in example 54, step 5 as off-white solid (90 mg, 24%). MS: m/z=339.1 (M+H)$^+$

Example 60

7-[4-(2-Fluoroethyl)piperidin-1-yl]-2-(4-methylphenyl)imidazo[1,2-a]pyrimidine

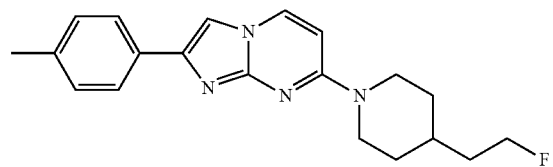 [SMILES: Cc1ccc(-c2cn3ccc(N4CCC(CCF)CC4)nc3n2)cc1]

The product was obtained starting from 4-[4-(2-fluoroethyl)-piperidin-1-yl]-pyrimidin-2-ylamine (300 mg, 1.34 mmol, example 54, step 4) and 2-bromo-1-p-tolyl-ethanone (427 mg, 2.00 mmol) according to the method described in example 54, step 5 as off-white solid (15 mg, 3%). MS: m/z=339.3 (M+H)$^+$

Example 61

4-[4-[7-[4-(2-Fluoroethyl)piperidin-1-yl]imidazo[1,2-a]pyrimidin-2-yl]phenyl]morpholine

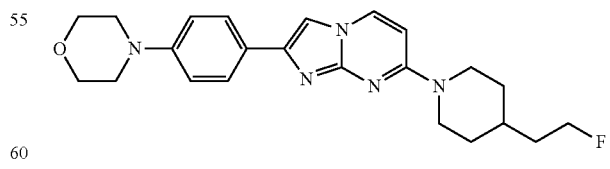

The product was obtained starting from 4-[4-(2-fluoroethyl)-piperidin-1-yl]-pyrimidin-2-ylamine (250 mg, 1.11 mmol, example 54, step 4) and 2-bromo-1-(4-morpholin-4-yl-phenyl)-ethanone (474 mg, 1.67 mmol) according to the method described in example 54, step 5 as off-white solid (30 mg, 6%). MS: m/z=410.2 (M+H)$^+$

Example 62

N-Methyl-2-(3-methylphenyl)imidazo[1,2-a]pyrimidin-7-amine

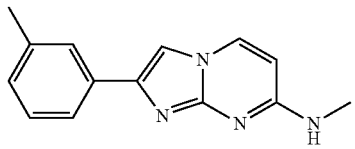 [SMILES: CNc1ccn2cc(-c3cccc(C)c3)nc2n1]

The product was obtained starting from N4-methylpyrimidine-2,4-diamine (30.0 mg, 242 µmol, example 1, step 1) and 2-bromo-1-m-tolylethanone (77.2 mg, 362 µmol) according to the method described in example 1, step 2 as light yellow solid (18 mg, 31%). MS: m/z=239.4 (M+H)+

Example 63

7-(4-Fluoropiperidin-1-yl)-2-thiophen-3-ylimidazo[1,2-a]pyrimidine

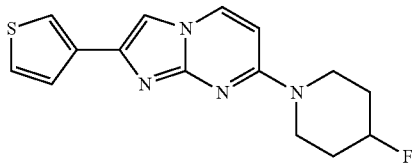 [SMILES: FC1CCN(c2ccn3cc(-c4ccsc4)nc3n2)CC1]

To a light yellow solution of 4-(4-fluoropiperidin-1-yl)pyrimidin-2-amine (50 mg, 255 µmol, example 2, step 1) and 2-bromo-1-(thiophen-3-yl)ethanone (57.5 mg, 280 µmol) in acetone (1 mL) was added at room temperature p-toluenesulfonic acid monohydrate (48.5 mg, 255 µmol) and the mixture was stirred at 60° C. for 48 h. The solvent was removed in vacuum and the residue was stirred in NaHCO₃ (saturated aqueous solution, 5 mL). The mixture was extracted with dichloromethane (3×15 mL). The organic layers were combined, dried over MgSO₄, filtered and evaporated. The product was obtained after purification by flash chromatography (using silica gel and an ethyl acetate/methanol gradient) and subsequent preparative HPLC (using Gemini 5 µ C18, 50×21.2 mm, 5µ/C18, acetonitrile/0.1% triethylamine in water) as white solid (2.4 mg, 3%). MS: m/z=303.5 (M+H)+

Example 64

N-[2-(2-Fluoroethoxy)ethyl]-2-(4-methoxyphenyl)-N-methylimidazo[1,2-a]pyrimidin-7-amine

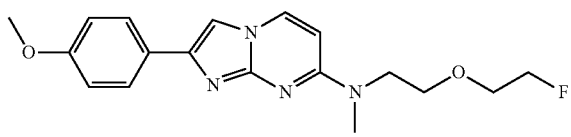

Step 1: 7-chloro-2-(4-methoxyphenyl)imidazo[1,2-a]pyrimidine and 7-bromo-2-(4-methoxyphenyl)imidazo[1,2-a]pyrimidine A light yellow solution of 4-chloropyrimidin-2-amine (2.0 g, 15.4 mmol) and 2-bromo-1-(4-methoxyphenyl)ethanone (5.3 g, 23.2 mmol) in acetone (94.0 mL) was stirred at 65° C. for 16 h. The reaction mixture was filtered and washed with acetone (~20 mL) and the resulting yellow solid was dried at high vacuum for 4 h. The crude product was poured into NaHCO₃ (saturated aqueous solution, 200 mL) and extracted with ethyl acetate (6×100 mL). The organic layers were combined, dried over MgSO₄, filtered and evaporated. The mixture of products was obtained after purification by flash chromatography (using silica gel and ethyl acetate) as a light yellow solid (245 mg, 5%).

MS: m/z=260.0 & 304.0 (M+H)+

Step 2: N-[2-(2-Fluoroethoxy)ethyl]-2-(4-methoxyphenyl)-N-methylimidazo[1,2-a]pyrimidin-7-amine A mixture of 7-chloro-2-(4-methoxyphenyl)imidazo[1,2-a]pyrimidine and 7-bromo-2-(4-methoxyphenyl)imidazo[1,2-a]pyrimidine (50 mg, 193 µmol related to chloride) was combined with DMSO (1.0 mL) under nitrogen to give an off-white suspension. 2-(2-Fluoroethoxy)-N-methylethanamine hydrochloride (36.4 mg, 231 µmol) and diisopropylethylamine, (99.5 mg, 131 µL, 770 µmol) were added and the reaction mixture was stirred at 130° C. for 3 h. The brown solution was diluted with water (5 mL) and extracted with dichloromethane (3×5 mL). The organic layers were combined, washed with brine (5 mL), dried over MgSO₄, filtered and evaporated. The product was obtained after purification by flash chromatography (using silica gel amine phase and a heptane/ethyl acetate gradient) as yellow solid (45 mg, 67%).

MS: m/z=345.5 (M+H)+

Example 65

7-(2-Azaspiro[3.3]heptan-2-yl)-2-(4-methoxyphenyl)imidazo[1,2-a]pyrimidine

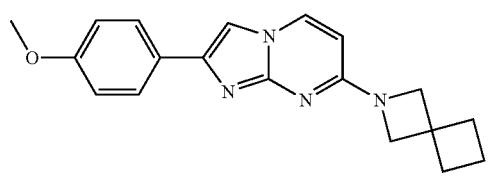 [SMILES: COc1ccc(-c2cn3ccc(N4CC5(CCC5)C4)nc3n2)cc1]

The product was obtained starting from 7-chloro-2-(4-methoxyphenyl)imidazo[1,2-a]pyrimidine and 7-bromo-2-(4-methoxyphenyl)imidazo[1,2-a]pyrimidine (50 mg, 193 µmol related to chloride, example 64, step 1) and 2-azaspiro[3.3]heptane hydrochloride (25.7 mg, 193 µmol) according to the method described in example 64, step 2 as light yellow solid (14 mg, 22%).

MS: m/z=321.5 (M+H)+

Example 66

N-Ethyl-2-(4-methoxyphenyl)-N-methylimidazo[1,2-a]pyrimidin-7-amine

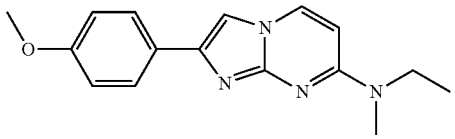 [SMILES: CCN(C)c1ccn2cc(-c3ccc(OC)cc3)nc2n1]

The product was obtained starting from 7-chloro-2-(4-methoxyphenyl)imidazo[1,2-a]pyrimidine and 7-bromo-2-(4-methoxyphenyl)imidazo[1,2-a]pyrimidine (50 mg, 193 µmol related to chloride, example 64, step 1) and N-methylethanamine (11.4 mg, 193 µmol) according to the method described in example 64, step 2 as yellow solid (10 mg, 18%).
MS: m/z=283.5 (M+H)+

Example 67

N,N-Diethyl-2-(4-methoxyphenyl)imidazo[1,2-a]pyrimidin-7-amine

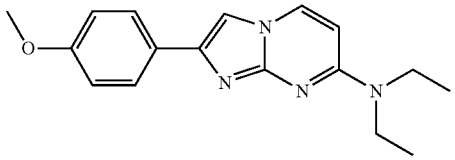 [SMILES: CCN(CC)c1ccn2cc(-c3ccc(OC)cc3)nc2n1]

The product was obtained starting from 7-chloro-2-(4-methoxyphenyl)imidazo[1,2-a]pyrimidine and 7-bromo-2-(4-methoxyphenyl)imidazo[1,2-a]pyrimidine (50 mg, 193 µmol related to chloride, example 64, step 1) and diethylamine (21.2 mg, 30 µl, 290 µmol) according to the method described in example 64, step 2 as yellow solid (26 mg, 45%). MS: m/z=297.2 (M+H)+

Example 68

N-[2-(2-Fluoroethoxy)ethyl]-N-methyl-2-(3-methylphenyl)imidazo[1,2-a]pyrimidin-7-amine

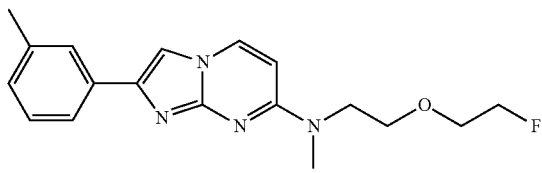 [SMILES: Cc1cccc(-c2cn3ccc(N(C)CCOCCF)nc3n2)c1]

Step 1: 7-Chloro-2-m-tolylimidazo[1,2-a]pyrimidine

The product was obtained starting from 4-chloropyrimidin-2-amine (1.0 g, 7.72 mmol) and 2-bromo-1-m-tolylethanone (2.47 g, 11.6 mmol) according to the method described in example 1, step 2 as brown solid (535 mg, 25%). MS: m/z=244.4 (M+H)+

Step 2: N-[2-(2-Fluoroethoxy)ethyl]-N-methyl-2-(3-methylphenyl)imidazo[1,2-a]pyrimidin-7-amine The product was obtained starting from 7-chloro-2-m-tolylimidazo[1,2-a]pyrimidine (50 mg, 205 µmol) and 2-(2-fluoroethoxy)-N-methylethanamine hydrochloride (38.8 mg, 246 µmol) according to the method described in example 64, step 2 and subsequent preparative TLC (using silica gel 1 mm and ethyl acetate) as light brown oil solid (18 mg, 27%). MS: m/z=329.5 (M+H)+

Example 69

7-(Azetidin-1-yl)-2-(4-methoxyphenyl)imidazo[1,2-a]pyrimidine

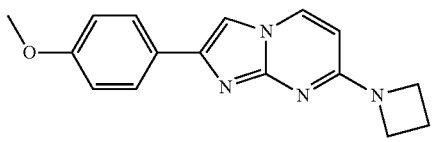 [SMILES: COc1ccc(-c2cn3ccc(N4CCC4)nc3n2)cc1]

Step 1: 4-(Azetidin-1-yl)pyrimidin-2-amine

A microwave vial was charged with 4-chloropyrimidin-2-amine (0.300 g, 2.32 mmol), azetidine (271 mg, 0.32 ml, 4.75 mmol), N,N-diisopropylethylamine (363 mg, 0.49 ml, 2.81 mmol) and methanol (3.0 mL). The vial was flushed with argon, closed and stirred at 60° C. (oil bath temperature) for 2 h. The reaction mixture was cooled to room temperature and concentrated. The residue (pale yellow solid) was suspended in water, filtered and rinsed with water. The product was obtained after drying of the residue under high vacuum as off-white powder (287 mg, 82%). MS: m/z=151.4 (M+H)+

Step 2: 7-(Azetidin-1-yl)-2-(4-methoxyphenyl)imidazo[1,2-a]pyrimidine

A microwave vial was charged with 4-(azetidin-1-yl)pyrimidin-2-amine (0.050 g, 333 µmol), 2-bromo-1-(4-methoxyphenyl)ethanone (80 mg, 349 µmol) and Acetone (0.6 mL). The vial was flushed with argon and closed. The reaction mixture was stirred at 70° C. (=oil bath temperature) overnight, cooled to room temperature and extracted with dichloromethane and saturated Na₂CO₃-solution. The aqueous layer was extracted twice with dichloromethane. The organic layers were combined, dried over Na₂SO₄, filtered and concentrated. The product was obtained after trituration of the residue (light yellow solid) with ethyl acetate and a few drops of methanol as off-white powder (72 mg, 77%). MS: m/z=281.5 (M+H)+

Example 70

7-(3-Fluoroazetidin-1-yl)-2-(4-methoxyphenyl)imidazo[1,2-a]pyrimidine

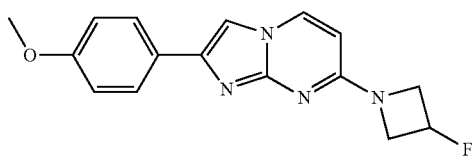 [SMILES: COc1ccc(-c2cn3ccc(N4CC(F)C4)nc3n2)cc1]

Step 1: 4-(3-Fluoroazetidin-1-yl)pyrimidin-2-amine

The product was obtained starting from 4-chloropyrimidin-2-amine (0.400 g, 3.09 mmol) and 3-fluoroazetidine hydrochloride (379 mg, 3.4 mmol) according to the method described in example 69, step 1 as off-white powder (257 mg, 50%). MS: m/z=169.3 (M+H)$^+$

Step 2: 7-(3-Fluoroazetidin-1-yl)-2-(4-methoxyphenyl)imidazo[1,2-a]pyrimidine A microwave vial was charged with 4-(3-fluoroazetidin-1-yl)pyrimidin-2-amine (0.050 g, 297 μmol), 2-bromo-1-(4-methoxyphenyl)ethanone (72 mg, 314 μmol) and acetone (0.5 mL). The vial was flushed with argon and closed. The reaction mixture was stirred at 70° C. (=oil bath temperature) overnight, cooled to room temperature, diluted with acetone (~0.5 ml) and water (1 mL) and basified with ammonium hydroxide solution (~25%, ~0.5 mL). The suspension was stirred at room temperature for 5 min, filtered and washed with water and acetone. The product was obtained after drying of the residue under high vacuum as off-white solid (41 mg, 46.2%).

MS: m/z=299.4 (M+H)$^+$

Example 71

7-(3-Fluoroazetidin-1-yl)-2-phenylimidazo[1,2-a]pyrimidine

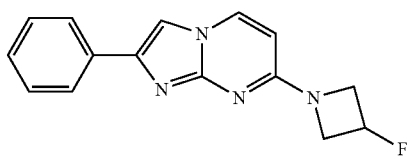 [SMILES: FC1CN(c2ccn3cc(-c4ccccc4)nc3n2)C1]

The product was obtained starting from 4-(3-fluoroazetidin-1-yl)pyrimidin-2-amine (50 mg, 297 μmol, example 70, step 1) and 2-bromo-1-phenylethanone (63 mg, 317 μmol) according to the method described in example 69, step 2 as off-white powder (45 mg, 56%).

MS: m/z=269.4 (M+H)$^+$

Example 72

7-(3-Fluoroazetidin-1-yl)-2-(3-methylphenyl)imidazo[1,2-a]pyrimidine

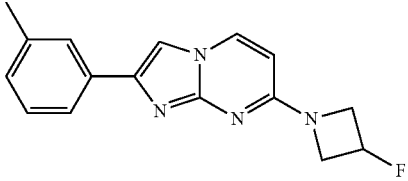 [SMILES: Cc1cccc(-c2cn3ccc(N4CC(F)C4)nc3n2)c1]

The product was obtained starting from 4-(3-fluoroazetidin-1-yl)pyrimidin-2-amine (50 mg, 297 μmol, example 70, step 1) and 2-bromo-1-m-tolylethanone (72 mg, 321 μmol) according to the method described in example 69, step 2 as light yellow powder (39 mg, 46%).

MS: m/z=283.5 (M+H)$^+$

Example 73

2-(1-Benzofuran-2-yl)-7-(4-fluoropiperidin-1-yl)imidazo[1,2-a]pyrimidine

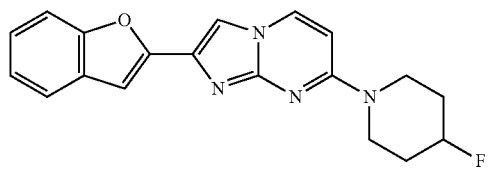 [SMILES: FC1CCN(c2ccn3cc(-c4cc5ccccc5o4)nc3n2)CC1]

The product was obtained starting from 4-(4-fluoropiperidin-1-yl)pyrimidin-2-amine (50 mg, 255 μmol, example 2, step 1) and 1-(benzofuran-2-yl)-2-bromoethanone (67.0 mg, 280 μmol) according to the method described in example 63 after single purification by flash chromatography as off-white solid (31 mg, 36%). MS: m/z=337.6 (M+H)$^+$

Example 74

N,N-Dimethyl-4-(7-morpholin-4-ylimidazo[1,2-a]pyrimidin-2-yl)aniline

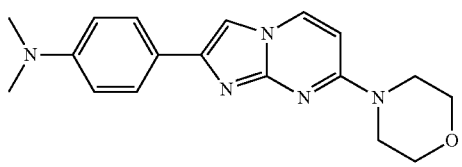 [SMILES: CN(C)c1ccc(-c2cn3ccc(N4CCOCC4)nc3n2)cc1]

The product was obtained starting from 4-morpholin-4-yl-pyrimidin-2-ylamine (120 mg, 666 μmol, example 25, step 1) and 2-bromo-1-(4-(dimethylamino)phenyl)ethanone (161 mg, 666 μmol) according to the method described in example 1, step 2 as light yellow solid (19 mg, 8%).
MS: m/z=324.5 (M+H)+

Example 75

2-(1-Benzothiophen-2-yl)-7-(4-fluoropiperidin-1-yl)imidazo[1,2-a]pyrimidine

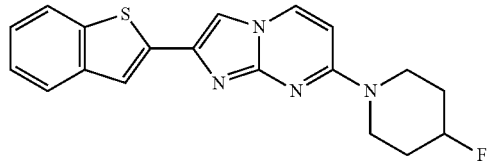

A suspension of 4-(4-fluoropiperidin-1-yl)pyrimidin-2-amine (74 mg, 377 μmol, example 2, step 1), 1-(benzo[b]thiophen-2-yl)-2-bromoethanone (144 mg, 566 μmol) and NaHCO₃ (47.5 mg, 566 μmol) in methanol (1.5 mL) was stirred at 76° C. under argon for 3 h, cooled to room temperature and poured to NaOH (1N aqueous solution). The mixture was extracted twice with dichloromethane. The organic layers were combined, dried over Na₂SO₄, filtered and concentrated. The product was obtained after purification by flash chromatography (using silica gel amine phase and a heptane/ethyl acetate gradient) as light brown solid (85 mg, 64%).
MS: m/z=353.4 (M+H)+

Example 76

N-Cyclopropyl-2-(4-methoxyphenyl)imidazo[1,2-a]pyrimidin-7-amine

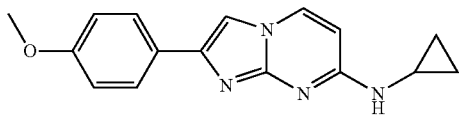 [SMILES: COc1ccc(-c2cn3ccc(NC4CC4)nc3n2)cc1]

Step 1: N4-Cyclopropylpyrimidine-2,4-diamine

To a suspension of 4-chloropyrimidin-2-amine (0.300 g, 2.32 mmol) and potassium carbonate (640 mg, 4.63 mmol) in DMF(3.0 mL) was added cyclopropylamine (1207 mg, 1.49 ml, 21.15 mmol) and the reaction mixture was stirred at 100° C. (=oil bath temperature) overnight. The reaction mixture was cooled to room temperature and extracted with ethyl acetate and water and the aqueous layer was back-extracted with ethyl acetate. The organic layers were washed three times with water and once with brine. The organic layers were combined, dried over Na₂SO₄, filtered and concentrated. The product was obtained after trituration of the residue (yellow solid) with diethyl ether as off-white solid (193 mg, 55%). MS: m/z=151.4 (M+H)+

Step 2: N-Cyclopropyl-2-(4-methoxyphenyl)imidazo[1,2-a]pyrimidin-7-amine

The product was obtained starting from N4-cyclopropylpyrimidine-2,4-diamine (50 mg, 333 μmol) and 2-bromo-1-(4-methoxyphenyl)ethanone (81 mg, 354 μmol) according to the method described in example 69, step 2 as light yellow solid (43 mg, 41%). MS: m/z=281.5 (M+H)+

Example 77

N-Isopropyl-2-(4-methoxy-phenyl)-imidazo[1,2-a]pyrimidin-7-amine

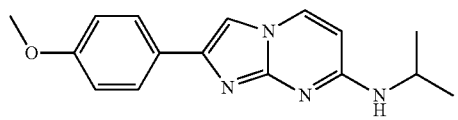 [SMILES: COc1ccc(-c2cn3ccc(NC(C)C)nc3n2)cc1]

Step 1: N4-Isopropylpyrimidine-2,4-diamine

A microwave vial was charged with 4-chloropyrimidin-2-amine (300 mg, 2.32 mmol), isopropylamine (828 mg, 1.2 ml, 14.0 mmol) and water (1.0 mL). The vial was flushed with argon, closed and stirred at 180° C. for 30 min under microwave irradiation (caution: the pressure reached>20 bar!). The reaction mixture was cooled to room temperature and extracted with dichloromethane and water. The organic layer was washed with water and the aqueous layers were back-extracted with dichloromethane. The organic layers were combined, dried over Na₂SO₄, filtered and concentrated. The product was obtained after triturating the residue with diethyl ether and a few drops of ethyl acetate as off-white solid (282 mg, 80%).
MS: m/z=153.4 (M+H)+

Step 2: N-Isopropyl-2-(4-methoxyphenyl)imidazo[1,2-a]pyrimidin-7-amine

The product was obtained starting from N4-isopropylpyrimidine-2,4-diamine (0.050 g, 329 μmol) and 2-bromo-1-(4-methoxyphenyl)ethanone (79 mg, 345 μmol) according to the method described in example 69, step 2 and final purification by flash chromatography (using silica gel and a dichloromethane/methanol gradient) as light yellow solid (59 mg, 64%).
MS: m/z=283.5 (M+H)+

Example 78

2-(4-Methoxyphenyl)-N-(2,2,2-trifluoroethyl)imidazo[1,2-a]pyrimidin-7-amine

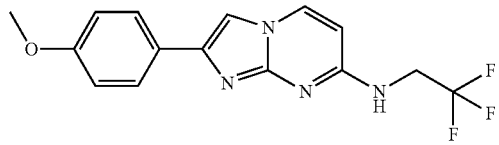 [SMILES: COc1ccc(-c2cn3ccc(NCC(F)(F)F)nc3n2)cc1]

Step 1: N4-(2,2,2-Trifluoroethyl)pyrimidine-2,4-diamine

The product was obtained starting from 4-chloropyrimidin-2-amine (300 mg, 2.32 mmol) and 2,2,2-trifluoroethylamine (1.26 g, 1.0 ml, 12.7 mmol) according to the method described in example 77, step 1 without final trituration as light yellow solid (121 mg, 26%).

Step 2: 2-(4-Methoxyphenyl)-N-(2,2,2-trifluoroethyl)imidazo[1,2-a]pyrimidin-7-amine The product was obtained starting from N4-(2,2,2-trifluoroethyl)pyrimidine-2,4-diamine (0.055 g, 272 μmol) and 2-bromo-1-(4-methoxyphenyl)ethanone (66 mg, 288 μmol) according to the method described in example 69, step 2 as light yellow solid (47 mg, 54%).
MS: m/z=323.4 (M+H)$^+$ Example 79

2-[7-(4-Fluoropiperidin-1-yl)imidazo[1,2-a]pyrimidin-2-yl]-1,3-benzothiazole

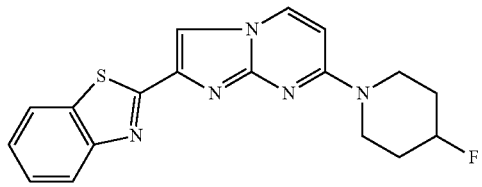 [SMILES: FC1CCN(c2ccn3cc(-c4nc5ccccc5s4)nc3n2)CC1]

A microwave vial was charged with 4-(4-fluoropiperidin-1-yl)pyrimidin-2-amine (50 mg, 255 μmol) and MeOH (849 μl) and stirred for 5 min to give a colorless solution. 1-(Benzo[d]thiazol-2-yl)-2-bromoethanone (91.4 mg, 357 μmol) and sodium bicarbonate (21.4 mg, 255 μmol) were added, the vial was sealed and the reaction mixture was stirred at 76° C. for 3 h. The solvent was evaporated and the residue was diluted with 1 M NaOH and extracted with dichloromethane. The organic phase was dried over MgSO$_4$ and concentrated under reduced pressure. The product was obtained after purification by flash chromatography (using silica gel and a dichloromethane/methanol/ammonia gradient) as orange powder (67 mg, 74%).
MS: m/z=354.5 (M+H)$^+$ Example 80

4-[7-(Azetidin-1-yl)imidazo[1,2-a]pyrimidin-2-yl]phenol

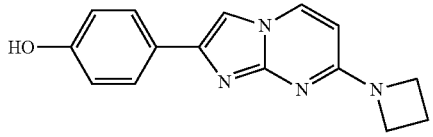 [SMILES: Oc1ccc(-c2cn3ccc(N4CCC4)nc3n2)cc1]

A microwave vial was charged with 4-(azetidin-1-yl)pyrimidin-2-amine (70 mg, 466 μmol, example 69, step 1), 2-bromo-1-(4-hydroxyphenyl)ethanone (105 mg, 489 μmol) and acetone (0.70 mL). The vial was flushed with argon, closed and stirred at 70° C. (=oil bath temperature) overnight. The reaction mixture was cooled to room temperature and then diluted with dichloromethane and saturated NaHCO$_3$-solution whereof a precipitate formed in the aqueous layer. The aqueous layer was filtered, rinsing with water and ethyl acetate and the product was obtained after drying of the residue under high vacuum as light yellow solid (115 mg, 93%).
MS: m/z=267.5 (M+H)$^+$ Example 81

7-(3-Methoxyazetidin-1-yl)-2-(4-methoxyphenyl)imidazo[1,2-a]pyrimidine

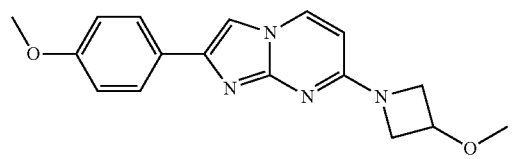

Step 1:
4-(3-Methoxyazetidin-1-yl)pyrimidin-2-amine

The product was obtained starting from 4-chloropyrimidin-2-amine (300 mg, 2.32 mmol), 3-methoxyazetidine hydrochloride (572 mg, 4.63 mmol) and N,N-diisopropylethylamine (888 mg, 1.2 ml, 6.87 mmol) according to the method described in example 77, step 1 after final trituration with ethyl acetate as light yellow solid (179 mg, 43%). MS: m/z=181.4 (M+H)$^+$ Step 2: 7-(3-Methoxyazetidin-1-yl)-2-(4-methoxyphenyl)imidazo[1,2-a]pyrimidine The product was obtained starting from 4-(3-methoxyazetidin-1-yl)pyrimidin-2-amine (0.050 g, 277 μmol) and 2-bromo-1-(4-methoxyphenyl)ethanone (67 mg, 292 μmol) according to the method described in example 69, step 2 and final purification by flash chromatography (using silica gel and a dichloromethane/methanol gradient) as light yellow solid (54 mg, 63%).
MS: m/z=311.5 (M+H)$^+$ Example 82

N-Methyl-2-(4-methylphenyl)imidazo[1,2-a]pyrimidin-7-amine

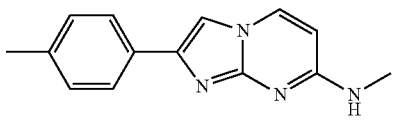

The product was obtained starting from N4-methylpyrimidine-2,4-diamine (50 mg, 403 μmol, example 1, step 1) and 2-bromo-1-p-tolylethanone (129 mg, 604 μmol) according to the method described in example 1, step 2 as off-white solid (38 mg, 40%). MS: m/z=239.5 (M+H)$^+$

Example 83

2-(4-Methoxyphenyl)-N-methylimidazo[1,2-a]pyrimidin-7-amine

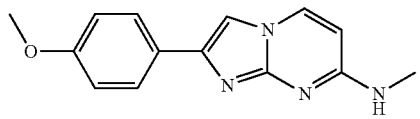

The product was obtained starting from N4-methylpyrimidine-2,4-diamine (200 mg, 1.61 mmol, example 1, step 1) and 2-bromo-1-(4-methoxyphenyl)ethanone (554 mg, 2.42 mmol) according to the method described in example 1, step 2 as yellow solid (284 mg, 69%).

MS: m/z=255.5 (M+H)$^+$

Example 84

2-(1,3-Benzodioxol-5-yl)-N-methylimidazo[1,2-a]pyrimidin-7-amine

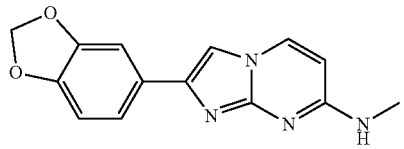 [SMILES: CNc1ccn2cc(-c3ccc4c(c3)OCO4)nc2n1]

The product was obtained starting from N4-methylpyrimidine-2,4-diamine (50 mg, 403 μmol, example 1, step 1) and 1-(benzo[d][1,3]dioxol-5-yl)-2-bromoethanone (147 mg, 604 μmol) according to the method described in example 1, step 2 as light yellow solid (57 mg, 53%).

MS: m/z=269.4 (M+H)$^+$

Example 85

N,N-Dimethyl-2-thiophen-3-ylimidazo[1,2-a]pyrimidin-7-amine

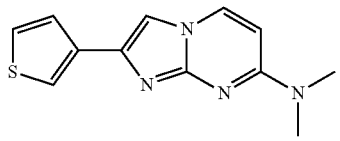 [SMILES: CN(C)c1ccn2cc(-c3ccsc3)nc2n1]

The product was obtained starting from N4,N4-dimethylpyrimidine-2,4-diamine (100 mg, 724 μmol, example 18, step 1) and 2-bromo-1-(thiophen-3-yl)ethanone (223 mg, 1.09 mmol) according to the method described in example 75 as light yellow solid (40 mg, 23%).

MS: m/z=245.4 (M+H)$^+$

Example 86

N-(2-Fluoroethyl)-N-methyl-2-(4-methylphenyl)imidazo[1,2-a]pyrimidin-7-amine

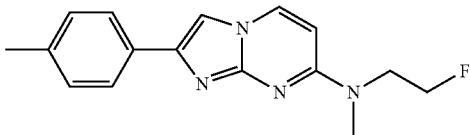 [SMILES: Cc1ccc(-c2cn3ccc(N(C)CCF)nc3n2)cc1]

The product was obtained starting from N4-(2-fluoroethyl)-N4-methylpyrimidine-2,4-diamine (50 mg, 294 μmol, example 21, step 1) and 2-bromo-1-p-tolylethanone (93.9 mg, 441 μmol) according to the method described in example 1, step 2 as white solid (5.4 mg, 6%).

MS: m/z=285.5 (M+H)$^+$

Example 87

2-(1,3-Benzodioxol-5-yl)-N-(2-fluoroethyl)-N-methylimidazo[1,2-a]pyrimidin-7-amine

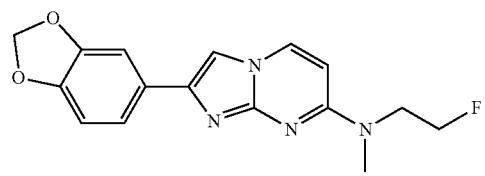 [SMILES: CN(CCF)c1ccn2cc(-c3ccc4c(c3)OCO4)nc2n1]

The product was obtained starting from N4-(2-fluoroethyl)-N4-methylpyrimidine-2,4-diamine (50 mg, 294 μmol, example 21, step 1) and 1-(benzo[d][1,3]dioxol-5-yl)-2-bromoethanone (107 mg, 441 μmol) according to the method described in example 1, step 2 as light yellow solid (43 mg, 44%). MS: m/z=315.4 (M+H)$^+$

Example 88

N-(2-Fluoroethyl)-N-methyl-2-(3-methylphenyl)imidazo[1,2-a]pyrimidin-7-amine

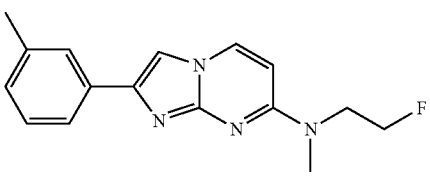

The product was obtained starting from N4-(2-fluoroethyl)-N4-methylpyrimidine-2,4-diamine (50 mg, 294 μmol, example 21, step 1) and 2-bromo-1-m-tolylethanone (93.9 mg, 441 μmol) according to the method described in example 1, step 2 as light brown solid (5 mg, 5%).

MS: m/z=285.5 (M+H)$^+$

Example 89

2-(4-Methoxyphenyl)-7-(3-methylazetidin-1-yl)imidazo[1,2-a]pyrimidine

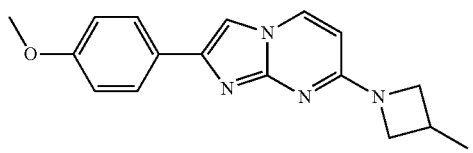

Step 1: 4-(3-Methylazetidin-1-yl)pyrimidin-2-amine

The product was obtained starting from 4-chloropyrimidin-2-amine (0.240 g, 1.85 mmol), 3-methylazetidine benzenesulfonate (680 mg, 2.96 mmol) and N,N-diisopropylethylamine (666 mg, 0.90 ml, 5.15 mmol) according to the method described in example 77, step 1 and final trituration with very little ethyl acetate as light yellow solid (112 mg, 33%).

MS: m/z=165.4 (M+H)$^+$

Step 2: 2-(4-Methoxyphenyl)-7-(3-methylazetidin-1-yl)imidazo[1,2-a]pyrimidine The product was obtained starting from 4-(3-methylazetidin-1-yl)pyrimidin-2-amine (0.055 g, 301 µmol) and 2-bromo-1-(4-methoxyphenyl)ethanone (76 mg, 332 µmol) according to the method described in example 69, step 2 and final purification by flash chromatography (using silica gel and a dichloromethane/methanol gradient) as light yellow solid (68 mg, 77%).

MS: m/z=295.5 (M+H)$^+$

Example 90

2-[4-(Dimethylamino)phenyl]-N-methylimidazo[1,2-a]pyrimidin-7-amine

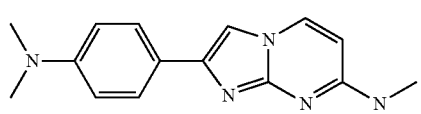

The product was obtained starting from N4-methylpyrimidine-2,4-diamine (100 mg, 806 µmol, example 1, step 1) and 2-bromo-1-(4-(dimethylamino)phenyl)ethanone (234 mg, 967 µmol) according to the method described in example 1, step 2 as yellow solid (168 mg, 78%).

MS: m/z=268.5 (M+H)$^+$

Example 91

4-[7-(4-Fluoropiperidin-1-yl)imidazo[1,2-a]pyrimidin-2-yl]-N,N-dimethylaniline

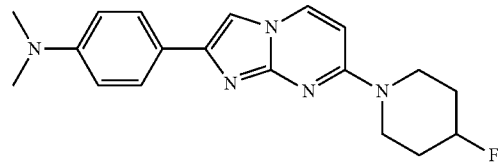 [SMILES: CN(C)c1ccc(-c2cn3ccc(N4CCC(F)CC4)nc3n2)cc1]

The product was obtained starting from 4-(4-fluoropiperidin-1-yl)pyrimidin-2-amine (50 mg, 255 µmol, example 2, step 1) and 2-bromo-1-(4-(dimethylamino)phenyl)ethanone (92.5 mg, 382 µmol) according to the method described in example 1, step 2 as light yellow solid (13 mg, 15%). MS: m/z=340.5 (M+H)$^+$

Example 92

2-[4-(Dimethylamino)phenyl]-N-(2-fluoroethyl)-N-methylimidazo[1,2-a]pyrimidin-7-amine

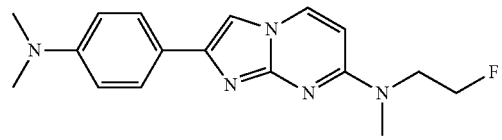 [SMILES: CN(C)c1ccc(-c2cn3ccc(N(C)CCF)nc3n2)cc1]

The product was obtained starting from N4-(2-fluoroethyl)-N4-methylpyrimidine-2,4-diamine (120 mg, 705 µmol, example 21, step 1) and 2-bromo-1-(4-(dimethylamino)phenyl)ethanone (205 mg, 846 µmol) according to the method described in example 1, step 2 after trituration of the crude product with diethyl ether and final purification by flash chromatography (using silica gel amine phase and a heptane/ethyl acetate gradient) as yellow solid (42 mg, 19%).

MS: m/z=314.5 (M+H)$^+$

Example 93

N-Cyclopropyl-2-(4-methoxyphenyl)-N-methylimidazo[1,2-a]pyrimidin-7-amine

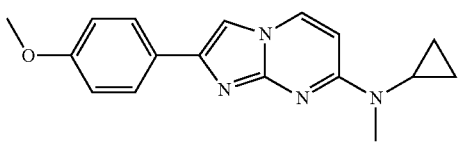 [SMILES: COc1ccc(-c2cn3ccc(N(C)C4CC4)nc3n2)cc1]

Step 1: N4-Cyclopropyl-N4-methylpyrimidine-2,4-diamine

The product was obtained starting from 4-chloropyrimidin-2-amine (300 mg, 2.32 mmol) and N-methylcyclopropanamine (494 mg, 6.95 mmol) according to the method described in example 77, step 1 and final trituration with ethyl acetate as white solid (237 mg, 62%).

MS: m/z=165.4 (M+H)+

Step 2: N-Cyclopropyl-2-(4-methoxyphenyl)-N-methylimidazo[1,2-a]pyrimidin-7-amine The product was obtained starting from N4-cyclopropyl-N4-methylpyrimidine-2,4-diamine (60 mg, 365 µmol) and 2-bromo-1-(4-methoxyphenyl)ethanone (88 mg, 384 µmol) according to the method described in example 69, step 2 and final trituration with acetone as off-white solid (67 mg, 59%).

MS: M=295.5 (M+H)+

Example 94

7-(Azetidin-1-yl)-2-(4-methylphenyl)imidazo[1,2-a]pyrimidine

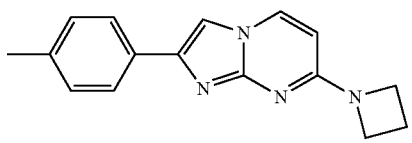 [SMILES: Cc1ccc(-c2cn3ccc(N4CCC4)nc3n2)cc1]

The product was obtained starting from 4-(azetidin-1-yl)pyrimidin-2-amine (60 mg, 400 µmol, example 69, step 1) and 2-bromo-1-p-tolylethanone (90 mg, 422 µmol) according to the method described in example 69, step 2 followed by purification by flash chromatography (using silica gel and a dichloromethane/methanol gradient) and final trituration with ethyl acetate and a few drops of methanol as off-white solid (75 mg, 71%). MS: m/z=265.4 (M+H)+

Example 95

7-(Azetidin-1-yl)-2-(3-methylphenyl)imidazo[1,2-a]pyrimidine

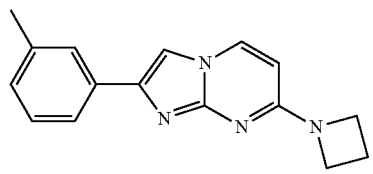

The product was obtained starting from 4-(azetidin-1-yl)pyrimidin-2-amine (60 mg, 400 µmol, example 69, step 1) and 2-bromo-1-m-tolylethanone (90 mg, 422 µmol) according to the method described in example 69, step 2 and final purification by flash chromatography (using silica gel and a dichloromethane/methanol gradient) as light yellow solid (65 mg, 61%).

MS: m/z=265.4 (M+H)+

Example 96

2-[4-(Dimethylamino)phenyl]-N-(2-fluoroethyl)imidazo[1,2-a]pyrimidin-7-amine

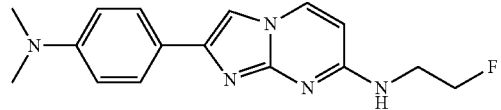 [SMILES: CN(C)c1ccc(-c2cn3ccc(NCCF)nc3n2)cc1]

Step 1: N4-(2-Fluoroethyl)pyrimidine-2,4-diamine

To a yellow suspension of 4-chloropyrimidin-2-amine (0.50 g, 19.3 mmol) in N-methyl-2-pyrrolidinone (3 mL) were added potassium carbonate (2.67 g, 19.3 mmol) and 2-fluoroethanamine hydrochloride (1.15 g, 11.6 mmol). The reaction mixture was heated to 150° C. under microwave irradiation for 10 min. The mixture was poured into ice-water (50 mL) and NaOH (1N, 4 mL) and extracted with ethyl acetate (3×30 mL). The organic layers were combined, dried and evaporated. The product was obtained after purification by flash chromatography (using silica gel and a dichloromethane/methanol/ammonia gradient) as yellow solid (70 mg, 12%). MS: m/z=157.1 (M+H)+

Step 2: 2-[4-(Dimethylamino)phenyl]-N-(2-fluoroethyl)imidazo[1,2-a]pyrimidin-7-amine The product was obtained starting from N4-(2-fluoroethyl)pyrimidine-2,4-diamine (70 mg, 448 µmol) and 2-bromo-1-(4-(dimethylamino)phenyl)ethanone (163 mg, 672 µmol) according to the method described in example 1, step 2 as yellow solid (24 mg, 18%). MS: m/z=300.2 (M+H)+

Example 97

7-(Azetidin-1-yl)-2-[4-(fluoromethoxy)phenyl]imidazo[1,2-a]pyrimidine

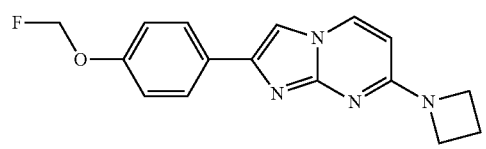 [SMILES: FCOc1ccc(-c2cn3ccc(N4CCC4)nc3n2)cc1]

The product was obtained starting from 4-(7-(azetidin-1-yl)imidazo[1,2-a]pyrimidin-2-yl)phenol (120 mg, 451 µmol, example 80), fluoromethyl 4-methylbenzenesulfonate (129 mg, 631 µmol) and cesium carbonate (294 mg, 901 µmol) according to the method described in example 29 and final purification by flash chromatography (using silica gel and a dichloromethane/methanol gradient) as light brown solid (67 mg, 47%). MS: m/z=299.5 (M+H)+

Example 98

2-Methoxy-4-[7-(methylamino)imidazo[1,2-a]pyrimidin-2-yl]phenol

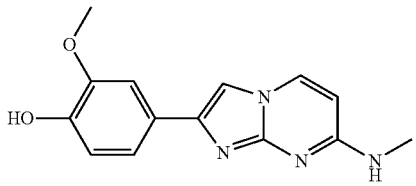 [SMILES: CNc1ccn2cc(-c3ccc(O)c(OC)c3)nc2n1]

The product was obtained starting from N4-methylpyrimidine-2,4-diamine (70 mg, 564 µmol, example 1, step 1) and 2-bromo-1-(4-hydroxy-3-methoxyphenyl)ethanone (200 mg, 818 µmol) according to the method described in example 1, step 2 after increased reaction time (72 h) as orange solid (56 mg, 37%). MS: m/z=271.1 (M+H)+

Example 99

2-(3-Bromophenyl)-N-methylimidazo[1,2-a]pyrimidin-7-amine

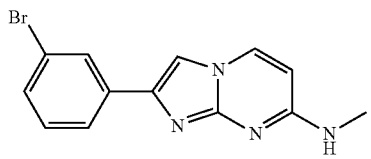 [SMILES: CNc1ccn2cc(-c3cccc(Br)c3)nc2n1]

The product was obtained starting from N4-methylpyrimidine-2,4-diamine (20 mg, 161 µmol, example 1, step 1) and 2-bromo-1-(3-bromophenyl)ethanone (65 mg, 234 µmol) according to the method described in example 1, step 2 after increased reaction time (72 h) as yellow solid (13 mg, 26%). MS: m/z=303.0 (M+H)+

Example 100

7-(4-fluoropiperidin-1-yl)-2-(4-methoxy-2,6-ditritiophenyl)imidazo[1,2-a]pyrimidine

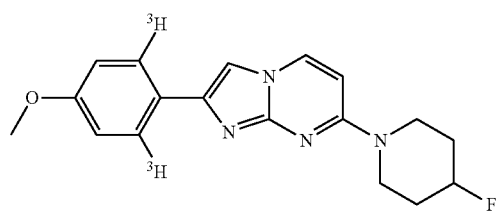 [SMILES: [3H]c1cc(OC)cc([3H])c1-c1cn2ccc(N3CCC(F)CC3)nc2n1]

In a 2 ml tritiation flask, 7-(4-fluoropiperidin-1-yl)-2-(4-methoxyphenyl)imidazo[1,2-a]pyrimidine (2.2 mg, 6.7 µmol) and Crabtree's catalyst (5.2 mg, 6.5 µmol) were dissolved in dichloromethane (1.0 mL). The flask was attached to the tritium manifold (RC-TRITEC) and degassed by freeze-pump-thaw. Tritium gas was introduced, and the light orange solution was vigorously stirred for 4 hours in an atmosphere of tritium at 1200 mbar. The solution was cooled by liquid nitrogen and the excess tritium gas in the reaction vessel was reabsorbed on a uranium-trap for waste-tritium. The solvent was lyophilized off and labile tritium was removed by lyophilization with a 9:1-mixture of ethanol and water (3×1 mL) and toluene (2×1 mL). The remaining brownish oil was dissolved in ethanol (1.5 mL) and transferred on a SCX-2 cation exchanger. Remaining catalyst was eluted with MeOH (10 mL) and discarded, the product was eluted with NH3 in MeOH (3.5 N, 10 mL), collected separately, and concentrated under reduced pressure. The crude product was purified by preparative HPLC (Nucleodur 100-5 Prep C-18, 5 µm, 10×250 mm) using acetonitrile, water, and pH 7 buffer as eluent. 900 MBq (24 mCi) of the title compound were obtained with a radiochemical purity of 94% and a specific activity of 2.1 TBq/mmol (58 Ci/mmol), determined by MS spectrometry. The compound was stored as an ethanolic solution. MS m/z: 331.2 (M+H)+

Example 101

7-(Azetidin-1-yl)-2-[4-(tritritiomethoxy)phenyl)imidazo[1,2-a]pyrimidine

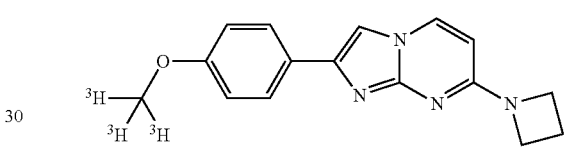

A solution of [$^3$H$_3$]-methylnosylate in toluene (1 mL, 1.85 GBq, 0.66 µmol) was transferred to a 1.5 mL reactor and concentrated under a stream of argon. A solution of 4-[7-(azetidin-1-yl)imidazo[1,2-a]pyrimidin-2-yl]phenol (220 µg, 0.85 µmol) in DMF (0.2 mL) and cesium carbonate (540 µg, 1.6 µmol) were added, and the reactor was tightly closed. The brown solution was stirred at 55° C. for 3 h. The reaction mixture was diluted with dichloromethane (10 mL) and transferred to a 25 mL flask. The solvent and volatile by-products were removed by vacuum transfer. The crude product was purified by preparative HPLC (XBridge C18, 5 µm, 10×250 mm) using acetonitrile, water, and pH 9 buffer as eluent. 150 MBq (4.1 mCi) of the desired compound were obtained with a radiochemical purity of 93% and a specific activity of 2.8 TBq/mmol (76 Ci/mmol). MS m/z: 286.2 (M+H)+

Example 102

2-(3-Methylphenyl)-N-(tritritiomethyl)imidazo[1,2-a]pyrimidine-7-amine

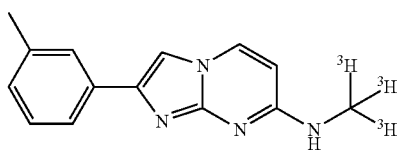

A solution of [$^3$H$_3$]-methylnosylate in toluene (1 mL, 1.85 GBq, 0.66 µmol) was transferred to a 1.5 mL reactor and concentrated under a stream of argon. A solution of 2-(3-methylphenyl)-imidazo[1,2-a]pyrimidine-7-amine (380 µg, 1.7 µmol) in THF (0.24 mL) and cesium carbonate (1400 mg, 4.3 µmol) were added, and the reaction mixture was concentrated to roughly 50 µL. After rinsing with THF (50 µL) the reactor was tightly closed, and the reaction mixture was stirred for 24 h. The reaction mixture was portion wise diluted with dichloromethane (30 mL) and transferred to a 50 mL flask. The solvent and volatile by-products were removed by vacuum transfer. The crude product was purified by preparative HPLC (XBridge C18, 5 µm, 10×250 mm) using acetonitrile, water, and pH 2.5 buffer as eluent. 460 MBq (12.4 mCi) of the desired compound were obtained with a radiochemical purity of 94% and a specific activity of 2.6 TBq/mmol (70 Ci/mmol). MS m/z: 244.9 (M+H)$^+$ Example 103

N-[$^{11}$C]Methyl-2-(m-tolyl)imidazo[1,2-a]pyrimidin-7-amine

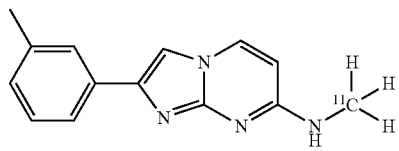 [SMILES: Cc1cccc(-c2cn3ccc(N[11CH3])nc3n2)c1]

Ten minutes prior to the end of [$^{11}$C]carbon dioxide production, the precursor, 2-(m-tolyl)imidazo[1,2-a]pyrimidin-7-amine, (0.7±0.3 mg) was dissolved in 200 µL dimethylsulfoxide and 5 µL 6N sodium hydroxide were added. Carbon-11 methyl iodide ([$^{11}$C]MeI) was produced from starting [$^{11}$C]carbon dioxide via [$^{11}$C]methane in a General Electric FX$_{MeI}$ module. After approximately 10 minutes, [$^{11}$C]MeI was bubbled through the precursor vial. When the radioactivity reached a plateau, the trapping was stopped and the precursor vial was heated at 80° C. for 3 minutes.

The reaction mixture was diluted with 1 mL of HPLC water and injected onto the semipreparative HPLC column (XBridge C-18, 10 µm, 10×150 mm) eluted with 20:80 acetonitrile:water (0.1 M ammonium formate) at 10 mL/min.

The HPLC effluent was monitored at 254 nm and an in-line radioactivity detector. The product, which eluted at approx. 8.5 minutes was collected in 50 mL water containing approx. 250 mg of ascorbic acid. After loading the product onto a conditioned C-18 SepPak Plus, the SepPak was washed with 10 mL of water. The radiolabeled product was eluted from the SepPak with 1 mL of absolute ethanol followed by 10 mL sterile saline through a sterile filter to the final product vial. Aliquots were removed from the final product vial for quality control analysis. Analytical HPLC (XBridge C-18, 3.5 µm, 4.6×100 mm) eluted with 25:75 acetonitrile:pH 7.2 TEA buffer at 2 mL/min monitored at 254 nm was performed to determine radiochemical and chemical purity, specific activity and chemical identity.

The final product, N-[$^{11}$C]methyl-2-(m-tolyl)imidazo[1,2-a]pyrimidin-7-amine, was isolated in an average non-decay corrected yield of 7.5% (n=4) in 32 minutes. The final product average specific radioactivity was 5534 mCi/µmole with an average radiochemical purity of 95.5%.

Example 104

N-Cyclopropyl-2-(4-[$^{11}$C]methoxyphenyl)imidazo[1,2-a]pyrimidin-7-amine

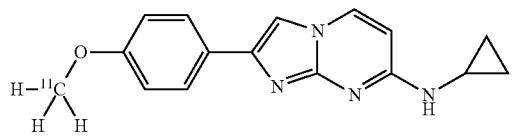 [SMILES: [11CH3]Oc1ccc(-c2cn3ccc(NC4CC4)nc3n2)cc1]

Ten minutes prior to the end of [$^{11}$C]carbon dioxide production, the precursor, 4-[7-(cyclopropylamino)imidazo[1,2-a]pyrimidin-2-yl]phenol, (1.0±0.3 mg) was dissolved in 200 µL dimethylsulfoxide and solid sodium hydride (0.6-1.0 mg) was added. Carbon-11 methyl iodide ([$^{11}$C]MeI) was produced from starting [$^{11}$C]carbon dioxide via [$^{11}$C]methane in a General Electric FX$_{MeI}$ module. After approximately 10 minutes, [$^{11}$C]MeI was bubbled through the precursor vial. When the radioactivity reached a plateau, the trapping was stopped and the precursor vial was heated at 80° C. for 3 minutes.

The reaction mixture was diluted with 200 µL of HPLC solvent and injected onto the semipreparative HPLC column (XBridge C-18, 10 µm, 10×150 mm) eluted with 25:75 absolute ethanol:pH 7.2 TEA buffer at 10 mL/min.

The HPLC effluent was monitored at 254 nm and an in-line radioactivity detector. The product, which eluted at approx. 7 minutes was collected in 50 mL water containing approx. 250 mg of ascorbic acid. After loading the product onto a conditioned Oasis SepPak Plus, the SepPak was washed with 10 mL of water containing approximately 50 mg ascorbic acid. The radiolabeled product was eluted from the Sep Pak with 1 mL of absolute ethanol followed by 10 mL sterile saline through a sterile filter to the final vial.

Aliquots were removed from the final product vial for quality control analysis. Analytical HPLC (XBridge C-18, 3.5 µm, 4.6×100 mm) eluted with 25:75 acetonitrile:pH 7.2 TEA buffer at 2 mL/min monitored at 254 nm was performed to determine radiochemical and chemical purity, specific activity and chemical identity.

The final product, N-cyclopropyl-2-(4-[$^{11}$C]methoxyphenyl)imidazo[1,2-a]pyrimidin-7-amine, was isolated in an average non-decay corrected yield of 7.3% (n=4) in 33.5 minutes. The final product average specific radioactivity was 16870 mCi/µmole with an average radiochemical purity of 97.5%.

Example 105

2-[4-(2-[$^{18}$F]Fluoroethoxy)phenyl]-N-methyl-imidazo[1,2-a]pyrimidin-7-amine

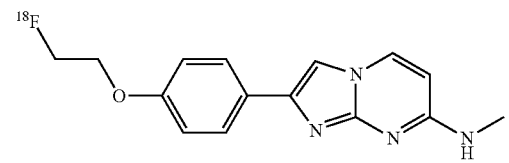 [SMILES: CNc1ccn2cc(-c3ccc(OCC[18F])cc3)nc2n1]

The precursor, 2-[4-[7-(methylamino)imidazo[1,2-a]pyrimidin-2-yl]phenoxy]ethyl 4-methylbenzenesulfonate (2±0.5 mg), was dissolved in 400 μL dimethylsulfoxide prior to end of bombardment (EOB). At EOB, the aqueous [$^{18}$F]fluoride ion, produced by proton bombardment of [$^{18}$O]-enriched water, was trapped on an ion exchange column. The ion exchange column was eluted with 150 μL of a stock solution of Krytpofix 2.2.2/potassium carbonate (48 mg of Kryptofix 2.2.2 and 10 mg potassium carbonate dissolved in 600 μL of 1:1 acetonitrile:water) into the reaction vial followed by 250 μL acetonitrile. The fluoride solution was evaporated to dryness at 110° C. via nitrogen flow and further dried azeotropically by two additions of acetonitrile (250 μL each). The reaction vial was remotely transferred to the microwave cavity (Resonance Instruments) and cooled with compressed air for 2 minutes. The precursor was added and then microwaved at 50 watts for 80 seconds after which the solution was quenched with 1 mL of water.

The reaction mixture was injected onto the semi-preparative HPLC column (XBridge C18, 10 μm, 10×150 mm) eluted with 30:70 methanol:triethylamine buffer (pH 7.2) at 15 mL/min.

The HPLC effluent was monitored at 254 nm and an in-line radioactivity detector. The semipreparative chromatogram was observed (chromatogram shown below) and the 2-[4-(2-[$^{18}$F]fluoroethoxy)phenyl]-N-methyl-imidazo[1,2-a]pyrimidin-7-amine product peak was collected in 50 mL of water containing 250 mg ascorbic acid and reformulated using an automated SPE module. The product solution was eluted through a Waters Oasis Plus SPE, washed with 10 mL of Milli-Q water, then eluted with 1 mL of absolute ethanol and followed by 10 mL of normal saline into the final product vial via a 0.22 μm Millipore FG sterilizing filter.

Aliquots were removed from the final product vial for quality control analysis. Analytical HPLC (XBridge C18, 3.5 μm, 4.6×100 mm) eluted with 20:80 acetonitrile:TEA buffer (pH 7.2) at 2 mL/min monitored at 254 nm was performed to determine radiochemical and chemical purity, specific activity and chemical identity. An analytical chromatogram is displayed below.

The 40-minute radiosynthesis of 2-[4-(2-[$^{18}$F]fluoroethoxy)phenyl]-N-methyl-imidazo[1,2-a]pyrimidin-7-amine produced a final product of 145 mCi, 12.5% (n=1) non-decay corrected yield. The final product had a specific radioactivity of 49,751 mCi/μmole and radiochemical purity of 96%.

Example 106

7-(4-Fluoropiperidin-1-yl)-2-(pyrazin-2-yl)imidazo[1,2-a]pyrimidine

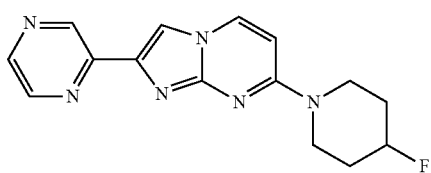 [SMILES: FC1CCN(c2ccn3cc(-c4cnccn4)nc3n2)CC1]

The product was obtained starting from 4-(4-fluoropiperidin-1-yl)pyrimidin-2-amine and 2-bromo-1-(pyrazin-2-yl)ethanone hydrobromide instead of 1-(benzo[d]thiazol-2-yl)-2-bromoethanone according to the method described for example 79 as light yellow solid (25 mg, 31%). MS: m/z=299.5 (M+H)$^+$ Example 107

[4-[7-(Methylamino)imidazo[1,2-a]pyrimidin-2-yl]phenyl]methanol acetic acid adduct

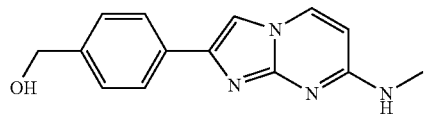 [SMILES: CNc1ccn2cc(-c3ccc(CO)cc3)nc2n1]

To a solution of 4-(7-methylamino-imidazo[1,2-a]pyrimidin-2-yl)-benzoic acid methyl ester (100 mg, 0.35 mmol, example 136) in THF (5 mL) was added diisobutylaluminum hydride (2 M solution in toluene; 0.35 mL, 0.708 mmol) at 0° C., and the reaction mixture was stirred at 25° C. for 1 h. To this mixture was added again diisobutylaluminum hydride (2 M solution in toluene; 0.885 mL, 1.77 mmol) at 0° C., and the mixture was stirred at 25° C. for 30 min. The mixture was quenched with saturated aqueous NH$_4$Cl solution and the solvent was evaporated in vacuo. The crude product was extracted with 30% MeOH in dichloromethane. The organic layer was washed with brine (20 mL), dried over anhydrous Na$_2$SO$_4$, filtered, and evaporated in vacuo. The crude product was purified by prep HPLC to give the product as white sticky liquid (30 mg, 33%). MS: m/z=254.8 (M+H)$^+$ Example 108

2-(3-Fluoro-4-methoxyphenyl)-N-methylimidazo[1,2-a]pyrimidin-7-amine

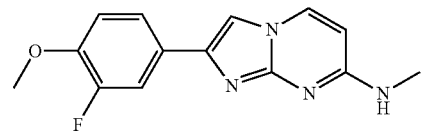

The product was obtained starting from N4-methylpyrimidine-2,4-diamine and 2-bromo-1-(3-fluoro-4-methoxyphenyl)ethanone instead of 2-bromo-1-phenylethanone according to the method described in example 1, step 2 as a white solid (65 mg, 45%). MS: m/z=273.1 (M+H)$^+$ Example 109

N-(4-(7-(Methylamino)imidazo[1,2-a]pyrimidin-2-yl)phenyl)acetamide

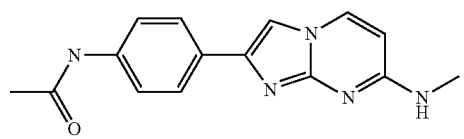 [SMILES: CNc1ccn2cc(-c3ccc(NC(C)=O)cc3)nc2n1]

The product was obtained starting from N4-methylpyrimidine-2,4-diamine and N-(4-(2-bromoacetyl)phenyl)acetamide instead of 2-bromo-1-phenylethanone according to the method described in example 1, step 2 as a white solid (70 mg, 48%). MS: m/z=282.1 (M+H)+

Example 110

5-(7-(Methylamino)imidazo[1,2-a]pyrimidin-2-yl)indolin-2-one

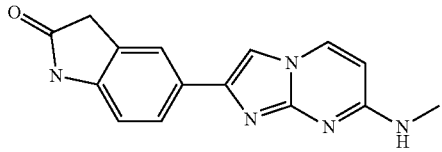 [SMILES: CNc1ccn2cc(-c3ccc4c(c3)CC(=O)N4)nc2n1]

The product was obtained starting from N4-methylpyrimidine-2,4-diamine and 5-(2-bromoacetyl)indolin-2-one instead of 2-bromo-1-phenylethanone according to the method described in example 1, step 2 as a light brown solid (137 mg, 93%). MS: m/z=280.1 (M+H)+

Example 111

7-(Azetidin-1-yl)-2-(4-(2-fluoroethoxy)phenyl)imidazo[1,2-a]pyrimidine

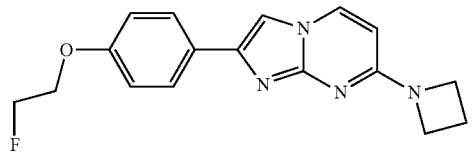 [SMILES: FCCOc1ccc(-c2cn3ccc(N4CCC4)nc3n2)cc1]

Step 1) 4-[7-(Azetidin-1-yl)imidazo[1,2-a]pyrimidin-2-yl]phenol

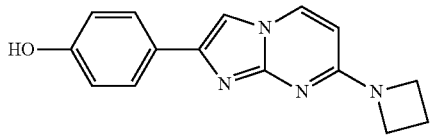 [SMILES: Oc1ccc(-c2cn3ccc(N4CCC4)nc3n2)cc1]

The product was obtained starting from 4-(azetidin-1-yl)pyrimidin-2-amine and 2-bromo-1-(4-hydroxyphenyl)ethanone instead of 2-bromo-1-(4-methoxyphenyl)ethanone according to the method described in example 69, step 2 as a light yellow solid (302 mg, 77%). MS: m/z=267.4 (M+H)+

Step 2) 7-(Azetidin-1-yl)-2-(4-(2-fluoroethoxy)phenyl)imidazo[1,2-a]pyrimidine

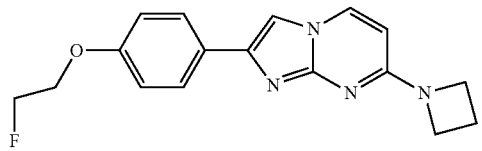 [SMILES: FCCOc1ccc(-c2cn3ccc(N4CCC4)nc3n2)cc1]

The product was obtained starting from 4-[7-(azetidin-1-yl)imidazo[1,2-a]pyrimidin-2-yl]phenol instead of 3-(7-(pyrrolidin-1-yl)imidazo[1,2-a]pyrimidin-2-yl)phenol and 1-bromo-2-fluoroethane according to the method described in example 16, step 3 as light brown solid (73 mg, 50%). MS: m/z=313.6 (M+H)+

Example 112

7-(Azetidin-1-yl)-2-(4-(3-fluoropropoxy)phenyl)imidazo[1,2-a]pyrimidine

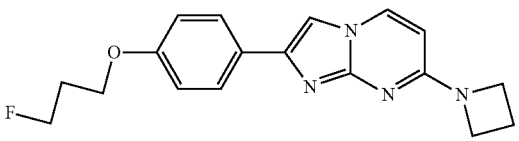 [SMILES: FCCCOc1ccc(-c2cn3ccc(N4CCC4)nc3n2)cc1]

The product was obtained starting from 4-[7-(azetidin-1-yl)imidazo[1,2-a]pyrimidin-2-yl]phenol instead of 3-(7-(pyrrolidin-1-yl)imidazo[1,2-a]pyrimidin-2-yl)phenol and 1-fluoro-3-iodopropane instead of 1-bromo-2-fluoroethane according to the method described in example 16, step 3 as an off-white solid (18 mg, 10%). MS: m/z=327.6 (M+H)+

Example 113

7-(Azetidin-1-yl)-2-(3-methoxyphenyl)imidazo[1,2-a]pyrimidine

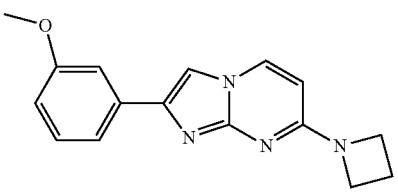 [SMILES: COc1cccc(-c2cn3ccc(N4CCC4)nc3n2)c1]

The product was obtained starting from 4-(azetidin-1-yl)pyrimidin-2-amine and 2-bromo-1-(3-methoxyphenyl)ethanone instead of 2-bromo-1-(4-methoxyphenyl)ethanone according to the method described in example 69, step 2 as an off-white solid (18 mg, 15%). MS: m/z=281.6 (M+H)+

Example 114

[3-[7-(Methylamino)imidazo[1,2-a]pyrimidin-2-yl]phenyl]methanol acetic acid adduct

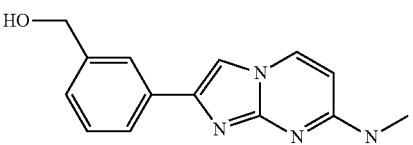

Step 1) Methyl 3-[7-(methylamino)imidazo[1,2-a]pyrimidin-2-yl]benzoate

The product was obtained according to the method described in example 136 starting from N4-methyl-pyrimidine-2,4-diamine (200 mg, 1.63 mmol, example 1, step 1) and 3-(2-bromo-acetyl)-benzoic acid methyl ester (1.5 g, 6.04 mmol) as white solid (135 mg, 12%). MS: m/z=283.0 (M+H)$^+$ Step 2) [3-[7-(Methylamino)imidazo[1,2-a]pyrimidin-2-yl]phenyl]methanol acetic acid adduct The product was obtained according to the method described in example 107 starting from methyl 3-[7-(methylamino)imidazo[1,2-a]pyrimidin-2-yl]benzoate (135 mg, 0.478 mmol) as brown solid (45 mg, 37%). MS: m/z=254.8 (M+H)$^+$ Example 115

7-(Azetidin-1-yl)-2-(3-(2-fluoroethoxy)phenyl)imidazo[1,2-a]pyrimidine

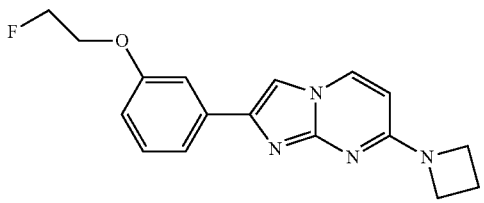 [SMILES: FCCOc1cccc(-c2cn3ccc(N4CCC4)nc3n2)c1]

Step 1) 3-[7-(Azetidin-1-yl)imidazo[1,2-a]pyrimidin-2-yl]phenol

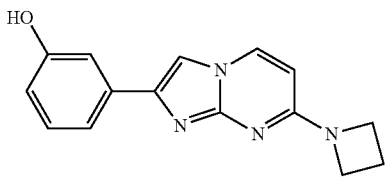 [SMILES: Oc1cccc(-c2cn3ccc(N4CCC4)nc3n2)c1]

The product was obtained starting from 4-(azetidin-1-yl)pyrimidin-2-amine and 2-bromo-1-(3-hydroxyphenyl)ethanone instead of 2-bromo-1-(4-methoxyphenyl)ethanone according to the method described in example 69, step 2 as an off-white solid (445 mg, 67%). MS: m/z=267.5 (M+H)$^+$ Step 2) 7-(Azetidin-1-yl)-2-(3-(2-fluoroethoxy)phenyl)imidazo r[1,2-a]pyrimidine

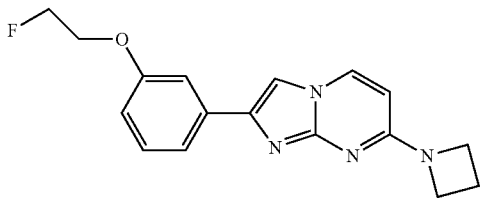 [SMILES: FCCOc1cccc(-c2cn3ccc(N4CCC4)nc3n2)c1]

The product was obtained starting from 3-[7-(azetidin-1-yl)imidazo[1,2-a]pyrimidin-2-yl]phenol instead of 3-(7-(pyrrolidin-1-yl)imidazo[1,2-a]pyrimidin-2-yl)phenol and 1-bromo-2-fluoroethane according to the method described in example 16, step 3 as light yellow solid (76 mg, 58%). MS: m/z=313.6 (M+H)$^+$ Example 116

N-Cyclopropyl-N-(2-fluoroethyl)-2-(4-methoxyphenyl)imidazo[1,2-a]pyrimidin-7-amine

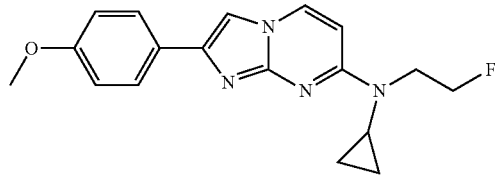 [SMILES: COc1ccc(-c2cn3ccc(N(CCF)C4CC4)nc3n2)cc1]

In a 25 mL round-bottomed flask, N-cyclopropyl-2-(4-methoxyphenyl)imidazo[1,2-a]pyrimidin-7-amine (0.095 g, 305 µmol, example 76) was dissolved in 2.0 mL DMF. Sodium hydride, 60% dispersion in mineral oil (24 mg, 550 µmol) was added and the reaction mixture was stirred at room temperature for 45 min. Then, 1-bromo-2-fluoroethane (47.6 mg, 28 µL, 375 µmol) was added and the reaction mixture was stirred at room temperature overnight.

Further sodium hydride, 60% dispersion in mineral oil (24 mg, 550 µmol) was added, and the reaction mixture was stirred at room temperature for 30 min. Then, 1-bromo-2-fluoroethane (47.6 mg, 28 µL, 375 µmol) was added and the reaction mixture was stirred at room temperature for 3 h. The reaction mixture was quenched with water and extracted with ethyl acetate. The aqueous layer was extracted back with ethyl acetate. The organic layers were washed twice with water and once with brine. The organic layers were combined, dried over sodium sulfate, filtered and concentrated. Purification by flash chromatography (dichloromethane:methanol=100:0 to 95:5) afforded the title compound (41 mg, 39%) as a light yellow solid. MS: m/z=327.5 (M+H)$^+$ Example 117

2-(3-Methoxyphenyl)-N-methylimidazo[1,2-a]pyrimidin-7-amine

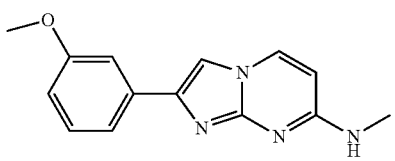

The product was obtained starting from N4-methylpyrimidine-2,4-diamine and 2-bromo-1-(3-methoxyphenyl)ethanone instead of 2-bromo-1-phenylethanone according to the method described in example 1, step 2 as white solid (93 mg, 73%). MS: m/z=255.6 (M+H)$^+$

Example 118

7-(Azetidin-1-yl)-2-(3-(fluoromethoxy)phenyl)imidazo[1,2-a]pyrimidine

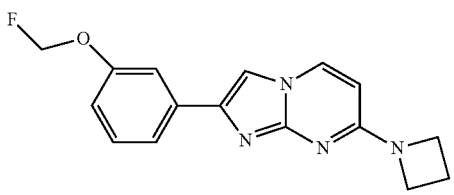 [SMILES: FCOc1cccc(-c2cn3ccc(N4CCC4)nc3n2)c1]

The product was obtained starting from 3-(7-(azetidin-1-yl)imidazo[1,2-a]pyrimidin-2-yl)phenol and fluoromethyl 4-methylbenzenesulfonate according to the method described in example 29 as yellow solid (34 mg, 19%). MS: m/z=299.6 (M+H)+

Example 119

7-(Azetidin-1-yl)-2-(4-fluorophenyl)imidazo[1,2-a]pyrimidine

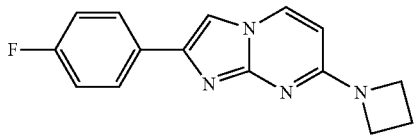 [SMILES: Fc1ccc(-c2cn3ccc(N4CCC4)nc3n2)cc1]

The product was obtained starting from 4-(azetidin-1-yl)pyrimidin-2-amine and 2-bromo-1-(4-fluorophenyl)ethanone instead of 2-bromo-1-(4-methoxyphenyl)ethanone according to the method described in example 69, step 2 as an off-white yellow solid (61 mg, 54%). MS: m/z=269.5 (M+H)+

Example 120

7-(Azetidin-1-yl)-2-(3-fluorophenyl)imidazo[1,2-a]pyrimidine

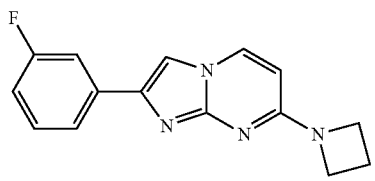 [SMILES: Fc1cccc(-c2cn3ccc(N4CCC4)nc3n2)c1]

The product was obtained starting from 4-(azetidin-1-yl)pyrimidin-2-amine and 2-bromo-1-(3-fluorophenyl)ethanone instead of 2-bromo-1-(4-methoxyphenyl)ethanone according to the method described in example 69, step 2 as a light yellow solid (58 mg, 58%). MS: m/z=269.5 (M+H)+

Example 121

7-(Azetidin-1-yl)-2-(3,5-dimethoxyphenyl)imidazo[1,2-a]pyrimidine

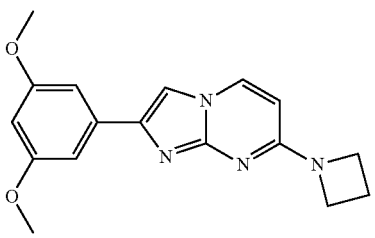 [SMILES: COc1cc(OC)cc(-c2cn3ccc(N4CCC4)nc3n2)c1]

The product was obtained starting from 4-(azetidin-1-yl)pyrimidin-2-amine and 2-bromo-1-(3,5-dimethoxyphenyl)ethanone instead of 2-bromo-1-(4-methoxyphenyl)ethanone according to the method described in example 69, step 2 as a white solid (55 mg, 46%). MS: m/z=311.5 (M+H)+

Example 122

4-(7-(Methylamino)imidazo[1,2-a]pyrimidin-2-yl)phenol

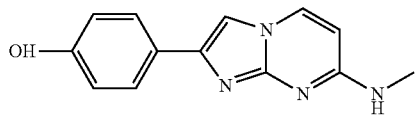

The product was obtained starting from N4-methylpyrimidine-2,4-diamine and 2-bromo-1-(4-hydroxyphenyl)ethanone instead of 2-bromo-1-phenylethanone according to the method described in example 1, step 2 as a yellow solid (647 mg, 91%). MS: m/z=241.6 (M+H)+

Example 123

2-(4-(2-Fluoroethoxy)phenyl)-N-methylimidazo[1,2-a]pyrimidin-7-amine

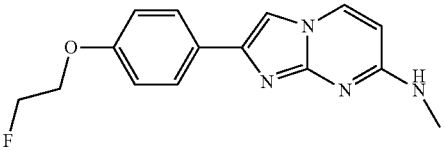 [SMILES: CNc1ccn2cc(-c3ccc(OCCF)cc3)nc2n1]

The product was obtained starting from 4-(7-(methylamino)imidazo[1,2-a]pyrimidin-2-yl)phenol instead of 3-(7-(pyrrolidin-1-yl)imidazo[1,2-a]pyrimidin-2-yl)phenol and 1-bromo-2-fluoroethane according to the method described in example 16, step 3 as yellow solid (75 mg, 43%). MS: m/z=287.6 (M+H)+

Example 124

2-(4-(3-Fluoropropoxy)phenyl)-N-methylimidazo[1,2-a]pyrimidin-7-amine

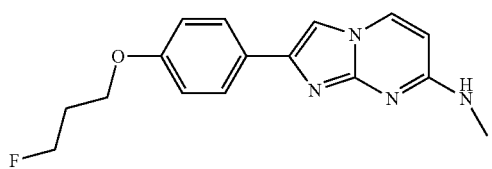 [SMILES: CNc1ccn2cc(-c3ccc(OCCCF)cc3)nc2n1]

The product was obtained starting from 4-(7-(methylamino)imidazo[1,2-a]pyrimidin-2-yl)phenol instead of 3-(7-(pyrrolidin-1-yl)imidazo[1,2-a]pyrimidin-2-yl)phenol and 1-fluoro-3-iodopropane instead of 1-bromo-2-fluoroethane according to the method described in example 16, step 3 as a light yellow solid (73 mg, 42%). MS: m/z=301.6 (M+H)$^+$

Example 125

3-(7-(Methylamino)imidazo[1,2-a]pyrimidin-2-yl)phenol

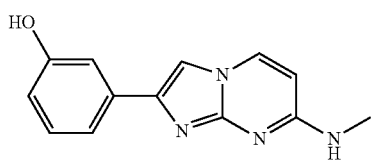 [SMILES: CNc1ccn2cc(-c3cccc(O)c3)nc2n1]

The product was obtained starting from N4-methylpyrimidine-2,4-diamine and 2-bromo-1-(3-hydroxyphenyl)ethanone instead of 2-bromo-1-phenylethanone according to the method described in example 1, step 2 as a yellow solid (185 mg, 59%). MS: m/z=241.6 (M+H)$^+$

Example 126

7-(Azetidin-1-yl)-2-(3-(methylthio)phenyl)imidazo[1,2-a]pyrimidine

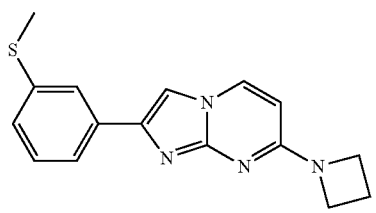 [SMILES: CSc1cccc(-c2cn3ccc(N4CCC4)nc3n2)c1]

The product was obtained starting from 4-(azetidin-1-yl)pyrimidin-2-amine and 2-bromo-1-(3-(methylthio)phenyl)ethanone instead of 2-bromo-1-(4-methoxyphenyl)ethanone according to the method described in example 69, step 2 as an off-white solid (53 mg, 44%). MS: m/z=297.5 (M+H)$^+$

Example 127

7-(Azetidin-1-yl)-2-(3-methoxy-4-methylphenyl)imidazo[1,2-a]pyrimidine

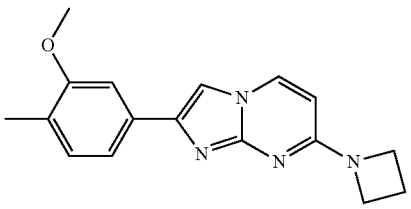 [SMILES: COc1cc(-c2cn3ccc(N4CCC4)nc3n2)ccc1C]

The product was obtained starting from 4-(azetidin-1-yl)pyrimidin-2-amine and 2-bromo-1-(3-methoxy-4-methylphenyl)ethanone instead of 2-bromo-1-(4-methoxyphenyl)ethanone according to the method described in example 69, step 2 as an off-white solid (6 mg, 5%). MS: m/z=295.5 (M+H)$^+$

Example 128

7-(Azetidin-1-yl)-2-(3,4-dimethoxyphenyl)imidazo[1,2-a]pyrimidine

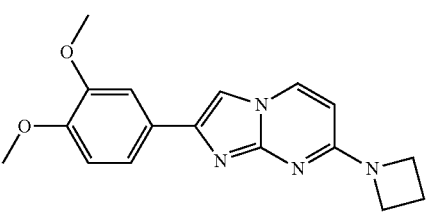 [SMILES: COc1ccc(-c2cn3ccc(N4CCC4)nc3n2)cc1OC]

The product was obtained starting from 4-(azetidin-1-yl)pyrimidin-2-amine and 2-bromo-1-(3,4-dimethoxyphenyl)ethanone instead of 2-bromo-1-(4-methoxyphenyl)ethanone according to the method described in example 69, step 2 as an off-white solid (21 mg, 18%). MS: m/z=311.5 (M+H)$^+$

Example 129

2-(3-(2-Fluoroethoxy)phenyl)-N-methylimidazo[1,2-a]pyrimidin-7-amine

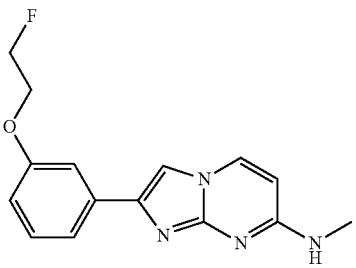 [SMILES: CNc1ccn2cc(-c3cccc(OCCF)c3)nc2n1]

The product was obtained starting from 3-(7-(methylamino)imidazo[1,2-a]pyrimidin-2-yl)phenol instead of 3-(7-(pyrrolidin-1-yl)imidazo[1,2-a]pyrimidin-2-yl)phenol and 1-bromo-2-fluoroethane according to the method described in example 16, step 3 as an off-white solid (23 mg, 18%). MS: m/z=287.6 (M+H)+

Example 130

2-(3-(3-Fluoropropoxy)phenyl)-N-methylimidazo[1,2-a]pyrimidin-7-amine

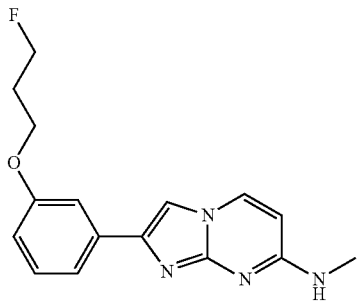

The product was obtained starting from 3-(7-(methylamino)imidazo[1,2-a]pyrimidin-2-yl)phenol instead of 3-(7-(pyrrolidin-1-yl)imidazo[1,2-a]pyrimidin-2-yl)phenol and 1-fluoro-3-iodopropane instead of 1-bromo-2-fluoroethane according to the method described in example 16, step 3 as a white solid (29 mg, 21%). MS: m/z=301.6 (M+H)+

Example 131

2-(3-(Fluoromethoxy)phenyl)-N-methylimidazo[1,2-a]pyrimidin-7-amine

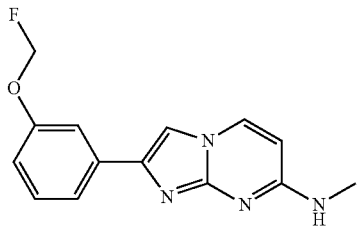

The product was obtained starting from 3-(7-(methylamino)imidazo[1,2-a]pyrimidin-2-yl)phenol instead of 3-(7-(azetidin-1-yl)imidazo[1,2-a]pyrimidin-2-yl)phenol and fluoromethyl 4-methylbenzenesulfonate according to the method described in example 29 as a white solid (61 mg, 34%). MS: m/z=273.5 (M+H)+

Example 132

2-(4-(Fluoromethoxy)phenyl)-N-methylimidazo[1,2-a]pyrimidin-7-amine

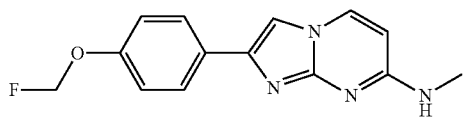 [SMILES: CNc1ccn2cc(-c3ccc(OCF)cc3)nc2n1]

The product was obtained starting from 4-(7-(methylamino)imidazo[1,2-a]pyrimidin-2-yl)phenol instead of 3-(7-(azetidin-1-yl)imidazo[1,2-a]pyrimidin-2-yl)phenol and fluoromethyl 4-methylbenzenesulfonate according to the method described in example 29 as a white solid (36 mg, 20%). MS: m/z=273.5 (M+H)+

Example 133

3-(7-(Cyclopropylamino)imidazo[1,2-a]pyrimidin-2-yl)phenol

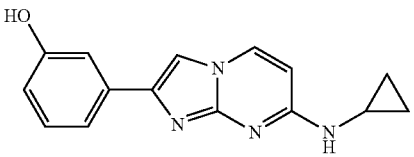 [SMILES: Oc1cccc(-c2cn3ccc(NC4CC4)nc3n2)c1]

The product was obtained starting from N4-cyclopropylpyrimidine-2,4-diamine instead of 4-(azetidin-1-yl)pyrimidin-2-amine and 2-bromo-1-(3-hydroxyphenyl)ethanone instead of 2-bromo-1-(4-methoxyphenyl)ethanone according to the method described in example 69, step 2 as a light yellow solid (594 mg, 98%). MS: m/z=267.6 (M+H)+

Example 134

N-Cyclopropyl-2-(3-(2-fluoroethoxy)phenyl)imidazo[1,2-a]pyrimidin-7-amine

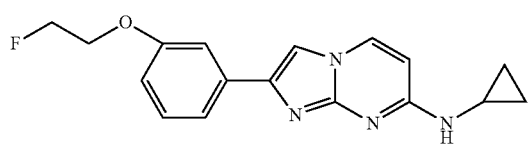 [SMILES: FCCOc1cccc(-c2cn3ccc(NC4CC4)nc3n2)c1]

The product was obtained starting from 3-(7-(cyclopropylamino)imidazo[1,2-a]pyrimidin-2-yl)phenol instead of 3-(7-(pyrrolidin-1-yl)imidazo[1,2-a]pyrimidin-2-yl)phenol and 1-bromo-2-fluoroethane according to the method described in example 16, step 3 as an off-white solid (43 mg, 29%). MS: m/z=313.6 (M+H)+

Example 135

[4-[7-(Dimethylamino)imidazo[1,2-a]pyrimidin-2-yl]phenyl]methanol acetic acid adduct

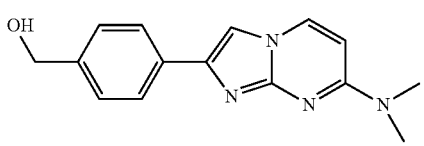 [SMILES: CN(C)c1ccn2cc(-c3ccc(CO)cc3)nc2n1]

Step 1) Methyl 4-[7-(dimethylamino)imidazo[1,2-a]pyrimidin-2-yl]benzoate

The product was obtained according to the method described in example 136 starting from N4,N4-dimethylpyrimidine-2,4-diamine (500 mg, 3.62 mmol, example 18, step 1) and 4-(2-bromo-acetyl)-benzoic acid methyl ester (1.4 g, 5.44 mmol) as yellow solid (270 mg, 25%). MS: m/z=297.0 (M+H)$^+$ Step 2) [4-[7-(Dimethylamino)imidazo[1,2-a]pyrimidin-2-yl]phenyl]methanol acetic acid adduct The product was obtained according to the method described in example 107 starting from methyl 4-[7-(dimethylamino)imidazo[1,2-a]pyrimidin-2-yl]benzoate (100 mg, 0.337 mmol) as yellow sticky solid (50 mg, 55%). MS: m/z=268.8 (M+H)$^+$ Example 136

Methyl 4-[7-(methylamino)imidazo[1,2-a]pyrimidin-2-yl]benzoate

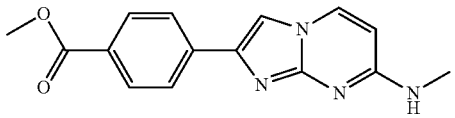

To a solution of N4-methyl-pyrimidine-2, 4-diamine (250 mg, 2.01 mmol, example 1, step 1) in acetone (10 mL) was added 4-(2-bromo-acetyl)-benzoic acid methyl ester (780 mg, 3.021 mmol), and the reaction mixture was allowed to stir for 30 min at 25° C. To this mixture was added p-toluenesulfonic acid (catalytic amount) and the reaction mixture was refluxed for 8 h. All volatiles were removed under reduced pressure and the resultant crude product was quenched with saturated aqueous NaHCO$_3$ solution and extracted with ethyl acetate (2×50 mL). The combined organic layer was washed with brine, dried over anhydrous Na$_2$SO$_4$, filtered, and evaporated in vacuo. The resultant crude product was purified by flash chromatography (using silica gel amine phase and 90% ethyl acetate in hexane) to give the product as off white solid (100 mg, 18%). MS: m/z=283.0 (M+H)$^+$ Example 137

N-Cyclopropyl-2-(3-(fluoromethoxy)phenyl)imidazo[1,2-a]pyrimidin-7-amine

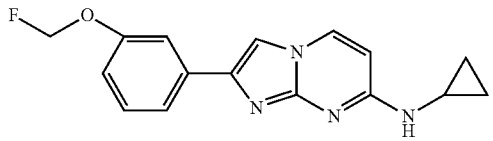 [SMILES: FCOc1cccc(-c2cn3ccc(NC4CC4)nc3n2)c1]

The product was obtained starting from 3-(7-(cyclopropylamino)imidazo[1,2-a]pyrimidin-2-yl)phenol instead of 3-(7-(azetidin-1-yl)imidazo[1,2-a]pyrimidin-2-yl)phenol and fluoromethyl 4-methylbenzenesulfonate according to the method described in example 29 as an off-white solid (49 mg, 33%). MS: m/z=299.6 (M+H)$^+$ Example 138

N-Cyclopropyl-2-(4-(2-fluoroethoxy)phenyl)imidazo[1,2-a]pyrimidin-7-amine

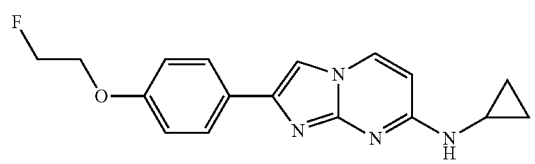 [SMILES: FCCOc1ccc(-c2cn3ccc(NC4CC4)nc3n2)cc1]

The product was obtained starting from 4-(7-(cyclopropylamino)imidazo[1,2-a]pyrimidin-2-yl)phenol hydrobromide instead of 3-(7-(pyrrolidin-1-yl)imidazo[1,2-a]pyrimidin-2-yl)phenol and 1-bromo-2-fluoroethane according to the method described in example 16, step 3 as a light yellow solid (28 mg, 22%). MS: m/z=313.6 (M+H)$^+$ Example 139

N-Cyclopropyl-2-(4-(3-fluoropropoxy)phenyl)imidazo[1,2-a]pyrimidin-7-amine

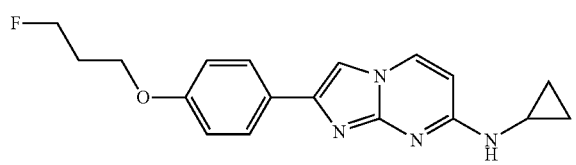 [SMILES: FCCCOc1ccc(-c2cn3ccc(NC4CC4)nc3n2)cc1]

The product was obtained starting from 4-(7-(cyclopropylamino)imidazo[1,2-a]pyrimidin-2-yl)phenol hydrobromide instead of 3-(7-(pyrrolidin-1-yl)imidazo[1,2-a]pyrimidin-2-yl)phenol and 1-fluoro-3-iodopropane instead of 1-bromo-2-fluoroethane according to the method described in example 16, step 3 as a white solid (67 mg, 50%). MS: m/z=327.6 (M+H)$^+$ Example 140

N-Cyclopropyl-2-(4-(fluoromethoxy)phenyl)imidazo[1,2-a]pyrimidin-7-amine

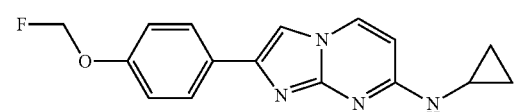

The product was obtained starting from 4-(7-(cyclopropylamino)imidazo[1,2-a]pyrimidin-2-yl)phenol instead of 3-(7-(azetidin-1-yl)imidazo[1,2-a]pyrimidin-2-yl)phenol and fluoromethyl 4-methylbenzenesulfonate according to the method described in example 29 as a yellow solid (52 mg, 46%). MS: m/z=299.6 (M+H)$^+$

Example 141

N-Methyl-2-(4-(methylthio)phenyl)imidazo[1,2-a]pyrimidin-7-amine

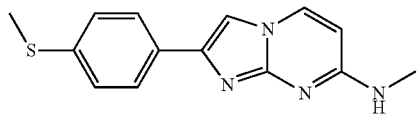

The product was obtained starting from N4-methylpyrimidine-2,4-diamine and 2-bromo-1-(4-(methylthio)phenyl)ethanone instead of 2-bromo-1-phenylethanone according to the method described in example 1, step 2 as an off-white solid (14 mg, 12%). MS: m/z=271.5 (M+H)$^+$

Example 142

2-(3,4-Dimethoxyphenyl)-N-methylimidazo[1,2-a]pyrimidin-7-amine

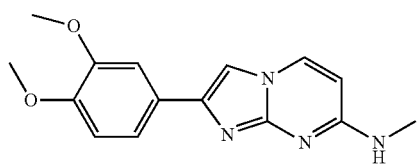

The product was obtained starting from N4-methylpyrimidine-2,4-diamine and 2-bromo-1-(3,4-dimethoxyphenyl)ethanone instead of 2-bromo-1-phenylethanone according to the method described in example 1, step 2 as an off-white solid (20 mg, 18%). MS: m/z=285.5 (M+H)$^+$

Example 143

2-(3-Methoxy-4-methylphenyl)-N-methylimidazo[1,2-a]pyrimidin-7-amine

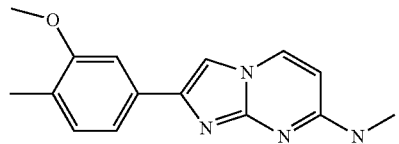

The product was obtained starting from N4-methylpyrimidine-2,4-diamine and 2-bromo-1-(3-methoxy-4-methylphenyl)ethanone instead of 2-bromo-1-phenylethanone according to the method described in example 1, step 2 as an off-white solid (43 mg, 39%). MS: m/z=269.5 (M+H)$^+$

Example 144

2-(3,5-Dimethoxyphenyl)-N-methylimidazo[1,2-a]pyrimidin-7-amine

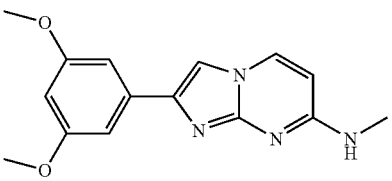

The product was obtained starting from N4-methylpyrimidine-2,4-diamine and 2-bromo-1-(3,5-dimethoxyphenyl)ethanone instead of 2-bromo-1-phenylethanone according to the method described in example 1, step 2 as an off-white solid (33 mg, 30%). MS: m/z=285.5 (M+H)$^+$

We claim:
1. A compound of formula (I)

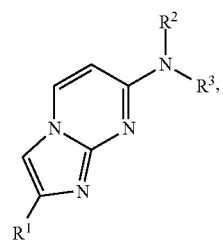

wherein
R$^1$ is (a) phenyl, optionally substituted by one or two substituents selected from $^3$H, halogen, lower alkyl, di-methyl-amino, NHC(O)-lower alkyl, C(O)O-lower alkyl, lower alkoxy, OC($^3$H)$_3$, O$^{11}$CH$_3$, OCH$_2$CH$_2$$^{18}$F, lower alkoxy substituted by halogen, hydroxy, lower alkyl substituted by hydroxy, S-lower alkyl, (b) heterocyclyl group,
R$^2$ is hydrogen, lower alkyl or lower alkyl substituted by halogen;
R$^3$ is lower alkyl, C($^3$H)$_3$, $^{11}$CH$_3$, lower alkyl substituted by halogen, —(CH$_2$)$_2$—O-lower alkyl substituted by halogen or cycloalkyl; or,
R$^2$ and R$^3$ together with the N-atom to which they are attached form a ring comprising —CH$_2$CH$_2$CHRCH$_2$CH$_2$—, —CH$_2$CH$_2$CHRCH$_2$—, —CH$_2$CHRCH$_2$—, —CH$_2$CH$_2$—NR—CH$_2$CH$_2$—, —CH$_2$CH$_2$—O—CH$_2$CH$_2$—, or,

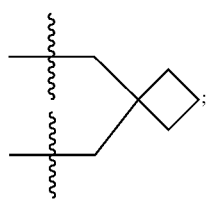 [SMILES: *CC1(C*)CCC1]

R is hydrogen, halogen, lower alkyl substituted by halogen or lower alkoxy;

or a pharmaceutically acceptable acid addition salt, a racemic mixture or its corresponding enantiomer and/or optical isomers thereof.

2. The compound of claim 1 wherein the compound is selected from the group consisting of:

N-methyl-2-phenylimidazo[1,2-a]pyrimidin-7-amine,
7-(4-fluoropiperidin-1-yl)-2-phenylimidazo[1,2-a]pyrimidine,
7-(4-fluoropiperidin-1-yl)-2-(4-methoxyphenyl)imidazo[1,2-a]pyrimidine,
2-(4-chlorophenyl)-7-(4-fluoropiperidin-1-yl)imidazo[1,2-a]pyrimidine,
7-(4-fluoropiperidin-1-yl)-2-(3-methoxyphenyl)imidazo[1,2-a]pyrimidine,
2-(4-fluorophenyl)-7-(4-fluoropiperidin-1-yl)imidazo[1,2-a]pyrimidine,
4-[4-[7-(4-fluoropiperidin-1-yl)imidazo[1,2-a]pyrimidin-2-yl]phenyl]morpholine,
7-(4-fluoropiperidin-1-yl)-2-(3-methylphenyl)imidazo[1,2-a]pyrimidine,
7-(4-fluoropiperidin-1-yl)-2-(4-methylphenyl)imidazo[1,2-a]pyrimidine,
2-(2-fluorophenyl)-7-(4-fluoropiperidin-1-yl)imidazo[1,2-a]pyrimidine,
3-[7-(4-fluoropiperidin-1-yl)imidazo[1,2-a]pyrimidin-2-yl]phenol,
7-(4-fluoropiperidin-1-yl)-2-(4-pyrrolidin-1-ylphenyl)imidazo[1,2-a]pyrimidine,
7-(4-fluoropiperidin-1-yl)-2-[3-(trifluoromethoxy)phenyl]imidazo[1,2-a]pyrimidine,
2-[3-(fluoromethoxy)phenyl]-7-pyrrolidin-1-ylimidazo[1,2-a]pyrimidine,
2-[3-(2-fluoroethoxy)phenyl]-7-pyrrolidin-1-ylimidazo[1,2-a]pyrimidine,
N,N-dimethyl-2-phenylimidazo[1,2-a]pyrimidin-7-amine,
7-[4-(2-fluoroethyl)piperazin-1-yl]-2-(4-methoxyphenyl)imidazo[1,2-a]pyrimidine,
7-[4-(2-fluoroethyl)piperazin-1-yl]-2-(3-methoxyphenyl)imidazo[1,2-a]pyrimidine,
N-(2-fluoroethyl)-N-methyl-2-phenylimidazo[1,2-a]pyrimidin-7-amine,
N-(2-fluoroethyl)-2-(3-methoxyphenyl)-N-methylimidazo[1,2-a]pyrimidin-7-amine,
N-(2-fluoroethyl)-2-(4-methoxyphenyl)-N-methylimidazo[1,2-a]pyrimidin-7-amine,
7-[4-(2-fluoroethyl)piperazin-1-yl]-2-phenylimidazo[1,2-a]pyrimidine,
4-[2-(4-methoxyphenyl)imidazo[1,2-a]pyrimidin-7-yl]morpholine,
4-[2-(3-methylphenyl)imidazo[1,2-a]pyrimidin-7-yl]morpholine,
4-[2-(3,4-dimethoxyphenyl)imidazo[1,2-a]pyrimidin-7-yl]morpholine,
4-(7-pyrrolidin-1-ylimidazo[1,2-a]pyrimidin-2-yl)phenol,
2-[4-(2-fluoroethoxy)phenyl]-7-pyrrolidin-1-ylimidazo[1,2-a]pyrimidine,
2-[4-(fluoromethoxy)phenyl]-7-pyrrolidin-1-ylimidazo[1,2-a]pyrimidine,
7-[(3R)-3-methoxypyrrolidin-1-yl]-2-phenylimidazo[1,2-a]pyrimidine,
7-[(3S)-3-methoxypyrrolidin-1-yl]-2-phenylimidazo[1,2-a]pyrimidine,
7-[(3R)-3-fluoropyrrolidin-1-yl]-2-(4-methoxyphenyl)imidazo[1,2-a]pyrimidine,
7-[(3S)-3-fluoropyrrolidin-1-yl]-2-(4-methoxyphenyl)imidazo[1,2-a]pyrimidine,
2-(3-methoxyphenyl)-N,N-dimethylimidazo[1,2-a]pyrimidin-7-amine,
2-(4-methoxyphenyl)-N,N-dimethylimidazo[1,2-a]pyrimidin-7-amine,
N,N-dimethyl-2-(4-methylphenyl)imidazo[1,2-a]pyrimidin-7-amine,
N,N-dimethyl-2-(3-methylphenyl)imidazo[1,2-a]pyrimidin-7-amine,
4-[2-(3-methoxyphenyl)imidazo[1,2-a]pyrimidin-7-yl]morpholine,
4-[2-(4-methylphenyl)imidazo[1,2-a]pyrimidin-7-yl]morpholine,
2-(4-methoxyphenyl)-7-pyrrolidin-1-ylimidazo[1,2-a]pyrimidine,
2-(4-methylphenyl)-7-pyrrolidin-1-ylimidazo[1,2-a]pyrimidine,
N,N-dimethyl-2-(4-morpholin-4-ylphenyl)imidazo[1,2-a]pyrimidin-7-amine,
2-[4-(dimethylamino)phenyl]-N,N-dimethylimidazo[1,2-a]pyrimidin-7-amine,
2-(3-methoxyphenyl)-7-pyrrolidin-1-ylimidazo[1,2-a]pyrimidine,
2-(3-methylphenyl)-7-pyrrolidin-1-ylimidazo[1,2-a]pyrimidine,
2-(4-methoxyphenyl)-7-piperidin-1-ylimidazo[1,2-a]pyrimidine,
2-(3-methoxyphenyl)-7-piperidin-1-ylimidazo[1,2-a]pyrimidine,
2-(4-methylphenyl)-7-piperidin-1-ylimidazo[1,2-a]pyrimidine,
2-(3-methylphenyl)-7-piperidin-1-ylimidazo[1,2-a]pyrimidine,
2-(3,4-dimethoxyphenyl)-7-piperidin-1-ylimidazo[1,2-a]pyrimidine,
7-[4-(2-fluoroethyl)piperidin-1-yl]-2-phenylimidazo[1,2-a]pyrimidine,
7-[4-(2-fluoroethyl)piperidin-1-yl]-2-(3-methoxyphenyl)imidazo[1,2-a]pyrimidine,
7-[4-(2-fluoroethyl)piperidin-1-yl]-2-(4-methoxyphenyl)imidazo[1,2-a]pyrimidine,
7-[4-(2-fluoroethyl)piperidin-1-yl]-2-(3-methylphenyl)imidazo[1,2-a]pyrimidine,
7-[4-(2-fluoroethyl)piperidin-1-yl]-2-(4-methylphenyl)imidazo[1,2-a]pyrimidine,
4-[4-[7-[4-(2-fluoroethyl)piperidin-1-yl]imidazo[1,2-a]pyrimidin-2-yl]phenyl]morpholine,
N-methyl-2-(3-methylphenyl)imidazo[1,2-a]pyrimidin-7-amine,
N-[2-(2-fluoroethoxy)ethyl]-2-(4-methoxyphenyl)-N-methylimidazo[1,2-a]pyrimidin-7-amine,
7-(2-azaspiro[3.3]heptan-2-yl)-2-(4-methoxyphenyl)imidazo[1,2-a]pyrimidine,
N-ethyl-2-(4-methoxyphenyl)-N-methylimidazo[1,2-a]pyrimidin-7-amine,
N,N-diethyl-2-(4-methoxyphenyl)imidazo[1,2-a]pyrimidin-7-amine,
N-[2-(2-fluoroethoxy)ethyl]-N-methyl-2-(3-methylphenyl)imidazo[1,2-a]pyrimidin-7-amine,
7-(azetidin-1-yl)-2-(4-methoxyphenyl)imidazo[1,2-a]pyrimidine,
7-(3-fluoroazetidin-1-yl)-2-(4-methoxyphenyl)imidazo[1,2-a]pyrimidine,
7-(3-fluoroazetidin-1-yl)-2-phenylimidazo[1,2-a]pyrimidine, 7-(3-fluoroazetidin-1-yl)-2-(3-methylphenyl)imidazo[1,2-a]pyrimidine,
N,N-dimethyl-4-(7-morpholin-4-ylimidazo[1,2-a]pyrimidin-2-yl)aniline,
N-cyclopropyl-2-(4-methoxyphenyl)imidazo[1,2-a]pyrimidin-7-amine,
N-isopropyl-2-(4-methoxy-phenyl)-imidazo[1,2-a]pyrimidin-7-amine,
2-(4-methoxyphenyl)-N-(2,2,2-trifluoroethyl)imidazo[1,2-a]pyrimidin-7-amine,
4-[7-(azetidin-1-yl)imidazo[1,2-a]pyrimidin-2-yl]phenol,
7-(3-methoxyazetidin-1-yl)-2-(4-methoxyphenyl)imidazo[1,2-a]pyrimidine,
N-methyl-2-(4-methylphenyl)imidazo[1,2-a]pyrimidin-7-amine,
2-(4-methoxyphenyl)-N-methylimidazo[1,2-a]pyrimidin-7-amine,
N-(2-fluoroethyl)-N-methyl-2-(4-methylphenyl)imidazo[1,2-a]pyrimidin-7-amine,
N-(2-fluoroethyl)-N-methyl-2-(3-methylphenyl)imidazo[1,2-a]pyrimidin-7-amine,
2-(4-methoxyphenyl)-7-(3-methylazetidin-1-yl)imidazo[1,2-a]pyrimidine,
2-[4-(dimethylamino)phenyl]-N-methylimidazo[1,2-a]pyrimidin-7-amine,
4-[7-(4-fluoropiperidin-1-yl)imidazo[1,2-a]pyrimidin-2-yl]-N,N-dimethylaniline,
2-[4-(dimethylamino)phenyl]-N-(2-fluoroethyl)-N-methylimidazo[1,2-a]pyrimidin-7-amine,
N-cyclopropyl-2-(4-methoxyphenyl)-N-methylimidazo[1,2-a]pyrimidin-7-amine,
7-(azetidin-1-yl)-2-(4-methylphenyl)imidazo[1,2-a]pyrimidine,
7-(azetidin-1-yl)-2-(3-methylphenyl)imidazo[1,2-a]pyrimidine,
2-[4-(dimethylamino)phenyl]-N-(2-fluoroethyl)imidazo[1,2-a]pyrimidin-7-amine,
7-(azetidin-1-yl)-2-[4-(fluoromethoxy)phenyl]imidazo[1,2-a]pyrimidine,
2-methoxy-4-[7-(methylamino)imidazo[1,2-a]pyrimidin-2-yl]phenol,
2-(3-bromophenyl)-N-methylimidazo[1,2-a]pyrimidin-7-amine,
7-(4-fluoropiperidin-1-yl)-2-(4-methoxy-2,6-ditritiophenyl)imidazo[1,2-a]pyrimidine,
7-(azetidin-1-yl)-2-[4-(tritritiomethoxy)phenyl]imidazo[1,2-a]pyrimidine,
2-(3-methylphenyl)-N-(tritritiomethyl)imidazo[1,2-a]pyrimidine-7-amine,
N-[$^{11}$C]methyl-2-(m-tolyl)imidazo[1,2-a]pyrimidin-7-amine,
N-cyclopropyl-2-(4-[$^{11}$C]methoxyphenyl)imidazo[1,2-a]pyrimidin-7-amine,
2-[4-(2-[$^{18}$F]fluoroethoxy)phenyl]-N-methyl-imidazo[1,2-a]pyrimidin-7-amine,
[4-[7-(methylamino)imidazo[1,2-a]pyrimidin-2-yl]phenyl]methanol,
2-(3-fluoro-4-methoxyphenyl)-N-methylimidazo[1,2-a]pyrimidin-7-amine,
N-(4-(7-(methylamino)imidazo[1,2-a]pyrimidin-2-yl)phenyl)acetamide,
7-(azetidin-1-yl)-2-(4-(2-fluoroethoxy)phenyl)imidazo[1,2-a]pyrimidine,
7-(azetidin-1-yl)-2-(4-(3-fluoropropoxy)phenyl)imidazo[1,2-a]pyrimidine,
7-(azetidin-1-yl)-2-(3-methoxyphenyl)imidazo[1,2-a]pyrimidine,
[3-[7-(methylamino)imidazo[1,2-a]pyrimidin-2-yl]phenyl]methanol,
7-(azetidin-1-yl)-2-(3-(2-fluoroethoxy)phenyl)imidazo[1,2-a]pyrimidine,
N-cyclopropyl-N-(2-fluoroethyl)-2-(4-methoxyphenyl)imidazo[1,2-a]pyrimidin-7-amine,
2-(3-methoxyphenyl)-N-methylimidazo[1,2-a]pyrimidin-7-amine,
7-(azetidin-1-yl)-2-(3-(fluoromethoxy)phenyl)imidazo[1,2-a]pyrimidine,
7-(azetidin-1-yl)-2-(4-fluorophenyl)imidazo[1,2-a]pyrimidine,
7-(azetidin-1-yl)-2-(3-fluorophenyl)imidazo[1,2-a]pyrimidine,
7-(azetidin-1-yl)-2-(3,5-dimethoxyphenyl)imidazo[1,2-a]pyrimidine,
4-(7-(methylamino)imidazo[1,2-a]pyrimidin-2-yl)phenol,
2-(4-(2-fluoroethoxy)phenyl)-N-methylimidazo[1,2-a]pyrimidin-7-amine,
2-(4-(3-fluoropropoxy)phenyl)-N-methylimidazo[1,2-a]pyrimidin-7-amine,
3-(7-(methylamino)imidazo[1,2-a]pyrimidin-2-yl)phenol,
7-(azetidin-1-yl)-2-(3-(methylthio)phenyl)imidazo[1,2-a]pyrimidine,
7-(azetidin-1-yl)-2-(3-methoxy-4-methylphenyl)imidazo[1,2-a]pyrimidine,
7-(azetidin 1-yl)-2-(3,4-dimethoxyphenyl)imidazo[1,2-a]pyrimidine,
2-(3-(2-fluoroethoxy)phenyl)-N-methylimidazo[1,2-a]pyrimidin-7-amine,
2-(3-(3-fluoropropoxy)phenyl)-N-methylimidazo[1,2-a]pyrimidin-7-amine,
2-(3-(fluoromethoxy)phenyl)-N-methylimidazo[1,2-a]pyrimidin-7-amine,
2-(4-(fluoromethoxy)phenyl)-N-methylimidazo[1,2-a]pyrimidin-7-amine,
3-(7-(cyclopropylamino)imidazo[1,2-a]pyrimidin-2-yl)phenol,
N-cyclopropyl-2-(3-(2-fluoroethoxy)phenyl)imidazo[1,2-a]pyrimidin-7-amine,
[4-[7-(dimethylamino)imidazo[1,2-a]pyrimidin-2-yl]phenyl]methanol acetic acid adduct,
methyl 4-[7-(methylamino)imidazo[1,2-a]pyrimidin-2-yl]benzoate,
N-cyclopropyl-2-(3-(fluoromethoxy)phenyl)imidazo[1,2-a]pyrimidin-7-amine,
N-cyclopropyl-2-(4-(2-fluoroethoxy)phenyl)imidazo[1,2-a]pyrimidin-7-amine,
N-cyclopropyl-2-(4-(3-fluoropropoxy)phenyl)imidazo[1,2-a]pyrimidin-7-amine,
N-cyclopropyl-2-(4-(fluoromethoxy)phenyl)imidazo[1,2-a]pyrimidin-7-amine,
N-methyl-2-(4-(methylthio)phenyl)imidazo[1,2-a]pyrimidin-7-amine,
2-(3,4-dimethoxyphenyl)-N-methylimidazo[1,2-a]pyrimidin-7-amine,
2-(3-methoxy-4-methylphenyl)-N-methylimidazo[1,2-a]pyrimidin-7-amine, and,
2-(3,5-dimethoxyphenyl)-N-methylimidazo[1,2-a]pyrimidin-7-amine; or,
a pharmaceutically acceptable acid addition salt thereof.

3. A pharmaceutical composition comprising a compound of claim 1 and at least one pharmaceutically acceptable carrier, diluent or excipient.

4. A method of imaging tau-aggregate deposits, beta-amyloid aggregates or alpha-synuclein aggregates comprising the steps of:
 (a) introducing into a mammal a detectable quantity of a compound according to claim 1;
 (b) allowing sufficient time for the compound of claim 1 to be associated with tau-aggregate deposits, and,
 (c) detecting the compound associated with one or more tau-aggregate deposits.

5. The method of claim 4, further defined as a method of diagnostic imaging of tau-aggregate deposits in the brain of a mammal.

6. The method of claim 4, further defined as a method of diagnostic imaging of tau-aggregate deposits in the brain of a mammal for diagnostic the presence of, or monitoring the progression of, Alzheimer's disease.

* * * * *